US011234721B2

(12) United States Patent
Gargac et al.

(10) Patent No.: US 11,234,721 B2
(45) Date of Patent: Feb. 1, 2022

(54) GUIDES AND INSTRUMENTS FOR IMPROVING ACCURACY OF GLENOID IMPLANT PLACEMENT

(71) Applicant: HOWMEDICA OSTEONICS CORP., Mahwah, NJ (US)

(72) Inventors: Shawn M. Gargac, Fort Wayne, IN (US); Nicolas R. Neichel, Le Sappey en Chartreuse (FR); Benoit Le Negaret, Grenoble (FR)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 355 days.

(21) Appl. No.: 16/031,992

(22) Filed: Jul. 10, 2018

(65) Prior Publication Data

US 2019/0015116 A1    Jan. 17, 2019

Related U.S. Application Data

(60) Provisional application No. 62/530,981, filed on Jul. 11, 2017, provisional application No. 62/545,327, filed on Aug. 14, 2017.

(51) Int. Cl.
*A61B 17/17* (2006.01)
*A61B 34/10* (2016.01)
(Continued)

(52) U.S. Cl.
CPC ...... *A61B 17/1778* (2016.11); *A61B 17/1684* (2013.01); *A61B 34/10* (2016.02); *A61F 2/30734* (2013.01); *A61F 2/4081* (2013.01); *A61F 2/4612* (2013.01); *A61B 17/1659* (2013.01); *A61B 2017/568* (2013.01); (Continued)

(58) Field of Classification Search
CPC ............... A61F 2/4612; A61B 17/1778; A61B 2017/568; A61B 17/1684
See application file for complete search history.

(56) References Cited

U.S. PATENT DOCUMENTS 4,919,670 A    4/1990  Dale et al.
5,030,219 A    7/1991  Matsen, III et al.
(Continued)

FOREIGN PATENT DOCUMENTS

CA    2927086    4/2015
CA    2927811    4/2015
(Continued)

OTHER PUBLICATIONS

US 9,451,972 B2, 09/2016, Lang et al. (withdrawn)
(Continued)

Primary Examiner — David W Bates
(74) Attorney, Agent, or Firm — Duane Morris LLP

(57) ABSTRACT

A patient specific shoulder guide is provided that includes a hub and a plurality of peripheral members. Each of the peripheral members has a peripheral member height dimension between the patient specific contact surface and a side of the peripheral member opposite the patient specific contact surface. At least one of the peripheral members is a low profile peripheral member in which the peripheral height dimension is less than the peripheral height dimension of at least one other of the peripheral members or is less than the hub height.

10 Claims, 55 Drawing Sheets

(51) Int. Cl.
  *A61B 17/16* (2006.01)
  *A61F 2/46* (2006.01)
  *A61B 17/56* (2006.01)
  *A61F 2/40* (2006.01)
  *A61F 2/30* (2006.01)

(52) U.S. Cl.
  CPC ... *A61B 2034/105* (2016.02); *A61B 2034/108* (2016.02); *A61F 2002/30736* (2013.01); *A61F 2002/4085* (2013.01); *A61F 2002/4687* (2013.01)

(56) References Cited

U.S. PATENT DOCUMENTS

| | | |
|---|---|---|
| 5,329,846 A | 7/1994 | Bonutti |
| 5,383,938 A | 1/1995 | Rohr et al. |
| 5,458,637 A | 10/1995 | Hayes |
| 5,531,793 A | 7/1996 | Kelman et al. |
| 5,610,966 A | 3/1997 | Martell et al. |
| 5,725,586 A | 3/1998 | Sommerich |
| 5,768,134 A | 6/1998 | Swaelens et al. |
| 5,769,856 A | 6/1998 | Dong et al. |
| 5,779,710 A | 7/1998 | Matsen, III |
| 5,807,437 A | 9/1998 | Sachs et al. |
| 5,824,078 A | 10/1998 | Nelson et al. |
| 5,824,085 A | 10/1998 | Sahay et al. |
| 6,002,859 A | 12/1999 | DiGioia, III et al. |
| 6,129,764 A | 10/2000 | Servidio |
| 6,172,856 B1 | 1/2001 | Jang |
| 6,183,519 B1 | 2/2001 | Bonnin et al. |
| 6,364,910 B1 | 4/2002 | Shultz et al. |
| 6,385,475 B1 | 5/2002 | Cinquin et al. |
| 6,432,142 B1 | 8/2002 | Kamiya et al. |
| 6,459,948 B1 | 10/2002 | Ateshian et al. |
| 6,648,894 B2 | 11/2003 | Abdelgany et al. |
| 6,772,026 B2 | 8/2004 | Bradbury et al. |
| 6,797,006 B2 | 9/2004 | Hodorek |
| 6,849,223 B2 | 2/2005 | Dean et al. |
| 6,915,150 B2 | 7/2005 | Cinquin et al. |
| 6,944,518 B2 | 9/2005 | Roose |
| 7,175,665 B2 | 2/2007 | German et al. |
| 7,468,075 B2 | 12/2008 | Lang et al. |
| 7,469,474 B2 | 12/2008 | Farrar |
| 7,534,263 B2 | 5/2009 | Burdulis, Jr. et al. |
| 7,599,539 B2 | 10/2009 | Kunz et al. |
| 7,618,451 B2 | 11/2009 | Berez et al. |
| 7,634,119 B2 | 12/2009 | Tsougarakis et al. |
| 7,648,530 B2 | 1/2010 | Habermeyer et al. |
| 7,702,380 B1 | 4/2010 | Dean |
| 7,717,956 B2 | 5/2010 | Lang |
| 7,747,305 B2 | 6/2010 | Dean et al. |
| 7,796,791 B2 | 9/2010 | Tsougarakis et al. |
| 7,799,077 B2 | 9/2010 | Lang et al. |
| 7,802,503 B2 | 9/2010 | Couvillion et al. |
| 7,822,588 B2 | 10/2010 | Mueller et al. |
| 7,831,079 B2 | 11/2010 | Kunz et al. |
| 7,892,287 B2 | 2/2011 | Deffenbaugh |
| 7,927,338 B2 | 4/2011 | Laffargue et al. |
| 7,981,158 B2 | 7/2011 | Fitz et al. |
| 7,983,777 B2 | 7/2011 | Melton et al. |
| 7,993,408 B2 | 8/2011 | Meridew et al. |
| 8,007,448 B2 | 8/2011 | Barrera |
| 8,014,984 B2 | 9/2011 | Iannotti et al. |
| 8,055,487 B2 | 11/2011 | James |
| 8,062,302 B2 | 11/2011 | Lang et al. |
| 8,066,708 B2 | 11/2011 | Lang et al. |
| 8,077,950 B2 | 12/2011 | Tsougarakis et al. |
| 8,083,745 B2 | 12/2011 | Lang et al. |
| 8,094,900 B2 | 1/2012 | Steines et al. |
| 8,105,330 B2 | 1/2012 | Fitz et al. |
| 8,122,582 B2 | 2/2012 | Burdulis, Jr. et al. |
| 8,234,097 B2 | 7/2012 | Steines et al. |
| 8,337,501 B2 | 12/2012 | Fitz et al. |
| 8,337,503 B2 | 12/2012 | Lian |
| 8,337,507 B2 | 12/2012 | Lang et al. |
| 8,343,218 B2 | 1/2013 | Lang et al. |
| 8,350,186 B2 | 1/2013 | Jones et al. |
| 8,366,771 B2 | 2/2013 | Burdulis, Jr. et al. |
| 8,377,073 B2 | 2/2013 | Wasielewski |
| 8,377,129 B2 | 2/2013 | Fitz et al. |
| 8,439,926 B2 | 5/2013 | Bojarski et al. |
| 8,457,930 B2 | 6/2013 | Schroeder |
| 8,460,304 B2 | 6/2013 | Fitz et al. |
| 8,475,463 B2 | 7/2013 | Lian |
| 8,480,754 B2 | 7/2013 | Bojarski et al. |
| 8,500,740 B2 | 8/2013 | Bojarski et al. |
| 8,529,568 B2 | 9/2013 | Bouadi |
| 8,529,630 B2 | 9/2013 | Bojarski et al. |
| 8,532,806 B1 | 9/2013 | Masson |
| 8,535,319 B2 | 9/2013 | Ball |
| 8,545,509 B2 | 10/2013 | Park et al. |
| 8,545,569 B2 | 10/2013 | Fitz et al. |
| 8,551,099 B2 | 10/2013 | Lang et al. |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,556,906 B2 | 10/2013 | Fitz et al. |
| 8,556,907 B2 | 10/2013 | Fitz et al. |
| 8,556,971 B2 | 10/2013 | Lang |
| 8,556,983 B2 | 10/2013 | Bojarski et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,585,708 B2 | 11/2013 | Fitz et al. |
| 8,617,172 B2 | 12/2013 | Fitz et al. |
| 8,617,242 B2 | 12/2013 | Philipp |
| 8,623,026 B2 | 1/2014 | Wong et al. |
| 8,634,617 B2 | 1/2014 | Tsougarakis et al. |
| 8,638,998 B2 | 1/2014 | Steines et al. |
| 8,641,716 B2 | 2/2014 | Fitz et al. |
| 8,657,827 B2 | 2/2014 | Fitz et al. |
| 8,682,052 B2 | 3/2014 | Fitz et al. |
| 8,690,945 B2 | 4/2014 | Fitz et al. |
| 8,709,089 B2 | 4/2014 | Lang et al. |
| 8,731,885 B2 | 5/2014 | Iannotti et al. |
| 8,735,773 B2 | 5/2014 | Lang |
| 8,744,148 B2 | 6/2014 | Nord et al. |
| 8,768,028 B2 | 7/2014 | Lang et al. |
| 8,771,365 B2 | 7/2014 | Bojarski et al. |
| 8,774,900 B2 | 7/2014 | Buly et al. |
| 8,775,133 B2 | 7/2014 | Schroeder |
| 8,781,557 B2 | 7/2014 | Dean et al. |
| 8,814,942 B2 | 8/2014 | Anthony et al. |
| 8,843,229 B2 | 9/2014 | Vanasse et al. |
| 8,864,769 B2 | 10/2014 | Stone et al. |
| 8,882,847 B2 | 11/2014 | Burdulis, Jr. et al. |
| 8,884,618 B2 | 11/2014 | Mahfouz |
| 8,888,855 B2 | 11/2014 | Roche et al. |
| 8,898,043 B2 | 11/2014 | Ashby et al. |
| 8,906,107 B2 | 12/2014 | Bojarski et al. |
| 8,926,706 B2 | 1/2015 | Bojarski et al. |
| 8,932,361 B2 | 1/2015 | Tornier et al. |
| 8,932,363 B2 | 1/2015 | Tsougarakis et al. |
| 8,934,961 B2 | 1/2015 | Lakin et al. |
| 8,945,230 B2 | 2/2015 | Lang et al. |
| 8,951,259 B2 | 2/2015 | Fitz et al. |
| 8,951,260 B2 | 2/2015 | Lang et al. |
| 8,965,088 B2 | 2/2015 | Tsougarakis et al. |
| 8,971,606 B2 | 3/2015 | Chaoui |
| 8,974,539 B2 | 3/2015 | Bojarski et al. |
| 8,984,731 B2 | 3/2015 | Broeck et al. |
| 8,989,460 B2 | 3/2015 | Mahfouz |
| 8,992,538 B2 | 3/2015 | Keefer |
| 8,998,915 B2 | 4/2015 | Fitz et al. |
| 9,020,788 B2 | 4/2015 | Lang |
| 9,023,050 B2 | 5/2015 | Lang et al. |
| 9,055,953 B2 | 6/2015 | Lang et al. |
| 9,060,788 B2 | 6/2015 | Bollinger |
| 9,066,728 B2 | 6/2015 | Burdulis, Jr. et al. |
| 9,072,531 B2 | 7/2015 | Fitz et al. |
| 9,084,617 B2 | 7/2015 | Lang et al. |
| 9,095,353 B2 | 8/2015 | Burdulis, Jr. et al. |

(56) References Cited

U.S. PATENT DOCUMENTS

| | | |
|---|---|---|
| 9,107,679 B2 | 8/2015 | Lang et al. |
| 9,107,680 B2 | 8/2015 | Fitz et al. |
| 9,113,921 B2 | 8/2015 | Lang et al. |
| 9,125,672 B2 | 9/2015 | Fitz et al. |
| 9,126,673 B1 | 9/2015 | Green et al. |
| 9,180,015 B2 | 11/2015 | Fitz et al. |
| 9,186,161 B2 | 11/2015 | Lang et al. |
| 9,186,254 B2 | 11/2015 | Fitz et al. |
| 9,208,558 B2 | 12/2015 | Dean et al. |
| 9,211,199 B2 | 12/2015 | Ratron |
| 9,216,025 B2 | 12/2015 | Fitz et al. |
| 9,220,516 B2 | 12/2015 | Lang et al. |
| 9,220,517 B2 | 12/2015 | Lang et al. |
| 9,232,955 B2 | 1/2016 | Bonin, Jr. et al. |
| 9,237,950 B2 | 1/2016 | Hensley et al. |
| 9,241,724 B2 | 1/2016 | Lang et al. |
| 9,241,725 B2 | 1/2016 | Lang et al. |
| 9,275,191 B2 | 3/2016 | Dean et al. |
| 9,278,413 B2 | 3/2016 | Sperling |
| 9,292,920 B2 | 3/2016 | Dean et al. |
| 9,295,481 B2 | 3/2016 | Fitz et al. |
| 9,295,482 B2 | 3/2016 | Fitz et al. |
| 9,301,768 B2 | 4/2016 | Buza et al. |
| 9,308,005 B2 | 4/2016 | Fitz et al. |
| 9,308,053 B2 | 4/2016 | Bojarski et al. |
| 9,308,091 B2 | 4/2016 | Lang |
| 9,314,256 B2 | 4/2016 | Fitz et al. |
| 9,320,608 B2 | 4/2016 | Sperling |
| 9,320,620 B2 | 4/2016 | Bojarski et al. |
| 9,326,780 B2 | 5/2016 | Wong et al. |
| 9,330,206 B2 | 5/2016 | Dean et al. |
| 9,333,085 B2 | 5/2016 | Fitz et al. |
| 9,351,743 B2 | 5/2016 | Kehres et al. |
| 9,358,018 B2 | 6/2016 | Fitz et al. |
| 9,381,025 B2 | 7/2016 | Fitz et al. |
| 9,381,026 B2 | 7/2016 | Trouilloud et al. |
| 9,387,083 B2 | 7/2016 | Al Hares et al. |
| 9,402,726 B2 | 8/2016 | Linderman et al. |
| 9,408,615 B2 | 8/2016 | Fitz et al. |
| 9,408,616 B2 | 8/2016 | Kehres et al. |
| 9,408,686 B1 | 8/2016 | Miller et al. |
| 9,414,928 B2 | 8/2016 | Sperling |
| 9,439,767 B2 | 9/2016 | Bojarski et al. |
| 9,486,226 B2 | 11/2016 | Chao |
| 9,495,483 B2 | 11/2016 | Steines et al. |
| 9,517,134 B2 | 12/2016 | Lang |
| 9,539,013 B2 | 1/2017 | Katrana et al. |
| 9,554,910 B2 | 1/2017 | Vanasse et al. |
| 9,575,931 B2 | 2/2017 | Ratron |
| 9,579,106 B2 | 2/2017 | Lo et al. |
| 9,579,110 B2 | 2/2017 | Bojarski et al. |
| 9,603,711 B2 | 3/2017 | Bojarski et al. |
| 9,615,839 B2 * | 4/2017 | Olson ............... A61B 17/1684 |
| 9,626,756 B2 | 4/2017 | Dean et al. |
| 9,636,229 B2 | 5/2017 | Lang et al. |
| 9,646,113 B2 | 5/2017 | Park et al. |
| 9,662,214 B2 | 5/2017 | Li et al. |
| 9,668,873 B2 | 6/2017 | Winslow et al. |
| 9,672,302 B2 | 6/2017 | Dean et al. |
| 9,672,617 B2 | 6/2017 | Dean et al. |
| 9,675,471 B2 | 6/2017 | Bojarski et al. |
| 9,681,956 B2 | 6/2017 | Al Hares et al. |
| 9,687,945 B2 | 6/2017 | Steines et al. |
| 9,700,420 B2 | 7/2017 | Fitz et al. |
| 9,700,971 B2 | 7/2017 | Lang |
| 9,713,533 B2 | 7/2017 | Taylor et al. |
| 9,715,563 B1 | 7/2017 | Schroeder |
| 9,717,508 B2 | 8/2017 | Iannotti et al. |
| 9,737,367 B2 | 8/2017 | Steines et al. |
| 9,741,263 B2 | 8/2017 | Iannotti et al. |
| 9,770,335 B2 | 9/2017 | Sperling |
| 9,775,680 B2 | 10/2017 | Bojarski et al. |
| 9,849,019 B2 | 12/2017 | Miller et al. |
| 9,872,773 B2 | 1/2018 | Lang et al. |
| 9,877,790 B2 | 1/2018 | Bojarski et al. |
| 9,895,230 B2 | 2/2018 | Mahfouz |
| 9,913,723 B2 | 3/2018 | Fitz et al. |
| 9,937,046 B2 | 4/2018 | Mahfouz |
| 9,943,370 B2 | 4/2018 | Asseln et al. |
| 9,956,047 B2 | 5/2018 | Bojarski et al. |
| 9,956,048 B2 | 5/2018 | Bojarski et al. |
| 9,993,341 B2 | 6/2018 | Vanasse et al. |
| 10,068,671 B2 | 9/2018 | Dean et al. |
| 10,085,839 B2 | 10/2018 | Wong et al. |
| 10,092,419 B2 * | 10/2018 | Hananouchi .......... A61F 2/4657 |
| 10,405,993 B2 * | 9/2019 | Deransart ............ A61F 2/4612 |
| 10,716,676 B2 | 7/2020 | Tornier et al. |
| 10,849,636 B2 * | 12/2020 | Hafez ................ A61B 17/1721 |
| 2001/0047210 A1 | 11/2001 | Wolf |
| 2002/0007294 A1 | 1/2002 | Bradbury et al. |
| 2002/0025358 A1 | 2/2002 | Nelson et al. |
| 2002/0082741 A1 | 6/2002 | Mazumder et al. |
| 2003/0139818 A1 | 7/2003 | Rogers et al. |
| 2004/0064189 A1 | 4/2004 | Maroney et al. |
| 2004/0102866 A1 | 5/2004 | Harris et al. |
| 2004/0133276 A1 | 7/2004 | Lang et al. |
| 2004/0171924 A1 | 9/2004 | Mire et al. |
| 2004/0181144 A1 | 9/2004 | Cinquin et al. |
| 2004/0243481 A1 | 12/2004 | Bradbury et al. |
| 2005/0049709 A1 | 3/2005 | Tornier |
| 2005/0065617 A1 | 3/2005 | Barrera et al. |
| 2005/0065628 A1 | 3/2005 | Roose |
| 2005/0098915 A1 | 5/2005 | Long et al. |
| 2005/0112397 A1 | 5/2005 | Rolfe et al. |
| 2005/0197814 A1 | 9/2005 | Aram |
| 2005/0216305 A1 | 9/2005 | Funderud |
| 2006/0100714 A1 | 5/2006 | Ensign |
| 2006/0136058 A1 | 6/2006 | Pietrzak |
| 2007/0089518 A1 | 4/2007 | Ericson et al. |
| 2007/0118055 A1 | 5/2007 | McCombs |
| 2007/0118243 A1 | 5/2007 | Schroeder et al. |
| 2007/0191741 A1 | 8/2007 | Tsai et al. |
| 2007/0244563 A1 | 10/2007 | Roche et al. |
| 2007/0249967 A1 | 10/2007 | Buly et al. |
| 2008/0014082 A1 | 1/2008 | Kunz et al. |
| 2008/0010900 A1 | 5/2008 | Maroney et al. |
| 2008/0183297 A1 | 7/2008 | Boileau et al. |
| 2008/0228269 A1 | 9/2008 | McLeod et al. |
| 2008/0243127 A1 | 10/2008 | Lang et al. |
| 2009/0204225 A1 | 8/2009 | Meridew et al. |
| 2009/0226068 A1 | 9/2009 | Fitz et al. |
| 2009/0254091 A1 | 10/2009 | Long et al. |
| 2009/0264894 A1 | 10/2009 | Wasielewski |
| 2009/0292464 A1 | 11/2009 | Fuchs et al. |
| 2010/0087927 A1 | 4/2010 | Roche et al. |
| 2010/0161066 A1 | 6/2010 | Iannotti et al. |
| 2010/0191100 A1 | 7/2010 | Anderson et al. |
| 2010/0217270 A1 | 8/2010 | Polinski et al. |
| 2010/0303313 A1 | 12/2010 | Lang et al. |
| 2011/0029088 A1 | 2/2011 | Raucher et al. |
| 2011/0035013 A1 | 2/2011 | Winslow et al. |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0119884 A1 | 5/2011 | Ratron |
| 2011/0137424 A1 | 6/2011 | Lappin et al. |
| 2011/0144760 A1 | 6/2011 | Wong et al. |
| 2011/0282403 A1 | 11/2011 | Anthony et al. |
| 2012/0078258 A1 | 3/2012 | Lo et al. |
| 2012/0109137 A1* | 5/2012 | Iannotti ............. A61B 17/1746 606/87 |
| 2012/0116203 A1 | 5/2012 | Vancraen et al. |
| 2012/0130434 A1 | 5/2012 | Stemniski |
| 2012/0141034 A1 | 6/2012 | Iannotti et al. |
| 2012/0143267 A1* | 6/2012 | Iannotti ................. A61B 34/10 606/86 R |
| 2012/0221112 A1 | 8/2012 | Lappin |
| 2012/0232670 A1 | 9/2012 | Bojarski et al. |
| 2012/0253350 A1 | 10/2012 | Anthony et al. |
| 2012/0276509 A1 | 11/2012 | Iannotti et al. |
| 2012/0279933 A1 | 11/2012 | Hensler et al. |
| 2012/0290272 A1* | 11/2012 | Bryan ............... A61B 17/1684 703/1 |

(56) References Cited

U.S. PATENT DOCUMENTS

| | | | |
|---|---|---|---|
| 2013/0018378 A1* | 1/2013 | Hananouchi | A61B 17/1746 606/87 |
| 2013/0053968 A1 | 2/2013 | Nardini et al. | |
| 2013/0110116 A1 | 5/2013 | Kehres et al. | |
| 2013/0110470 A1 | 5/2013 | Vanasse et al. | |
| 2013/0110471 A1 | 5/2013 | Lang et al. | |
| 2013/0114873 A1 | 5/2013 | Chaoui | |
| 2013/0150975 A1 | 6/2013 | Iannotti et al. | |
| 2013/0172898 A1 | 7/2013 | Iannotti et al. | |
| 2013/0190882 A1 | 7/2013 | Humphrey | |
| 2013/0211531 A1 | 8/2013 | Steines et al. | |
| 2013/0245631 A1* | 9/2013 | Bettenga | A61B 17/1746 606/91 |
| 2013/0261629 A1 | 10/2013 | Anthony et al. | |
| 2013/0274752 A1 | 10/2013 | Trouilloud et al. | |
| 2013/0338673 A1 | 12/2013 | Keppler | |
| 2014/0039633 A1 | 2/2014 | Roche et al. | |
| 2014/0142578 A1* | 5/2014 | Hananouchi | A61B 17/1746 606/87 |
| 2014/0257499 A1 | 9/2014 | Winslow et al. | |
| 2014/0276867 A1 | 9/2014 | Kelley et al. | |
| 2014/0371863 A1 | 12/2014 | Vanasse et al. | |
| 2015/0045903 A1 | 2/2015 | Neal | |
| 2015/0054195 A1 | 2/2015 | Greyf | |
| 2015/0093283 A1 | 4/2015 | Miller et al. | |
| 2015/0150688 A1 | 6/2015 | Vanasse et al. | |
| 2015/0202045 A1 | 7/2015 | Early et al. | |
| 2015/0223941 A1 | 8/2015 | Lang | |
| 2015/0250552 A1 | 9/2015 | Radermacher et al. | |
| 2015/0250597 A1 | 9/2015 | Lang et al. | |
| 2015/0320430 A1 | 11/2015 | Kehres et al. | |
| 2015/0328004 A1 | 11/2015 | Mafhouz | |
| 2016/0015466 A1 | 1/2016 | Park et al. | |
| 2016/0030196 A1* | 2/2016 | Eraly | A61B 17/1739 606/96 |
| 2016/0051367 A1 | 2/2016 | Gervasi et al. | |
| 2016/0067049 A1 | 3/2016 | Flaherty et al. | |
| 2016/0074052 A1 | 3/2016 | Keppler et al. | |
| 2016/0100907 A1 | 4/2016 | Gomes | |
| 2016/0120555 A1 | 5/2016 | Bonin, Jr. et al. | |
| 2016/0143744 A1 | 5/2016 | Bojarski et al. | |
| 2016/0143749 A1 | 5/2016 | Holovacs et al. | |
| 2016/0157937 A1 | 6/2016 | Kehres et al. | |
| 2016/0166392 A1 | 6/2016 | Vanasse et al. | |
| 2016/0184104 A1 | 6/2016 | Sperling | |
| 2016/0193051 A1 | 7/2016 | Budhabhatti et al. | |
| 2016/0213385 A1 | 7/2016 | Iannotti et al. | |
| 2016/0242933 A1 | 8/2016 | Deransart et al. | |
| 2016/0256222 A1 | 9/2016 | Walch | |
| 2016/0270854 A1 | 9/2016 | Chaoui et al. | |
| 2016/0296285 A1 | 10/2016 | Chaoui et al. | |
| 2016/0296290 A1 | 10/2016 | Furrer et al. | |
| 2016/0324648 A1 | 11/2016 | Hodorek et al. | |
| 2016/0331467 A1 | 11/2016 | Slamin et al. | |
| 2016/0345987 A1 | 12/2016 | Guilloux et al. | |
| 2016/0374697 A1 | 12/2016 | Kehres et al. | |
| 2017/0000614 A1 | 1/2017 | Mahfouz | |
| 2017/0000615 A1 | 1/2017 | Mahfouz | |
| 2017/0027587 A1 | 2/2017 | Fraone et al. | |
| 2017/0027593 A1 | 2/2017 | Bojarski et al. | |
| 2017/0056024 A1 | 3/2017 | Chao | |
| 2017/0079803 A1 | 3/2017 | Lang | |
| 2017/0105841 A1 | 4/2017 | Vanasse et al. | |
| 2017/0105843 A1 | 4/2017 | Britton et al. | |
| 2017/0112626 A1 | 4/2017 | Miller et al. | |
| 2017/0119531 A1 | 5/2017 | Bojarski et al. | |
| 2017/0151058 A1 | 6/2017 | Sperling | |
| 2017/0216038 A1 | 8/2017 | Lang et al. | |
| 2017/0231783 A1 | 8/2017 | Lang et al. | |
| 2017/0249440 A1 | 8/2017 | Lang et al. | |
| 2017/0258598 A1 | 9/2017 | Radermacher et al. | |
| 2017/0273795 A1 | 9/2017 | Neichel et al. | |
| 2017/0273800 A1 | 9/2017 | Emerick et al. | |
| 2017/0273801 A1 | 9/2017 | Hodorek | |
| 2017/0281357 A1 | 10/2017 | Taylor et al. | |
| 2017/0296347 A1 | 10/2017 | Chua et al. | |
| 2017/0304063 A1 | 10/2017 | Hatzidakis et al. | |
| 2017/0360567 A1 | 12/2017 | Fitz et al. | |
| 2017/0367766 A1 | 12/2017 | Mahfouz | |
| 2017/0367828 A1 | 12/2017 | Steines et al. | |
| 2017/0367834 A1 | 12/2017 | Fitz et al. | |
| 2018/0028325 A1 | 2/2018 | Bojarski et al. | |
| 2018/0161176 A1 | 6/2018 | Vivanz et al. | |
| 2018/0228614 A1 | 8/2018 | Lang et al. | |
| 2018/0235706 A1 | 8/2018 | Asseln et al. | |
| 2018/0235762 A1 | 8/2018 | Radermacher et al. | |
| 2018/0263782 A1 | 9/2018 | Lang et al. | |
| 2018/0289380 A1 | 10/2018 | Mauldin et al. | |
| 2018/0338769 A1* | 11/2018 | Muir | A61B 17/1684 |
| 2019/0015113 A1 | 1/2019 | Morvan | |
| 2019/0015116 A1 | 1/2019 | Neichel et al. | |
| 2019/0015117 A1 | 1/2019 | Neichel et al. | |
| 2019/0015118 A1 | 1/2019 | Neichel et al. | |
| 2019/0015119 A1 | 1/2019 | Athwal et al. | |
| 2019/0015221 A1 | 1/2019 | Neichel et al. | |
| 2019/0038360 A1 | 2/2019 | Chaoui | |
| 2019/0343658 A1 | 11/2019 | Deransart et al. | |
| 2020/0188121 A1 | 6/2020 | Boux de Casson et al. | |
| 2020/0214845 A1 | 7/2020 | Knox et al. | |

FOREIGN PATENT DOCUMENTS

| | | |
|---|---|---|
| CA | 2938709 | 5/2015 |
| DE | 10 2006 047663 | 4/2008 |
| EP | 1 249 213 | 10/2002 |
| EP | 1 265 555 | 12/2002 |
| EP | 1 563 810 | 8/2005 |
| EP | 1 862 151 | 12/2007 |
| EP | 1 902 689 | 3/2008 |
| EP | 1 952 788 | 8/2008 |
| EP | 2 135 576 | 12/2009 |
| EP | 1 917 051 B1 | 6/2010 |
| EP | 2 243 445 | 10/2010 |
| EP | 2 324 801 | 5/2011 |
| EP | 2 335 655 | 6/2011 |
| EP | 2 501 313 | 9/2012 |
| EP | 2 544 601 | 1/2013 |
| EP | 2 583 242 | 4/2013 |
| EP | 2 653 136 | 10/2013 |
| EP | 2 845 547 | 3/2015 |
| EP | 2 965 720 | 1/2016 |
| EP | 3 057 518 | 8/2016 |
| EP | 3 057 524 | 8/2016 |
| EP | 3 065 671 | 9/2016 |
| EP | 3 068 317 | 9/2016 |
| EP | 2 874 570 B1 | 1/2017 |
| EP | 3 117 801 | 1/2017 |
| FR | 2 579 454 | 10/1986 |
| FR | 2 859 099 | 3/2005 |
| FR | 2962573 | 1/2012 |
| FR | 2982694 | 11/2016 |
| FR | 2982979 | 11/2016 |
| FR | 2982693 | 12/2016 |
| GB | 2501494 A | 10/2013 |
| WO | WO 93/025157 | 12/1993 |
| WO | WO 00/35346 | 6/2000 |
| WO | WO 00/59411 | 10/2000 |
| WO | WO 02/061688 | 8/2002 |
| WO | WO 2010/120346 | 10/2010 |
| WO | WO 2011/110374 | 9/2011 |
| WO | WO 2011/154891 | 12/2011 |
| WO | WO 2011/157961 | 12/2011 |
| WO | WO 2012/021241 | 2/2012 |
| WO | WO 2012/058349 | 5/2012 |
| WO | WO 2012/125319 | 9/2012 |
| WO | WO 2013/060851 | 5/2013 |
| WO | WO 2013/062848 | 5/2013 |
| WO | WO 2013/062851 | 5/2013 |
| WO | WO 2013/142998 | 10/2013 |
| WO | WO 2014/020561 | 2/2014 |
| WO | WO 2014/035991 | 3/2014 |
| WO | WO 2014/180972 | 11/2014 |
| WO | WO 2015/052586 | 4/2015 |
| WO | WO 2015/056097 | 4/2015 |

(56) References Cited

FOREIGN PATENT DOCUMENTS

| WO | WO 2015/068035 | 5/2015 |
|---|---|---|
| WO | WO 2015/071757 | 5/2015 |
| WO | WO 2015/175397 | 11/2015 |
| WO | WO 2015/185219 | 12/2015 |
| WO | WO 2017/005514 | 1/2017 |
| WO | WO 2017/007565 | 1/2017 |
| WO | WO 2017/091657 | 6/2017 |
| WO | WO 2017/105815 | 6/2017 |
| WO | WO 2017/106294 | 6/2017 |
| WO | WO 2017/184792 | 10/2017 |
| WO | WO 2017/214537 | 12/2017 |
| WO | WO 2018/022227 | 2/2018 |
| WO | WO 2019/014278 | 1/2019 |
| WO | WO 2019/014281 | 1/2019 |
| WO | WO 2019/033037 | 2/2019 |
| WO | WO 2019/060780 | 3/2019 |

OTHER PUBLICATIONS

Zimmer, "Zimmer® PSI Shoulder Trabecular Metal™ Reverse Glenoid Base Plate Surgical Technique", Dec. 30, 2013.
Boileau, et al., "The three-dimensional geometry of the proximal humerus: implications for surgical technique and prosthetic design." The Journal of bone and joint surgery. British vol. 79.5 (1997): 857-865.
Dougherty, "Digital Image Processing for Medical Applications," May 11, 2009 (May 11, 2009), Cambridge University Press, XP002615721.
Favre, et al., "Influence of component positioning on impingement in conventional total shoulder arthroplasty," Clinical Biomechanics, Butterworth Scientifics, Nov. 5, 2007, pp. 174-183, vol. 23, No. 2, Guilford, GB.
Gregory, et al.,"Accuracy of Glenoid Component Placement in Total Shoulder Arthroplasty and Its Effect on Clinical and Radiological Outcome in a Retrospective, Longitudinal, Monocentric Open Study," PLoS One, p. e75791, Aug. 1, 2013, vol. 8, No. 10.
Habets, et al., Computer assistance in orthopaedic surgery. Technische Universiteit Eindhoven, 2002.
Hempfing, et al. "Surgical landmarks to determine humeral head retrotorsion for hemiarthroplasty in fractures." Journal of shoulder and elbow surgery 10.5 (2001): 460-463.
Hernigou, et al., "Determining humeral retroversion with computed tomography." Journal of bone and joint surgery. Oct. 2002;84-A(10):1753-62.
Iannotti et al., "Prosthetic positioning in total shoulder arthroplasty," Journal of Shoulder and Elbow Surgery, Jan. 1, 2005, vol. 14, No. 1S, pp. S111-S121.
Kobashi et al., "Knowledge-Based Organ Identification from CT Images," Pattern Recognition, Elsevier, GB, vol. 28, No. 4, Apr. 1, 1995 (Apr. 1, 1995), pp. 475-491, XP004013165.
Lee, C.C. et al., "Identifying multiple abdominal organs from CT image series using a multimodule contextual neural network and spatial fuzzy rules", IEEE Transactions on Information Technology in Biomedicine, IEEE Services Center, Los Alamitos, CA, US, vol. 7, No. 3, Sep. 1, 2003 (Sep. 1, 2003) pp. 208-217, XP011100536.
Lee, C.C. et al., "Recognizing Abdominal Organs in CT Images Using Contextual Neural Network and Fuzzy Rules", Engineering in Medicine and Biology Society, 2000. Proceedings of the 22nd Annual International Conference of the IEEE Jul. 23-28, 2000, Piscataway, NJ, USA, IEEE, vol. 3, Jul. 23, 2000 (Jul. 23, 2000), pp. 1745-1748, XP010530837.
Ma, et al., "Robust registration for computer-integrated orthopedic surgery: laboratory validation and clinical experience." Medical image analysis 7.3 (2003): 237-250.
"Olympia Total Shoulder System Surgical Technique", Wright Medical Technology, 2001, in 19 pages.
Nguyen, et al., "A New Segmentation Method for MRI Images of the Shoulder Joint", Computer and Robot Vision, 2007. CRV '07. Fourth Canadian Conference on, IEEE, PI, May 1, 2007 (May 1, 2007), pp. 329-338, XP031175821.
Radermacher, K., et al., "Computer Assisted Orthopaedic Surgery with Image Based Individual Templates," Clinical Orthopaedics and Related Research, No. 354, Sep. 1998, pp. 28-38.
Radermacher, K., et al., "Image Guided Orthopedic Surgery Using Individual Templates: Experimental Results and Aspects of the Development of a Demonstrator for Pelvis Surgery", Health Care Sector, Telematics Applications Program, 1997, pp. 606-615.
Tamez-Pena et al., "The Integration of Automatic Segmentation and Motion Tracking for 4D Reconstruction and Visualization of Musculoskeletal Structures," Biomedical Image Analysis, 1998. Proceedings. Workshop on Santa Barbara, CA US, Jun. 26-27, 1998, Los Alamitos, CA, USA, IEEE Comput. Soc. US, Jun. 26, 1998 (Jun. 26, 1998), pp. 154-163, XP010291418.
Tornier, "Salto Talaris, Total Ankle Prosthesis", 2009.
Valstar, et al. "Towards computer-assisted surgery in shoulder joint replacement." ISPRS journal of photogrammetry and remote sensing 56.5-6 (2002): 326-337.
Valstar, et al. "The use of Roentgen stereophotogrammetry to study micromotion of orthopaedic implants." ISPRS journal of photogrammetry and remote sensing 56.5-6 (2002): 376-389.
Welsh, et al., "CT-based preoperative analysis of scapula morphology and glenohumeral joint geometry." Computer Aided Surgery 8.5 (2003): 264-268.
Wu, et al. "An interface for the data exchange between CAS and CAD/CAM systems." International Congress Series. vol. 1256. Elsevier, 2003.
"Zimmer® PSI Shoulder Planning", Zimmer Biomet TV, posted Jul. 11, 2014, retrieved from internet on Jan. 9, 2020, <https://zimmerbiomet.tv/videos/1025?a=surgeon&version=1190>.
International Search Report and Written Opinion issued in PCT Application No. PCT/US2018/041526, dated Dec. 4, 2018, in 20 pages.
Final Rejection issued in connection with U.S. Appl. No. 15/426,720, filed Apr. 29, 2021, 15 pages.
Non-Final Office Action issued in connection with U.S. Appl. No. 16/785,228, filed May 27, 2021, 33 pages.

* cited by examiner

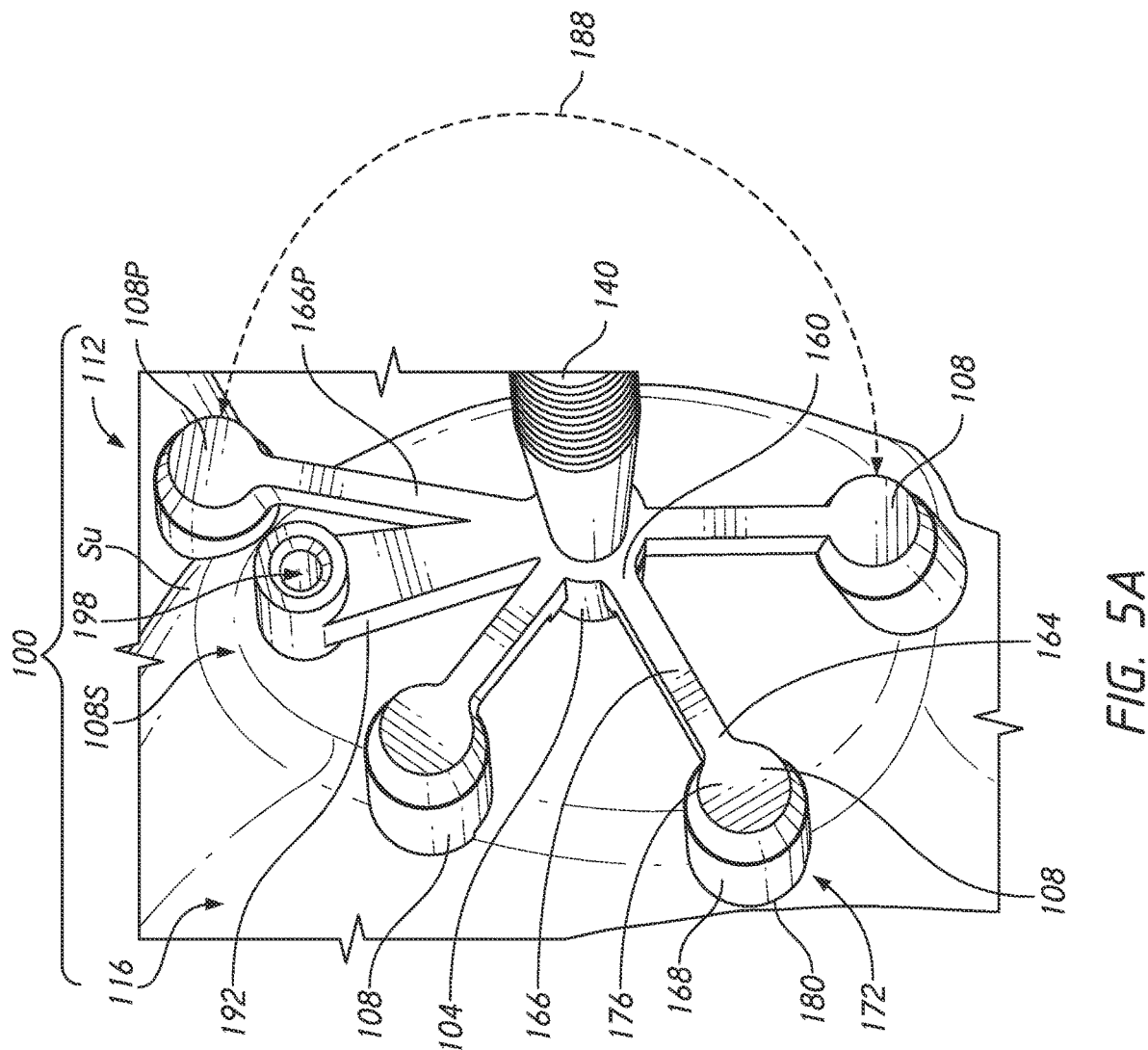

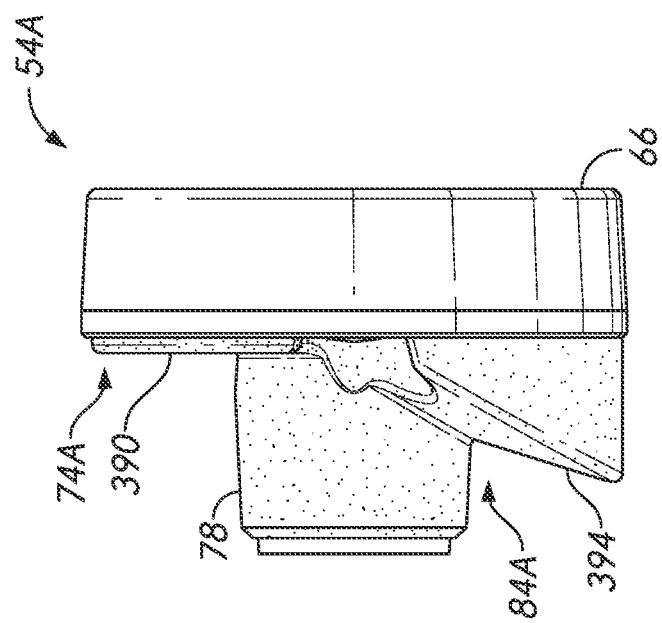
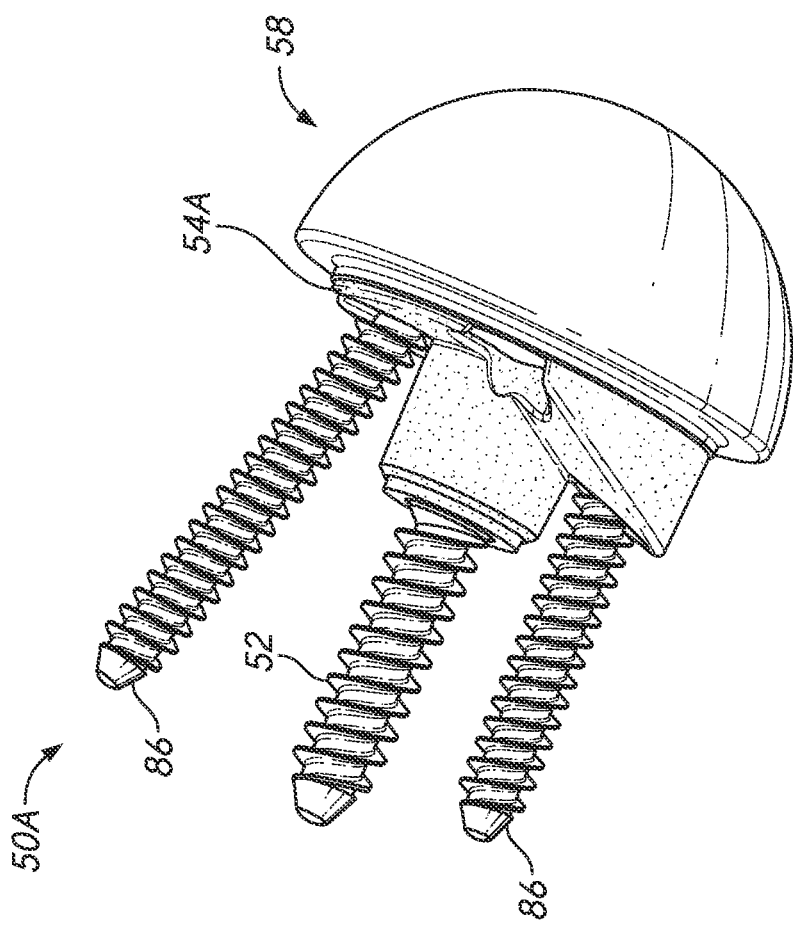

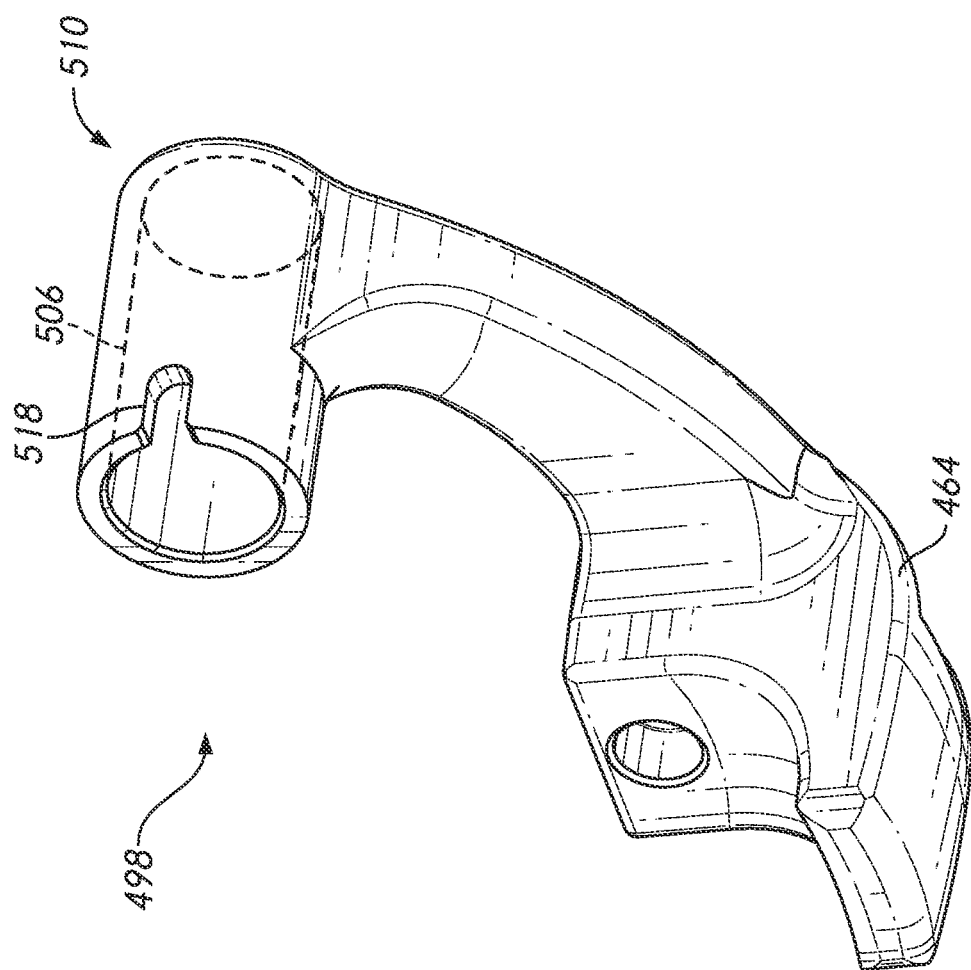

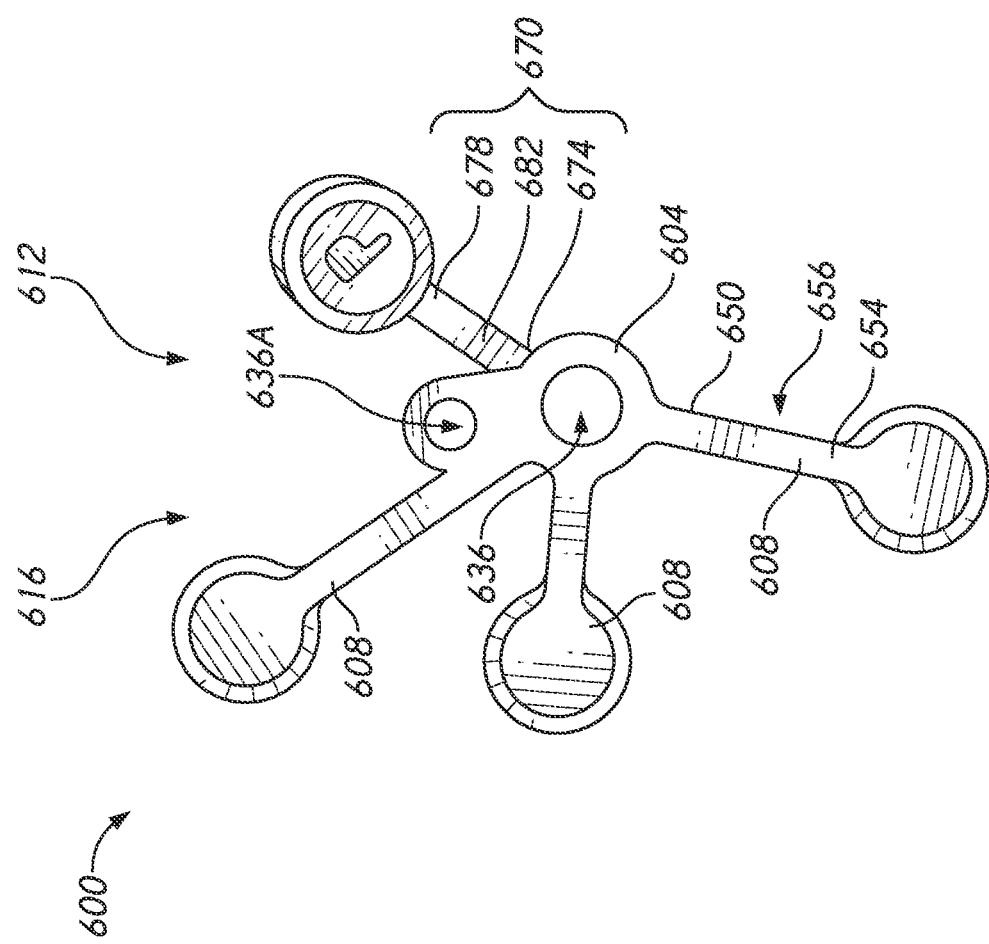

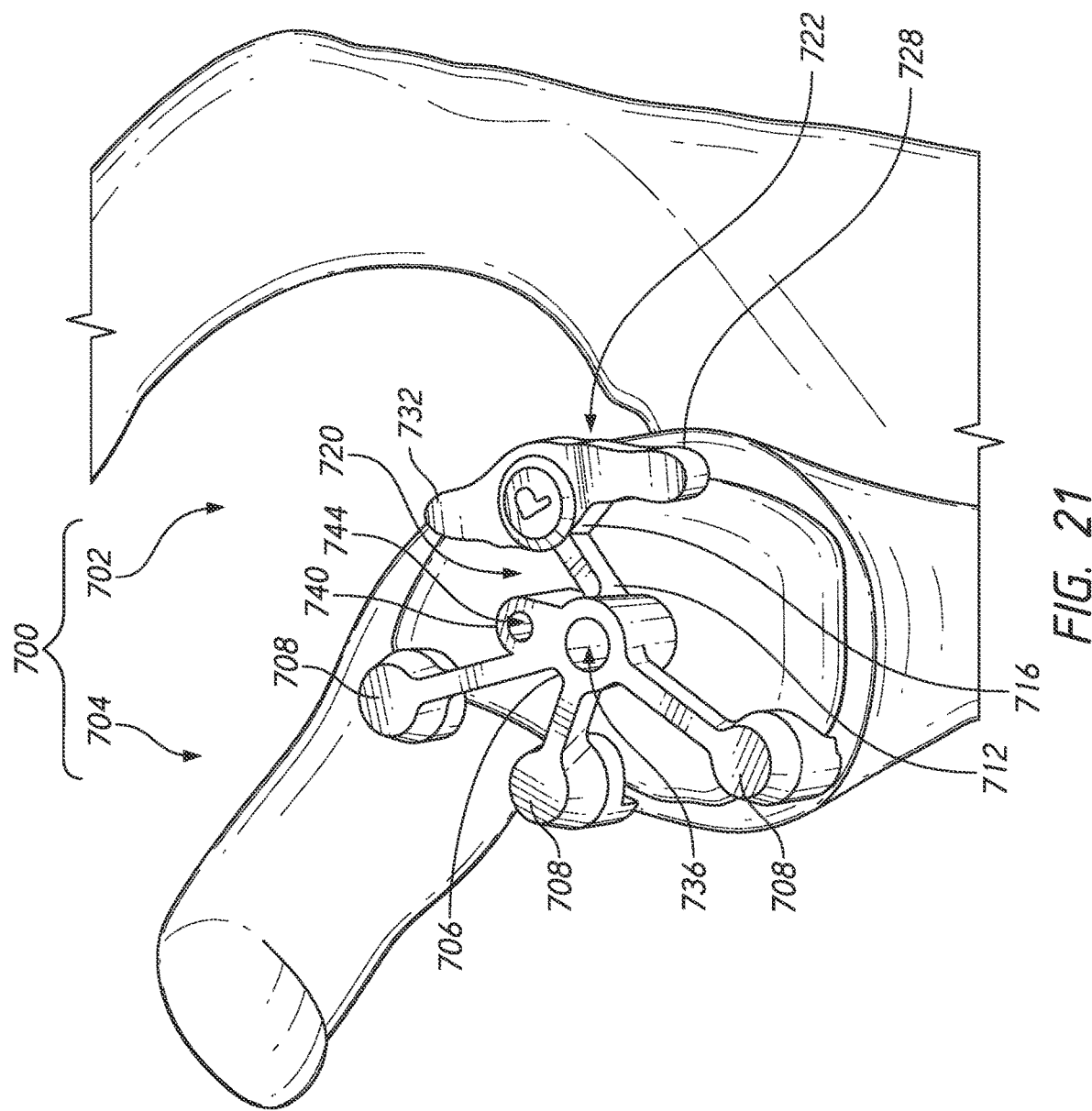

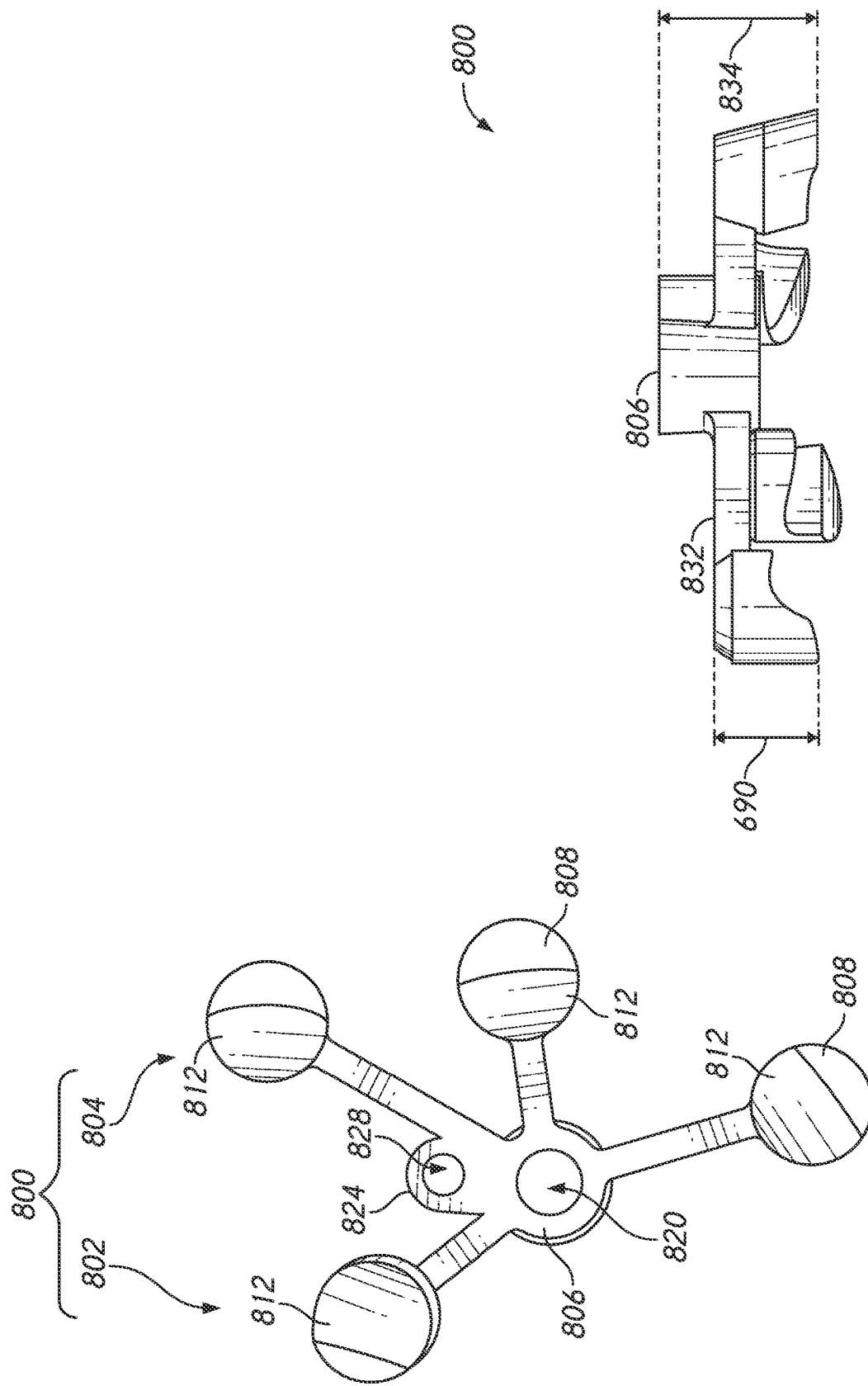

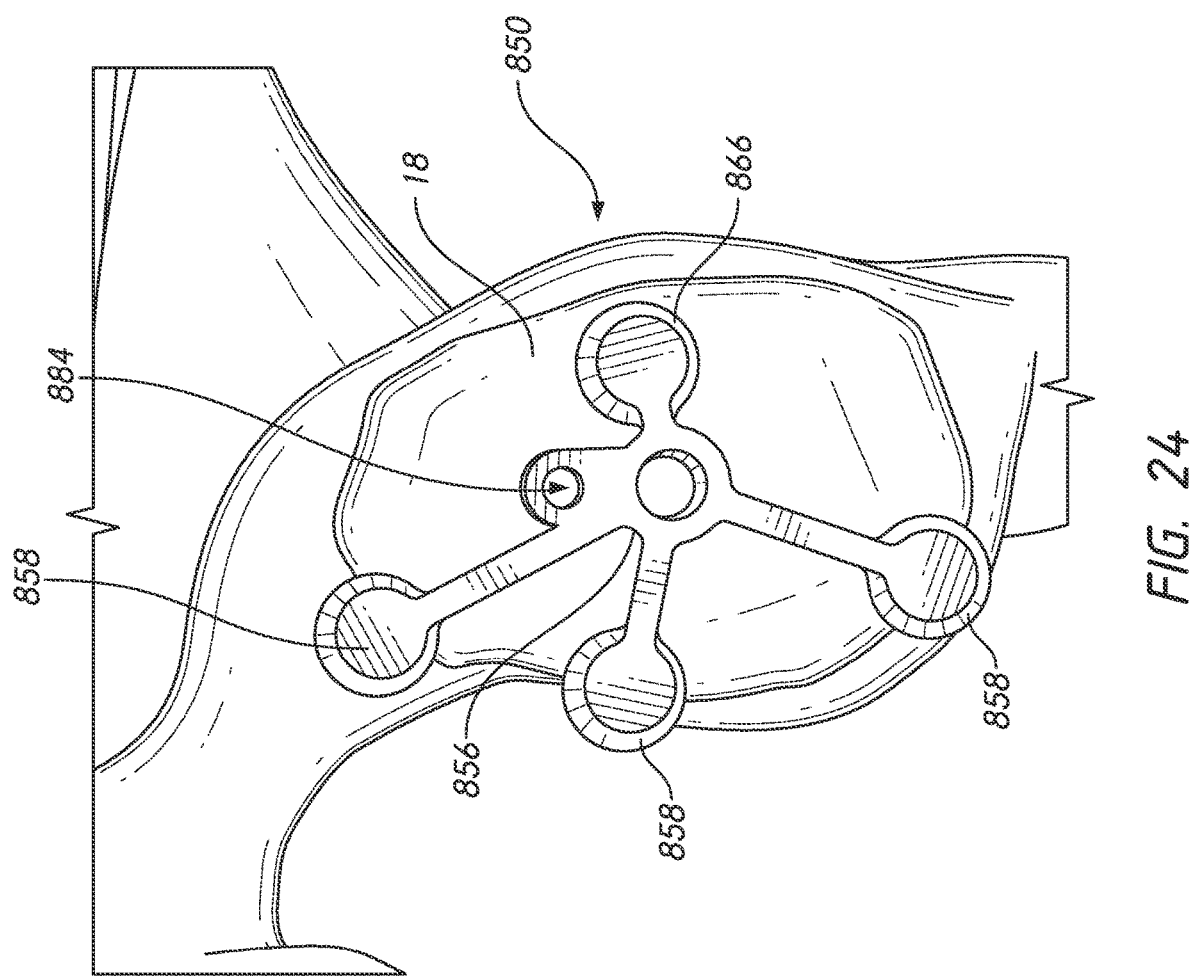

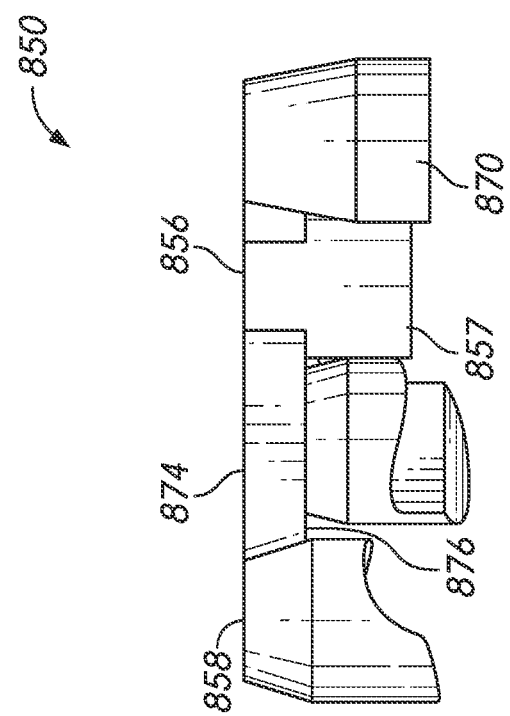
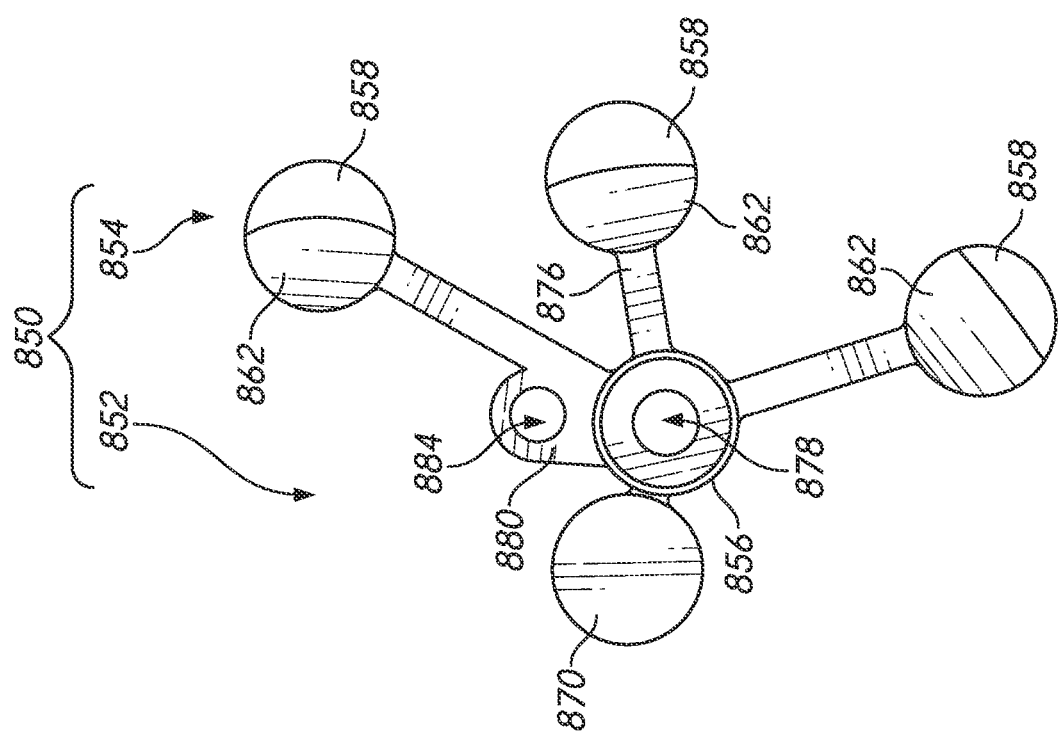
FIG. 24A
FIG. 24B

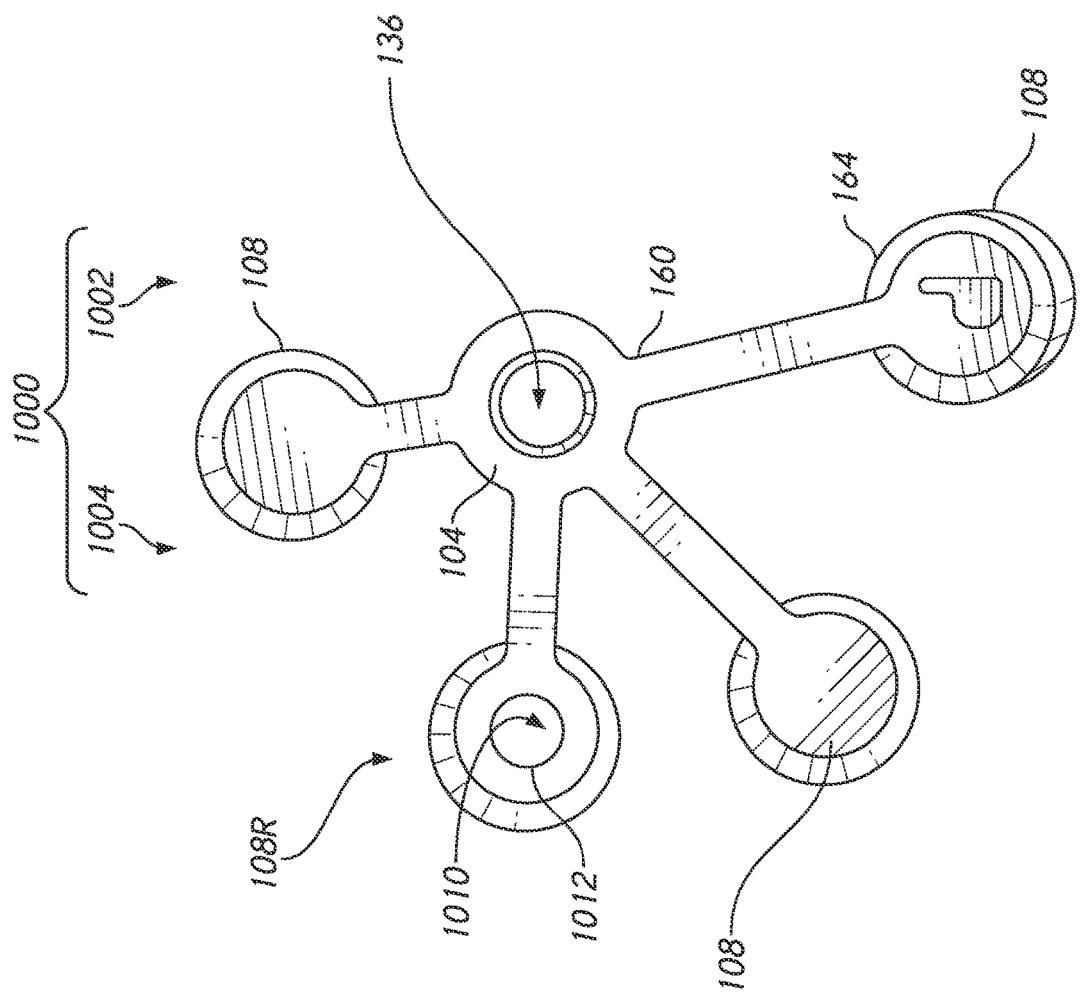

GUIDES AND INSTRUMENTS FOR IMPROVING ACCURACY OF GLENOID IMPLANT PLACEMENT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND

Field

The present disclosure relates to patient specific shoulder apparatuses and methods.

Description of the Related Art

Shoulder arthroplasty is an important solution to many shoulder joint ailments. The procedure can involve replacing or repairing the articular surface of one or both of the humerus and the glenoid to restore shoulder joint function, to eliminate shoulder joint pain, and to improve quality of life for patients with debilitating shoulder joint pain.

FIG. 1 illustrates a glenohumeral joint 8. An incision can be formed in the tissue over the joint 8 to surgically expose a head 10 of the humerus 12. The head 10 can be separated from the scapula 14 to provide access to the glenoid 18. FIG. 1A shows that retractors 16 can be used to displace tissue surrounding the glenoid 18 to enhance access thereto. The retractors 16 help maintain an exposed surgical field during the procedure.

In shoulder arthroplasty, an articular implant can repair or replace the articular surface of the glenoid 18. The glenoid 18 is prepared by being reamed a suitable amount and thereafter the articular implant is attached to the reamed surface. The articular surfaces of the humerus 12 and the glenoid 18 can be reversed in some cases, providing a concave articular member on the humerus 12 and a convex member on the glenoid 18. In some cases the glenoid surface is worn away and the glenoid surface is enhanced to make up for worn bone. In these cases poor articular implant orientation can lead to poor results.

SUMMARY

There is a need for improved surgical guides that can improve placement of articular implants of the glenoid. There is a need for improved surgical guides that can aid in orienting glenoid articular implants. There is a need for improved surgical guides that can aid in forming channels for screws and other anchors for glenoid articular implants. There is a need for surgical guides that have improved stability and for guides that can be placed on the glenoid without obstructing, interacting with and potentially being disrupted by or disrupting the position or operation of tissue retractors and other surgical tools. There is a need for patient specific surgical guides that can provide any or all of these and other improved characteristics.

In one embodiment, a patient specific shoulder guide is provided that includes a hub and a plurality of peripheral members. The hub has a first end configured to face a central glenoid surface, a second end opposite the first end, and an elongate hub body that extends from the first end to the second end. The elongate hub body defines a hub height dimension that extends between the first end and the second end. The peripheral members have an inner end coupled with the hub, an outer end disposed radially away from the hub, and a patient specific contact surface disposed at the outer end of the peripheral member. Each of the peripheral members has a peripheral member height dimension between the patient specific contact surface and a side of the peripheral member opposite the patient specific contact surface. At least one of the peripheral members is a low profile peripheral member in which the peripheral height dimension is less than the peripheral height dimension of at least one other of the peripheral members or is less than the hub height.

In another embodiment, a patient specific shoulder guide is provided. The patient specific shoulder guide includes a central member and a plurality of peripheral members. The central member is configured to contact a location of a glenoid surface located inward of a glenoid rim of a glenoid. The peripheral members each have a patient specific surface configured to contact points of the glenoid rim of the glenoid of a specific patient. The peripheral members and the central member provide for stable positioning of the patient specific shoulder guide. In use, all of the peripheral members contact an anterior portion of the glenoid rim. In this embodiment, there is optionally a side channel for securing the guide against rotation.

In another embodiment, a method is provided. A patient specific glenoid guide is placed on a surface of a scapula of a patient. The guide has a patient specific bone contact surface. The guide is placed such that the patient specific bone contact surface is in contact with a corresponding bone surface. A peripheral guide pin is advanced into the scapula near a peripheral region of a glenoid of the patient with reference to the patient specific glenoid guide.

In one variation of the foregoing method, an aperture of an anchor trajectory guide is advanced over the peripheral guide pin to a predefined position over the glenoid. A peripheral anchor channel is formed in the scapula from the glenoid surface toward an opposing cortical bone region. A reverse shoulder implant baseplate is secured on the glenoid surface by advancing a peripheral anchor through the peripheral anchor channel formed through the anchor trajectory guide.

In another embodiment, a method is performed in which an anchor trajectory guide is positioned in a predefined position over a glenoid surface of a patient. A peripheral anchor channel is formed in a scapula from the glenoid surface toward an opposing cortical bone region. A shoulder implant is secured on the glenoid surface by advancing a peripheral anchor into the peripheral anchor channel formed through the anchor trajectory guide.

In one variation, a patient specific glenoid guide is placed on a surface of the scapula of a patient with the patient specific glenoid guide in contact with a corresponding bone surface. A peripheral guide pin is advanced into the scapula near a peripheral region of a glenoid of the patient with reference to the patient specific glenoid guide. An aperture of the anchor trajectory guide is advanced over the peripheral guide pin.

The foregoing method can be employed to place a reverse shoulder implant baseplate. The method can include coupling the reverse shoulder implant baseplate to the anchor trajectory guide prior to positioning the anchor trajectory guide in the predefined position over the glenoid. A projection disposed on a bone facing side of the anchor trajectory guide can be coupled with a recess in the reverse shoulder baseplate to couple the reverse shoulder implant baseplate to the anchor trajectory guide. One or more peripheral members of the guide can be coupled with a corresponding one or more tooling interfaces of the reverse shoulder baseplate to couple the reverse shoulder implant baseplate to the anchor trajectory guide.

In a further variation, the reverse shoulder baseplate can be rotationally oriented such that an augmented portion thereof is oriented toward a portion of the glenoid for which the augmented portion has been configured.

The patient specific glenoid guide can be formed such that a central guide feature is disposed to be near a central region of the glenoid when the guide is used. In one case, the central guide feature is established, at least in part by, advancing over a central guide pin extending from the central region of the glenoid.

In some methods, a reamer is advanced with reference to one or both of the central guide pin or the peripheral guide pin to the glenoid surface. The glenoid surface is reamed with reference to the guide pin(s).

In another embodiment, a method of reaming a glenoid is provided. A patient specific glenoid guide having a patient specific bone contact surface is placed on a surface of a scapula of a patient. The guide is placed such that the patient specific bone contact surface is in contact with a corresponding bone surface. A central guide feature that extends from a central surface of the glenoid is established. The central guide feature is established by reference to the patient specific glenoid guide. A peripheral guide feature that extends from a surface of the scapula peripheral to the central surface of the glenoid is established. The peripheral guide feature is established by reference to the patient specific glenoid guide. A reaming guide is coupled to a reamer. After coupling the reaming guide to the reamer, the reaming guide is advanced over or into a proximal portion of the peripheral guide feature. The reamer is advanced to the glenoid surface by reference to the central guide feature and by reference to the peripheral guide feature. The glenoid surface is reamed by continued reference to the central guide feature and by reference to the peripheral guide feature.

In another embodiment, a patient specific shoulder guide is provided. The guide has a central hub, and a plurality of peripheral locating members. The central hub has a channel therethrough. The channel is positioned and oriented to define an axis along which a central guide pin can be placed in a glenoid of a patient. Each of the peripheral locating members is elongate with an inner end coupled with the central hub and an outer end. The outer end is disposed away from the central hub. A patient specific contact member is coupled with the outer end of the peripheral locating member. A peripheral member that has a peripheral channel therethrough is configured to direct a peripheral guide pin into a scapula adjacent to a rim of the glenoid outside the central region of the glenoid.

Any of the patient specific shoulder guides disclosed herein can include a surface configured to mate with a feature of a glenoid of a patient.

In some embodiments, one or more of the patient specific contact members are formed as a substantial negative of corresponding portions of the glenoid of the patient. The peripheral member can have the peripheral channel disposed in a portion of the shoulder guide configured to be disposed over a superior portion of the glenoid when the patient specific contact members are in contact with a surface of which they are a substantial negative.

The peripheral member can have a peripheral channel configured to be spaced away from the scapula when the patient specific contact members are in contact with a surface of which they are a substantial negative. The peripheral channel can have a trajectory that is patient specific. The peripheral channel(s) can be configured to direct a guide pin into a portion of the scapula outside the glenoid rim. The peripheral channel(s) can be configured to direct a guide pin into a portion of the scapula inside the glenoid rim.

One or more of the peripheral members can be a low profile member in which a peripheral height dimension is less than a height of a central hub. Two adjacent peripheral locating members can be disposed in a posterior portion of the shoulder guide and can be separated by an unobstructed region of at least 45 degrees, or of at least 90 degrees. The shoulder guide can be configured in a patient specific manner such that the peripheral channel will be disposed in a location outside of, e.g., opposite to, a region of the scapula to be reamed during a procedure to place an implant on the glenoid.

In another embodiment, a reaming guide is provided that includes a peripheral member configured to mate with a peripheral guide feature and a rigid body. The rigid body extends from the peripheral member to adjacent to a reaming head of a reamer in use. The rigid body is configured to be mounted to the reamer proximal of the reaming head. The reaming guide includes a depth stop coupled with the rigid body. The depth stop has a distal portion configured to contact a first reamed glenoid surface or other surface of the scapula when the reaming head has fully reamed a glenoid surface to a planned depth in preparation for an augmented glenoid component. The reaming guide can be used to control the preparation of a surface that can be disposed at an angle to a first reamed surface or that can be disposed at a non-orthogonal angle to a guide pin or at a non-orthogonal angle to a medial-lateral axis of the patient.

In another embodiment, a patient-specific screw anchor trajectory guide is provided. The screw anchor trajectory guide includes a body, a locating aperture, and a plurality of peripheral screw apertures. The body is configured to be placed over a reverse shoulder assembly baseplate. The locating aperture is disposed through the body and is configured to be advanced over a guide pin to locate the body relative to a glenoid. The plurality of peripheral screw apertures are disposed through the body and located inferior of the locating aperture at positions corresponding to pre-defined peripheral screw locations. The peripheral screw channel apertures are located and oriented to provide good purchase in scapular bone around the glenoid for a specific patient.

In some embodiments, a screw anchor trajectory guide can have a body that has a first side configured to face toward the glenoid surface in use and a second side opposite the first side. The first side can have a projection configured to be received in a recess of a glenoid baseplate to facilitate positioning the baseplate at the same time the screw guide is positioned to form peripheral screw channels.

One or more peripheral members can be provided on the first side of a guide body. The peripheral members can be configured to engage tooling interfaces of a baseplate to facilitate positioning the baseplate at the same time the screw guide is positioned to form peripheral screw channels. The peripheral members can be disposed circumferentially between adjacent holes of the plurality of peripheral screw apertures. The peripheral members can be disposed in an inferior portion and in a superior portion of the body of the screw guide.

In some embodiments, a distance from a locating aperture of a guide to a central portion of a medial projection of a body of the guide can be configured for a specific patient. One or more of the peripheral screw apertures can be configured for a specific patient. The peripheral screw apertures can comprise a superior hole, an inferior hole, an anterior hole, and a posterior hole.

At least one of a plurality of peripheral screw apertures can be disposed along an axis selected to cause a peripheral screw directed along the axis to reach cortical bone through cancellous bone beneath the glenoid.

At least two opposite peripheral screw apertures of a guide can be disposed through a body of the guide along diverging axes.

In other embodiments, a surgical instrument is provided for implanting an augmented glenoid implant. The instrument includes an outer shell, an inner shell, and a rotation guide. The outer shell has an elongate body that has a first end and a second end. The outer shell has a glenoid implant component retention feature disposed on the first end. The inner shell is slideably disposed in the outer shell. The inner shell has a first position and a second position within the outer shell. The first position is closer to the first end of the outer shell than is the second position. The inner shell is configured to actuate the glenoid implant component retention feature to a retention configuration when in the first position relative to the outer shell. The rotation guide has an instrument interface and a bone interface portion disposed on another end thereof. The rotation guide has a rigid body disposed between the instrument interface and the bone interface portion. The shape and/or length of the rigid body optionally is/are configured for a specific patient to control the rotational position of the glenoid implant component. In some embodiment, the shape of the rigid body is configured for a specific patient to control the rotational position of the glenoid implant component. In some embodiments the length of the rigid body is configured for a specific patient to control the rotational position of the glenoid implant component. In some embodiments the shape and the length of the rigid body is configured for a specific patient to control the rotational position of the glenoid implant component. The surgical instrument comprises an interface portion configured to releasably engage the rotation guide.

In some cases, the shape and/or length of the rigid body is/are not patient specific but rather are generic. For example, a kit of rotation guides can be provided where each rigid body includes a generic body to suit a small, a medium, or a large glenoid. The kit can further include for each size option a plurality of rotation guides with rigid bodies configured to align an instrument, such as a reamer or implant driver, with specific anatomy requiring augmentations, such as with posterior, inferior, anterior, or superior regions of the glenoid and any region therebetween.

In another embodiment a patient specific glenoid guide has a hub and a plurality of peripheral members. The hub has a first end configured to face a central glenoid surface, a second end opposite the first end, and an elongate hub body that is disposed between the first end and the second end. The elongate hub body has a central channel therethough. The peripheral members have an inner end coupled with the hub, an outer end disposed radially away from the hub, and a patient specific contact surface at the outer end. At least one of the peripheral members has a rotation control feature forming channel configured for forming a visual indicator on a scapula of a specific patient in a prescribed position relative to a portion of the glenoid of the specific patient to be augmented by an augmented glenoid implant.

In another embodiment a method is provided for aligning a rotationally asymmetric glenoid component to a glenoid of a specific patient. The glenoid is exposed. A glenoid guide is applied to the glenoid. The glenoid guide has a rotation control feature forming member. A rotation control feature is formed with reference to the rotation control feature forming member in or on the scapula at or adjacent to the glenoid. The rotation control feature can be used for guiding a reamer to form a surface ready to receive a rotationally asymmetric glenoid component. The surface can be disposed at a non-orthogonal angle to a guide pin or to the orientation of a longitudinal axis of the reamer and/or at an acute angle to another reamed glenoid surface. Whether or not the rotation control feature is used to control the reamer, the rotationally asymmetric glenoid component can be advanced onto the glenoid with reference to the rotation control feature to align the rotationally asymmetric glenoid component to the glenoid in a prescribed rotational orientation for the specific patient. The rotationally asymmetric glenoid component is secured to the glenoid in the prescribed rotational orientation for the specific patient.

The rotation control feature forming member can include a superior peripheral member with an aperture and/or a guiding peripheral member with a channel. The rotation control feature can be configured to guide advancement of a reamer to form a surface ready to receive a rotationally asymmetric glenoid component. The surface can be disposed at a non-orthogonal angle to a guide pin or to the orientation of a longitudinal axis of the reamer and/or at an acute angle to another reamed glenoid surface. Whether or not the rotation control feature is used to control the reamer, the rotation control feature can be configured to guide placement of a rotationally asymmetric glenoid component. The channel in the guiding peripheral member can be a slot or other open sided channel or can be a lumen or other closed periphery channel.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

These and other features, aspects and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. In the drawings, like reference characters denote corresponding features consistently throughout similar embodiments. The following is a brief description of each of the drawings.

FIG. 5A is an enlarged view of the patient specific glenoid guide of FIG. 5;

FIG. 10 shows a reverse shoulder glenoid implant similar to that of FIG. 3, where a baseplate thereof is augmented on a medial side thereof;

FIG. 10A shows a side view of the augmented baseplate of FIG. 10;

FIGS. 16A-16B illustrate components of the peg assembly of FIGS. 14-15 in greater detail;

FIG. 20A is a lateral or proximal side view of the glenoid guide of FIG. 20;

FIG. 21 is a lateral side perspective view of another embodiment of a low profile glenoid guide placed on a scapula, the guide providing improved clearance for a tissue retractor when so placed;

FIG. 23A is a medial or distal side view of the glenoid guide of FIG. 23;

FIG. 23B is a side view of the glenoid guide of FIG. 23;

FIG. 24 is a lateral side view of another embodiment of a low profile glenoid guide placed on a scapula, the guide providing improved clearance for a tissue retractor;

FIG. 24A is a medial or distal side view of the glenoid guide of FIG. 24;

FIG. 24B is a side view of the glenoid guide of FIG. 24;

FIG. 27A is a lateral side view of another embodiment of a patient specific glenoid guide configured for forming a rotation control feature;

DETAILED DESCRIPTION OF THE PREFERRED EMBODIMENT

This application is directed to shoulder joint arthroplasty apparatuses and methods, which in some cases are patient specific. Section I discusses glenoid implants and the positioning of the same, addressing some sub-optimal outcomes that can be improved by the surgical guides disclosed herein.

Section II discusses methods and apparatuses for enhanced control of bone preparation for glenoid implants. Section II also discusses methods and apparatuses for enhanced control of the mating of articular implant with the glenoid. Surgical guides are discussed that enhance control of the rotational orientation of glenoid implant components. Section III discusses methods and apparatuses for enhanced control of reaming of a glenoid surface. Reaming guides are discussed that enhance the control of the process of reaming of a glenoid surface. Section IV discusses apparatuses and methods for providing enhanced rotational position control during implantation of rotationally asymmetric glenoid components, such as in certain augmented glenoid components. Section V discusses low profile surgical guides for preparation of the glenoid. Low profile glenoid guides are configured to be less obstructive of other tools in the surgical field, such as retractors used to expose the joint space for procedures, and methods of using the same.

I. Glenoid Implant Positioning

Glenoid devices are implanted through an incision over the shoulder joint. The incision is enlarged with one or more retractors 16. The glenoid 18 is prepared through the enlarged incision to mate with an implant. Preferably the glenoid implant is oriented properly on the glenoid for a good joint replacement outcome. Patient specific techniques can enhance glenoid implant positioning.

A. Example Glenoid Implants

Figure 2:
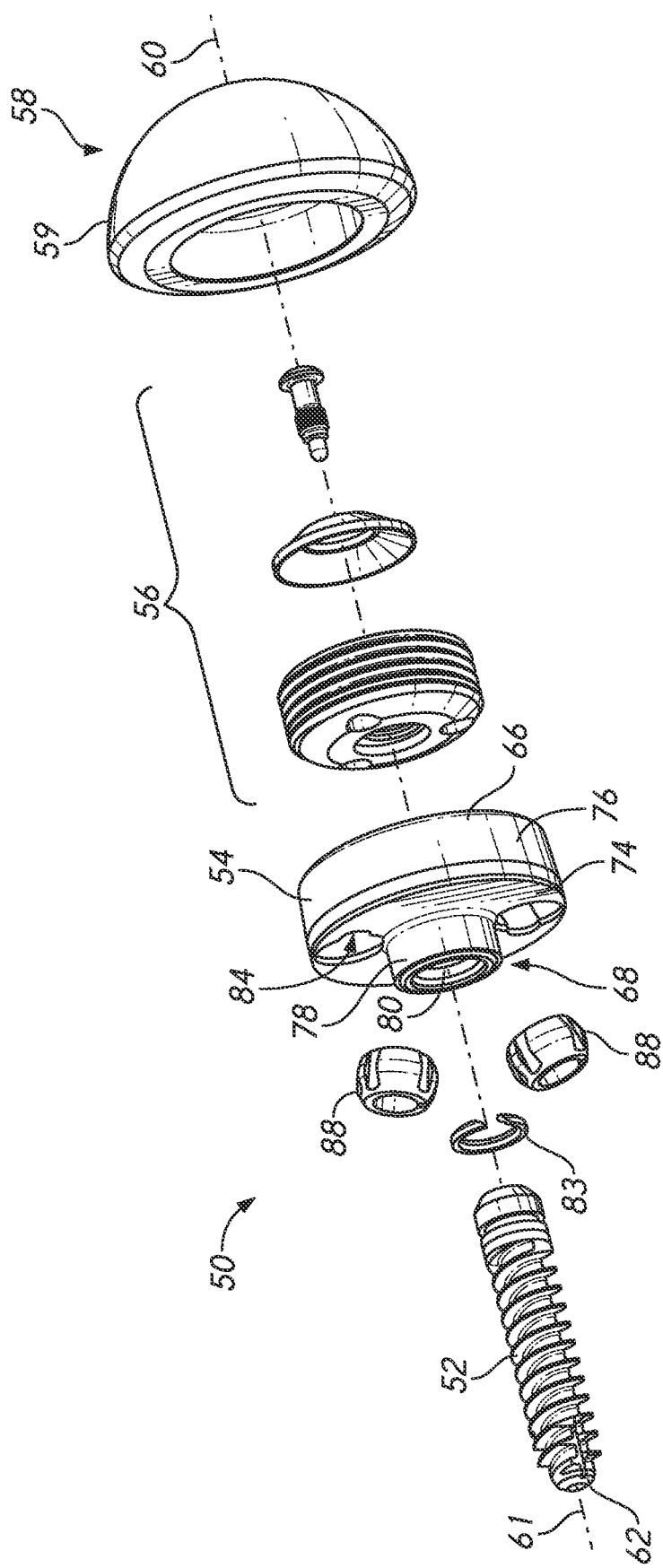
FIG. 2 is an exploded view of one embodiment of a reverse shoulder joint glenoid implant that includes a baseplate.

FIG. 2 illustrates a reverse shoulder glenoid implant 50. FIGS. 10 and 10A illustrate an augmented reverse shoulder implant 50A.

The glenoid implant 50 includes an anchor member 52 for anchoring the glenoid implant 50 in the glenoid, a baseplate 54, and a locking structure 56 that limits rotation between the anchor member 52 and the baseplate. The implant 50 also includes a glenosphere 58 that has an articular surface 59. The glenosphere 58 is couple to a concave humeral component anchored to the humerus of the shoulder joint to provide joint motion.

A longitudinal axis 60 is aligned with a central longitudinal axis 61 of anchor member 52. The glenosphere 58 is disposed toward a proximal end of the glenoid implant 50 along the longitudinal axis 60 and the anchor member 52 is disposed toward the distal end of the glenoid implant 50 along the axes 60, 61. An element of the glenoid implant 50 is proximal to another element if it is between the articular surface 59 and the other element and an element is distal to another element if it is between a distal tip 62 of the anchor member 52 and the other element. At some points below, reference may be made to the anatomical location. In use when the implant 50 coupled with a patient's scapula, the distal tip 62 is more medial on the patient, whereas the articular surface 59 of the glenosphere 58 is more lateral on the patient.

The baseplate 54 is oriented substantially perpendicular to the longitudinal axis 60 of the glenoid implant 50. The baseplate 54 has a proximal end 66 and a distal end 68. The proximal end 66 comprises a proximal surface and the distal end 68 comprises a distal surface, which can include a bone engaging surface 74. The bone engaging surface 74 is planar in some applications. FIG. 10A shows that a bone engaging surface 74A can comprise a more complex shape, such as a partial wedge shape in some applications. The bone engaging surface 74A can have a full wedge shape or another complex shape.

The baseplate 54 has a peripheral surface 76 between the proximal surface of the baseplate 54 and the bone engaging surface 74 of the baseplate 54. In some embodiments, the peripheral surface 76 is configured to form a Morse taper with the glenosphere 58. Further details of such mating and other variations can be found in US2015/0305877, which is hereby incorporated by reference in its entirety.

Figure 3:
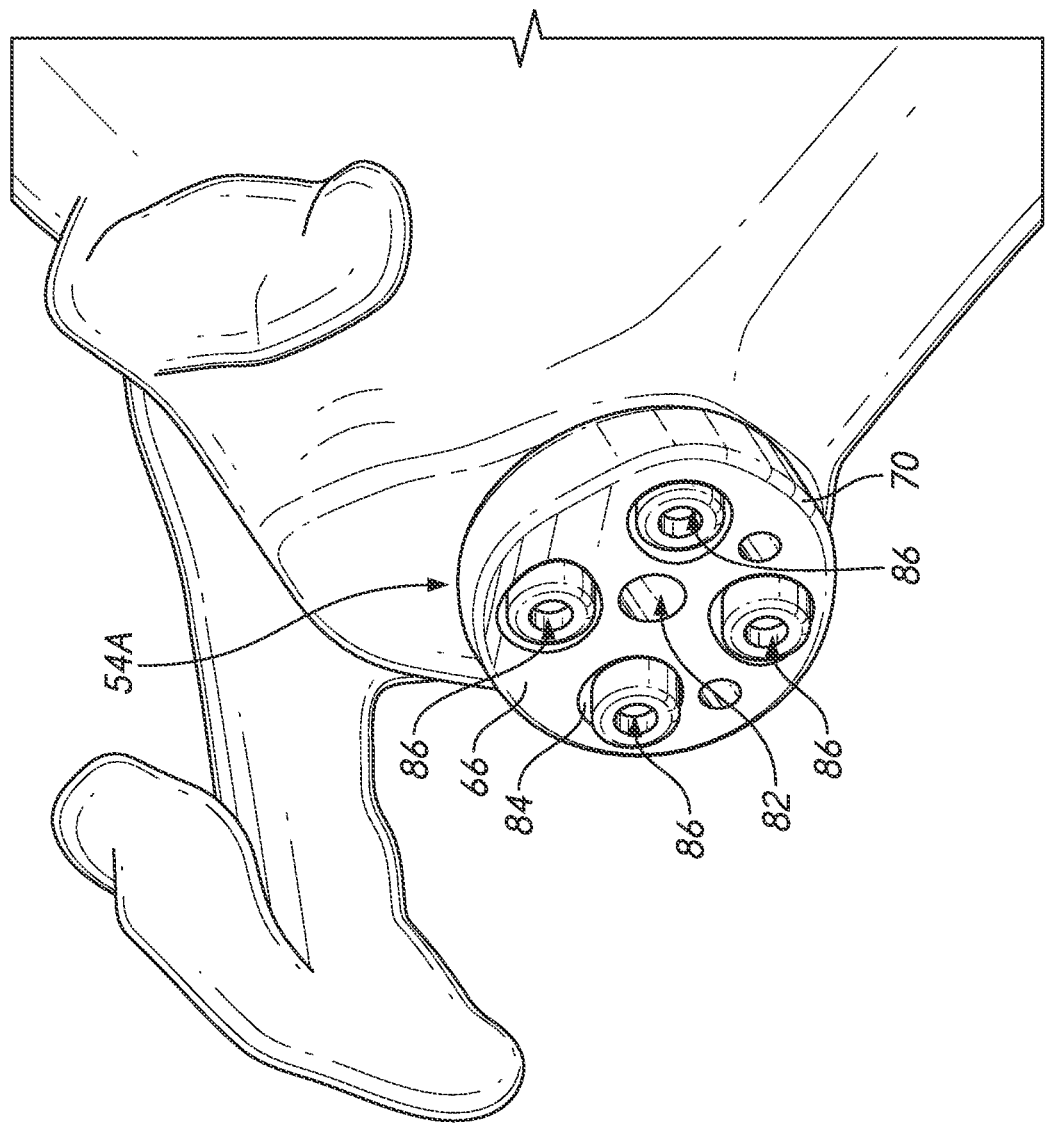
FIG. 3 shows a perspective view of another embodiment of a baseplate that can be used in the implant of FIG. 2 coupled with a glenoid surface.

The baseplate 54 has a central protrusion 78 that projects distally from the bone engaging surface 74 to the distal end 68. The central protrusion 78 has an outer surface that extends from the bone engaging surface 74 to a distal end of the baseplate 54. The central protrusion 78 can include a first aperture 80. The first aperture 80 can include a groove and a locking clip 83 to secure the anchor member 52 in the central protrusion 78. Further details of such securement and alternatives can be found in US2015/0305877, which is hereby incorporated by reference in its entirety. The baseplate 54, like the baseplate 54A (shown in FIG. 3), can have a second aperture 82 that extends from the first aperture 80 to the proximal end 66 of the baseplate 54. The second aperture 82 can extend continuously from the first aperture 80 but may be smaller in diameter than the first aperture 80.

The baseplate 54 and the baseplate 54A can include a plurality of peripheral holes 84 (e.g., two holes 84 as in FIG. 2 or four holes 84 as in FIG. 3) positioned laterally of the second aperture 82. The holes 84 are configured to accept peripheral anchors 86. The holes 84 extend from the proximal end 66 of the baseplate 54 to the bone engaging surface 74 of the baseplate 54. Members 88 disposed within the holes 84 in the baseplate 54 can be semi-spherical and can be surrounded by internal walls of the holes 84. The internal members 88 can allow for advancement of the anchors 86 relative to the baseplates 54, 54A and can later enlarge to create frictional connection therebetween preventing motion. The number and position of the holes 84 depends on many factors including the anatomical structure of the patient, the diameter of the peripheral anchors 86, and size constraints dictated by dimensions of the baseplate 54 or the baseplate 54A.

In various embodiments discussed further below surgical guides and methods using the same aid in aligning a wedge portion 394 of the baseplate 54A with a bone segment in need of augmentation.

B. Example of Sub-Optimal Orientation of the Glenoid Implant

Figure 4:
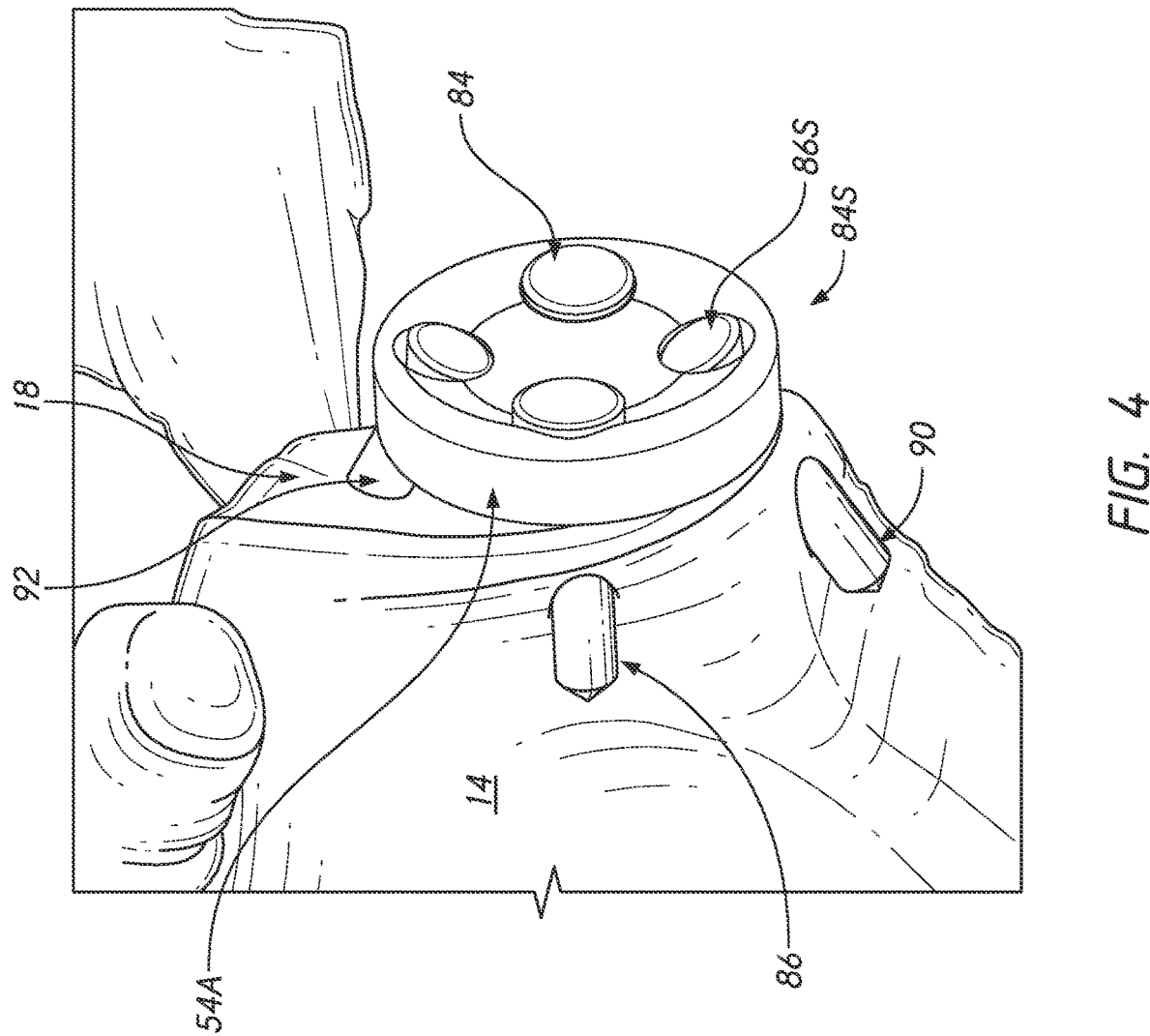
FIG. 4 shows a schematic representation of a baseplate similar to that of FIG. 3 that is not properly placed on the glenoid surface, resulting in anchors that couple the baseplate to the scapula protruding from the scapula.

FIG. 4 shows a sub-optimal placement of the baseplate 54A and the peripheral anchors 86. The baseplate 54A and the glenoid 18 to which it is attached are asymmetric. The amount a location of the mass of scapular bone to which the peripheral anchors 86 can be secured is not the same beneath each of the holes 84 located in the periphery of the baseplate 54A. Also, the baseplate 54A has an augmented portion that should be aligned with a portion of the glenoid 18 that is locally lower than other portions of the glenoid. FIG. 10A shows the augmented portion as a wedge portion 394 that extends partly across the bone engaging surface 74. Improper orientation of the baseplate 54A leads to poor screw engagement and gaps between the baseplate 54A and the glenoid 18. A sub-optimal orientation arises when a screw 86S disposed through a hole 84S that should be in a superior position on the glenoid 18 is in fact placed at an inferior position. This error positions the wedge portion 394 in the anterior position on the glenoid 18 when it is the posterior portion of the glenoid that would benefit from augmentation. This error causes an unacceptable gap between the glenoid 18 and an un-augmented portion of the bone engaging surface 74A. Also, the peripheral anchors 86 will not be seated well in the scapula 14. An excessive exposed distal length 90 of the anchor 86S extends out of the scapula 14 inferior to glenoid 18. An exposed length 92 of the peripheral anchor 86 in the superior position can be seen. The exposed length 92 would be minimal to non-existent if the baseplate 54A were properly placed because the bone engaging surface 74A should conform closely to the glenoid surface.

As discussed herein, improved surgical guides which can be patient specific can be used to reduce, minimize or prevent these sub-optimal outcomes in the implantation of the glenoid implant 50 and other glenoid implants and components thereof such as the baseplate 54 and the baseplate 54A.

II. Methods and Apparatuses for Enhanced Control of Bone Preparation and Implant Position FIGS. 5-9 illustrate methods for enhancing control of the placement of the baseplates 54, 54A of the glenoid implant 50, 50A. These methods can employ patient specific surgical guides to position peripheral guide pins and to form anchor channels in the glenoid

A. Guide for Forming Superior Peripheral Guide Channel

Figure 5:
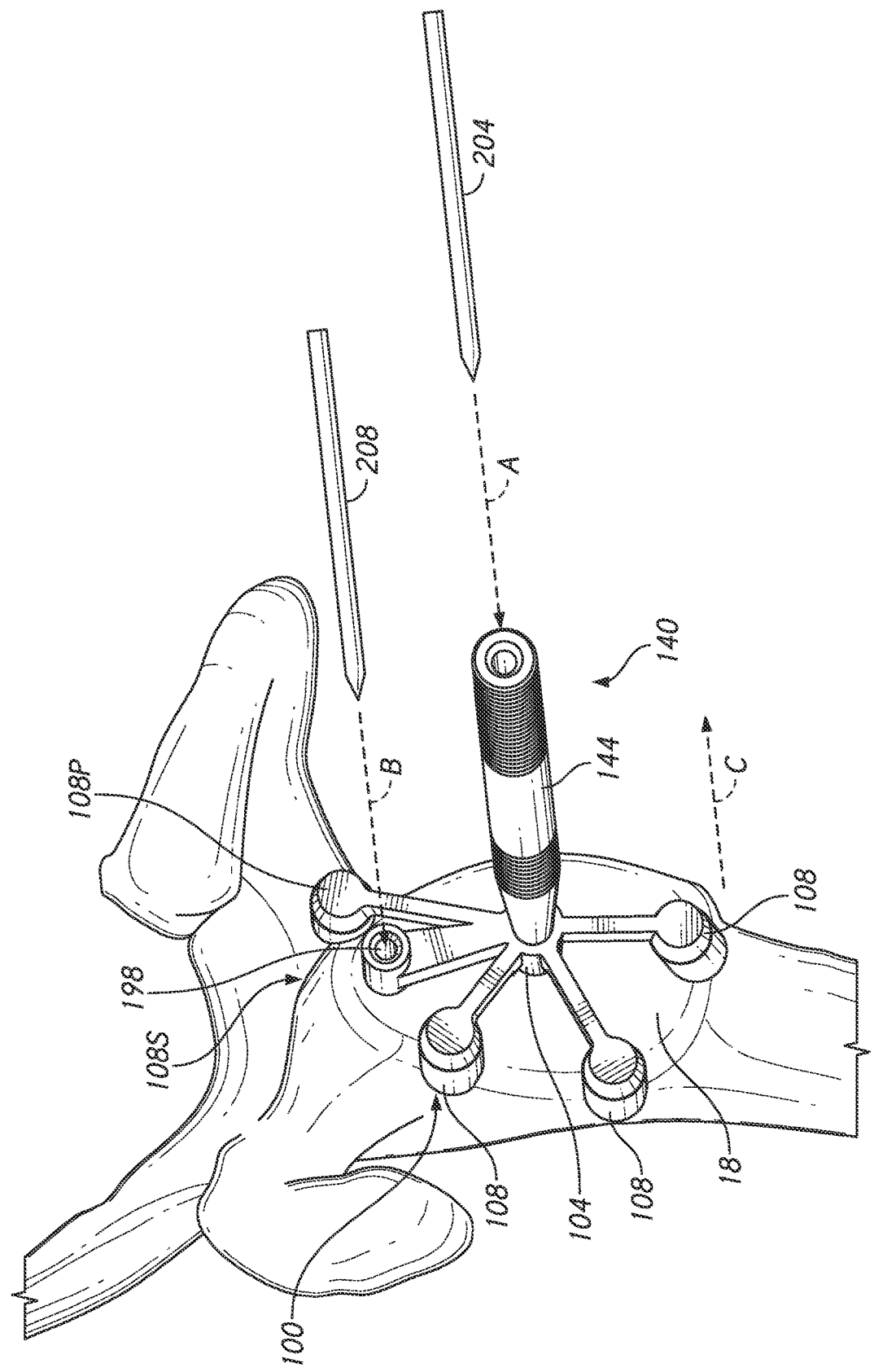
FIG. 5 shows the use of a patient specific glenoid guide in initial steps of a shoulder surgery method for placing guide pins to guide placement of anchors of a baseplate.

FIG. 5 illustrates steps of a shoulder surgery method following exposing of the glenoid 18. Once the glenoid 18 is exposed a patient specific shoulder guide 100 can be applied to, e.g., placed or secured to, a surface of the scapula 14. The patient specific shoulder guide 100 can be placed in contact with a portion of the glenoid 18, such as the glenoid rim. The patient specific shoulder guide 100 can be placed adjacent to the glenoid rim. The patient specific shoulder guide 100 can contact the glenoid rim and a portion of the scapula 14 outside the glenoid 18. The patient specific shoulder guide 100 can contact a portion of the scapula 14 outside the glenoid 18. The guide 100 can be coupled with the scapula 14 adjacent to the rim of the glenoid 18.

The guide 100 can be patient specific by having the gross dimensions thereof (e.g., height in the inferior-superior direction, width in the anterior-posterior direction) matching the size of a glenoid of or other portion of the scapula of a specific patient. The matching of the overall size of the guide and the forming of specific portions thereof to match a specific patient result from a pre-planning process for the guide, which is followed by a manufacturing process to make a specific guide for a specific patient, as discussed further below. The guide 100 can be patient specific in having one or more portions located centrally and peripheral members or legs that extend radially outward from the central portion, the length, width, and/or separation between the peripheral members being patient specific. The peripheral members or legs can also be patient specific in providing a contact portion for engaging in a patient specific manner a specific portion of the scapula of a specific patient. For example, the peripheral members or legs can have medial surfaces that are contoured to match, e.g., are complementary to or substantial negatives of, a segment of bone that can be selected by a surgeon or that can be identified by a process as providing optimal or enhanced fit for the guide 100. The contoured surfaces can have, for example, simple or complex shaped concavities that can be nested over similar or same shaped convexities of the bone, e.g., of the glenoid rim of the patient. When the contact surface or surfaces is or are coupled with the anatomy to which they were formed to match the guide 100 can provide further functions. For example, the central portion if provided can be coupled with the peripheral members or legs in a patient specific manner. For example, the central portion can be coupled with the peripheral members such that it is at a patient specific orientation or angle. The angle at which the central member is coupled can enable a channel therethrough to be at a patient specific orientation to enable a pin to be guided into a central portion of the glenoid whereby the pin can guide other instruments at a pre-planned patient specific trajectory. The configuration of the hub, peripheral members, contact surfaces, pin guide orientation or trajectory and other patient specific features can be generated using a processor and computing system implementing a method that takes as inputs one or more of pre-operative patient imaging, selection of bone portions to form contact surfaces in relation to, nature and type of implant to be applied to the patient following the surgery and other factors. More details of acquisition of pre-operative images or data and processing of the same into plans for making and the patient specific shoulder guide 100 are discussed in WO 2015071757 and WO 2015052586 which are hereby incorporated by reference herein.

Although the shoulder guide 100 generally is patient specific, it could be configured more generically in some embodiments. When patient specific, the shoulder guide 100 can be formed following acquisition of pre-operative imaging or data describing the actual bone anatomy of the patient to be treated. CT or MRI scan images or the like can be obtained, digitized and analyzed using software. The software is preferably combined with a manufacturing facility that allows the physical structures of the patient specific shoulder guide 100 to be made responsive to clinical judgements about the pre-operative images or data. The manufacturing facility can employ or include additive manufacturing such as three dimensional printing. Examples of three dimensional printing include direct metal laser sintering (DMLS), fused deposition modeling (FDM), fused filament fabrication (FFF), and electron beam melting (EBM). Any one or a combination of these or other additive manufacturing processes can be used in to manufacture the guide 100 or any of the other patient specific devices disclosed herein. In these processes a three dimensional object is formed by sequentially forming individual layers of the object on top of previously formed individual layers. These processes can closely control the gross dimensions of the object and also can form complex features and shapes such as contours. As discussed further below, these processes can be used to form and located the complementary surface on the guide such that the surface can mate with specific anatomy of a specific patient, e.g., concave surfaces that can nest on top of corresponding convex surfaces. More details of techniques for manufacturing of the patient specific shoulder guide 100 are discussed in WO 2015071757 and WO 2015052586 which are hereby incorporated by reference herein.

FIGS. 5 and 5A show that patient specific shoulder guide 100 includes a hub 104 and a plurality of peripheral members 108. The patient specific shoulder guide 100 includes a posterior portion 112 and an anterior portion 116. The posterior portion 112 and the anterior portion 116 of the guide 100 are configured to be positioned over posterior and anterior portions of the glenoid 18. The anterior portion 116 can have a greater number of peripheral members 108 than does the posterior portion 112. In the illustrated embodiment, the anterior portion 116 includes three peripheral members 108 and the posterior portion 112 includes one peripheral member 108. The patient specific shoulder guide 100 also has a peripheral member 108S in portion of the guide 100 configured to be oriented over a superior portion of the glenoid 18, hereafter the superior peripheral member 108S. The superior peripheral member 108S can be located between the posterior portion 112 and the anterior portion 116 of the guide 100. The spacing, size, and length of the peripheral members 108, 108S, 108P can be patient specific such that radially outer ends thereof will extend to anatomy to which they are preplanned to contact.

The hub 104 can have medial and lateral ends and a body that extends therebetween. The medial end faces the glenoid 18 when the guide 100 is mounted to the scapula 14. The medial end can be disposed adjacent to but may or may not contact the surface of the glenoid 18 when the guide 100 is mounted to the scapula 14. The lateral end of the hub 104 is located opposite the medial end of the hub 104. The lateral end of the hub 104 can be at the top side of the guide 100, e.g., an upper-most portion or at least a local top portion of the guide 100.

The patient specific shoulder guide 100 can have a central channel that extends through the hub 104. The central channel can extend from the lateral end to the medial end of the hub 104. The central channel of the hub first side 104 can be coupled with a pin guide 140 in some embodiments. In one embodiment, the central channel of the hub 104 has a tapered profile, e.g., a profile that is circular in cross-section and that has a larger diameter or circumference toward the lateral (proximal) end and a smaller diameter or circumference toward the medial (distal) end. The diameter or circumference can gradually but continuously decrease along a length between the lateral end and the medial end of the tapered profile. The diameter or circumference can decrease continuously from the lateral end toward the medial end of the tapered profile. The hub 104 can be formed or integrated into the guide 100 by the manner in which the hub connects to the peripheral members 108, 108S, 108P such that the orientation of the hub and the channel therethrough are oriented to a direction selected by the surgeon or by a process that identifies an optimal or otherwise appropriate direction.

FIG. 5 shows that the pin guide 140 can include a tubular body 144. The tubular body 144 can be cylindrical in form between proximal and distal ends. In some embodiments, a distal portion thereof is tapered to mate with the central channel of the hub 104. For example, a length of the tubular body 144 disposed at or adjacent to a distal end thereof can have a diameter or circumference that gradually but continuously increase from at or adjacent to the distal end toward the proximal end.

FIG. 5A shows that in one embodiment, the peripheral members 108 in the anterior portion 116 can have an inner end 160, an outer end 164, and an elongate member 166 disposed therebetween. The inner end 160 can be coupled with the hub 104. The outer end 164 can be disposed opposite the inner end 160. The outer end 164 can be disposed radially away from the inner end 160. At or adjacent to the outer end 164, the peripheral members 108 can include a patient specific contact surface 168. A patient specific contact member 172 can be disposed at the outer end 164 of each of the peripheral members 108. The patient specific contact member 172 can include a first end 176 and a second end 180. The first end 176 can be coupled to the outer end 164 of the elongate member 166. The second end 180 can be a free end of the patient contact member specific 172. The second end 180 can include the patient specific contact surface 168. The patient specific contact surface 168 is disposed on the underside (or medial side) of the guide 100. The patient specific contact surface 168 can be formed based on processing and analysis of pre-operative images or data of the scapula 14 and/or the glenoid 18 and can be formed in a manufacturing process that is directed by such analysis, such as by additive manufacturing as discussed in more detail above. FIG. 5A shows that one or more, e.g., all, of the peripheral members 108 in the anterior portion 116 can be configured to contact the rim of the glenoid 18. The patient specific contact surface 168 can have a shape that corresponds to, e.g., is complementary to and that can be a negative of the natural contours of the glenoid 18 including being shaped to mate to osteophyte or other natural bony structures in a unique position or orientation.

FIG. 5A shows that one or more of the peripheral members 108 residing in the posterior portion 112 can include one of the peripheral members 108 that is configure to provide patient specific interaction in the posterior portion 112. The peripheral member 108 in the posterior portion 112 can be similar to the peripheral members 108 in the anterior portion 116 except as described differently below. The peripheral members 108 in the posterior portion 112 can advantageously be configured to reduce or minimize obstruction of the surgical field in the posterior portion 112. For example, the peripheral member 108 of the posterior portion 112 can extend to a superior portion of the glenoid rim. A peripheral member 108P in the posterior portion 112 can be configured for patient specific mating in a region of the scapula 14 located on, around, adjacent to, or even outside of the rim of the glenoid 18. This leaves a large uninterrupted portion of the rim of the glenoid 18 beneath the posterior portion 112 unobstructed. The elongate member 166P can be longer than the elongate member 166 of the peripheral members 108 disposed in the anterior portion 116 of the patient specific shoulder guide 100 such that the peripheral member 108P can extend to the superior portion Su of the glenoid rim. The posterior portion 112 can be configured with a large unobstructed region 188. The unobstructed region 188 can include an angle of 45 degrees or more. The unobstructed region 188 can include an angle of 90 degrees or more. The unobstructed region 188 can include an angle of 120 degrees or more. The unobstructed region 188 can include an angle of 175 degrees or more.

Other approaches to making the patient specific shoulder guide 100 low profile in the posterior portion 112 are discussed below, including making at least a portion of the peripheral members 108 in the posterior portion 112, e.g., the elongate member 166P, with a lower height than the height of the peripheral members 108 in the anterior portion 116. FIGS. 20-26B show a number of other guides, the descriptions of which are relevant to and can supplement the description of the guide 100. For example at least a portion of the guide 100, including one or all of the peripheral members 108 and/or the hub 104 can be low profile to allow for improved access of other instruments in the surgical field.

The patient specific shoulder guide 100 includes a guide feature 192 coupled with the hub 104. The guide feature 192 includes an inner end coupled with the hub 104 an outer end disposed away from the inner end of the guide feature 192. The guide feature 192 includes an aperture 198 disposed at or adjacent to the outer end thereof. The aperture 198 can be used to secure the guide 100 against rotation, e.g., rotation about the longitudinal axis through the hub 104, when the guide 100 is applied to the patient. Other guides herein with peripheral apertures also can use the peripheral apertures to secure such other guides against rotation. The guide feature 192 can be configured as the peripheral member 108S, e.g., can be located at a position of the patient specific shoulder guide 100 such that when the patient specific shoulder guide 100 is properly placed on the scapula 14, e.g., on the glenoid 18 the aperture 198 is positioned at an appropriate position superior to the glenoid 18 to control aspects of methods that follow the stage depicted in FIG. 5. The peripheral member 108S need not be in direct contact with the glenoid 18 and can be spaced apart from the glenoid when the guide 100 is applied to the glenoid. The peripheral member 108S can in various alternative embodiments have a portion in contact, e.g., in patient specific contact, with the scapula 14. In one embodiment a lower portion of the peripheral member 108S is spaced from the scapula 14 when the guide 100 is mounted to the scapula. The aperture 198 can have a trajectory that is patient specific. For example, the aperture 198 can be aligned to an axis therethrough that is perpendicular to a plane to which the glenoid 18 is to be reamed. In some methods as discussed below, the glenoid 18 is reamed to a single plane. In some methods, the glenoid 18 is reamed in a manner having a more complex shape, e.g., with two, three, four or more than four portions that are not coplanar. One method provides two planar regions on the glenoid 18 that meet at a boundary within the glenoid 18. The aperture 198 has a trajectory that is perpendicular to one of these planes.

FIG. 5 shows that after the patient specific shoulder guide 100 has been placed and the pin guide 140 mated with the hub 104, a central guide pin 204 and a peripheral guide pin 208 can be advanced into the scapula 14. The central guide pin 204 can be advanced as indicated by the arrow A into the tubular body 144. The central guide pin 204 can be directed into the glenoid 18, e.g., into a central region of the articular surface thereof. The peripheral guide pin 208 can be advanced as indicated by the arrow B through the aperture 198 of the peripheral member 108S. The peripheral guide pin 208 can be directed into a superior region of the glenoid 18, e.g., a portion of the articular surface of the glenoid 18 just inward of the glenoid rim. In other methods, the peripheral guide pin 208 can be directed into the glenoid rim. In other methods, the peripheral guide pin 208 can be directed into a region of the scapula 14 outside the glenoid rim. The guide pin 208 can be placed into any portion of the scapula 14 outside of the surface to be reamed, including generally superior of, generally anterior of, generally posterior of or generally inferior of a surface to be reamed or otherwise prepared in a subsequent step. As discussed in connection with the guide 1000 of FIG. 27A and with the guide 1050 of FIG. 28A, a mark on the bone or the guide pin 208 in the bone can be placed through a channel 1010 in the guide 1000 or a channel 1060 in the guide 1050. The channel 1010, 1050 is disposed at a position relative to the portion of the glenoid to receive the most augmentation, e.g., 180 degrees offset therefrom. The mark can provide for visual guidance of instruments, e.g., one or more of a reamer or an implant driver as discussed more fully below. The pin 208 can provide for direct sliding guidance of instruments, e.g., one or more of a reamer or an implant driver as discussed more fully below. The central guide pin 204 and the peripheral guide pin 208 can be a conventional orthopedic guide pin such as a Steinmann pin or a K-wire or similar structure. The central guide pin 204 may be longer than the peripheral guide pin 208 depending on the use in relevant methods, some of which are discussed in detail below. The central guide pin 204 and the peripheral guide pin 208 are examples of central and peripheral guide features that can be used in various methods herein.

The use of the superior peripheral member 108S to place the pin 208 can advantageously be applied to other guides described herein, such as the guides of FIGS. 20-26B.

Figure 6:
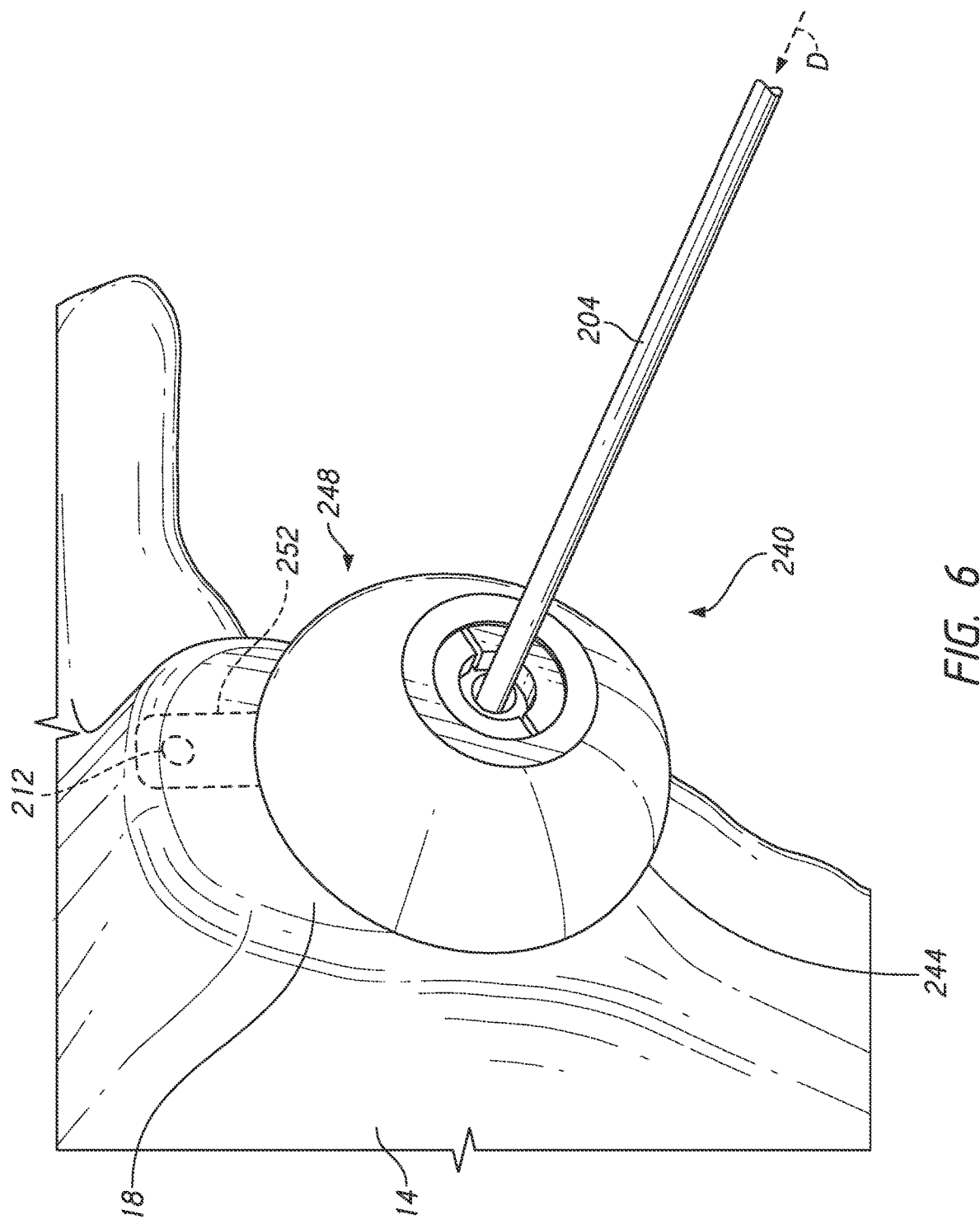
FIG. 6 shows methods of sizing a glenoid over a central guide pin extending away from a central region of a glenoid surface, the guide pin having been placed with reference to the patient specific glenoid guide of FIG. 5.
Figure 7:
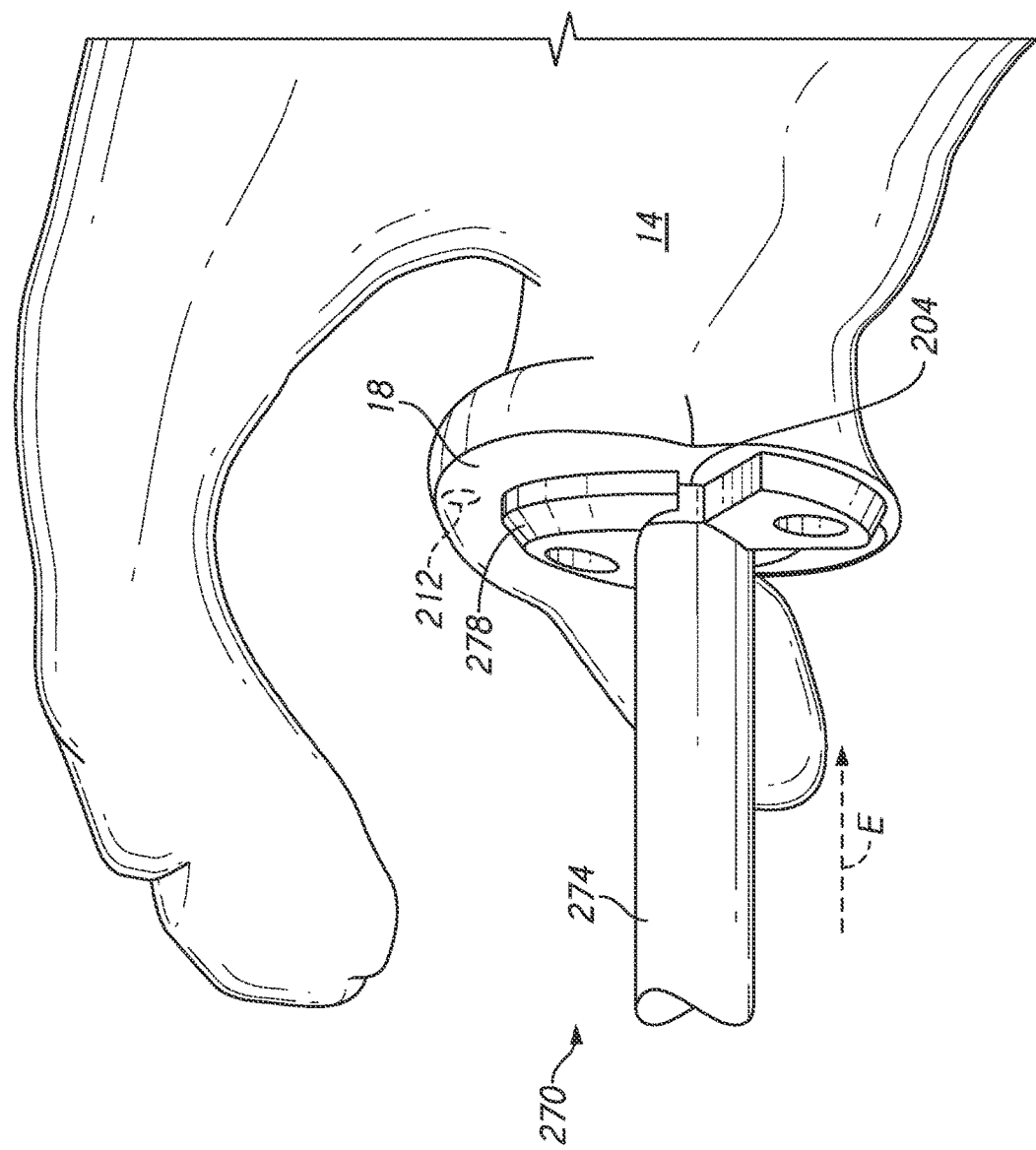
FIG. 7 shows methods of reaming with reference to the central guide pin shown in FIG. 6 which had been placed with reference to the patient specific glenoid guide of FIG. 5.
Figure 12:
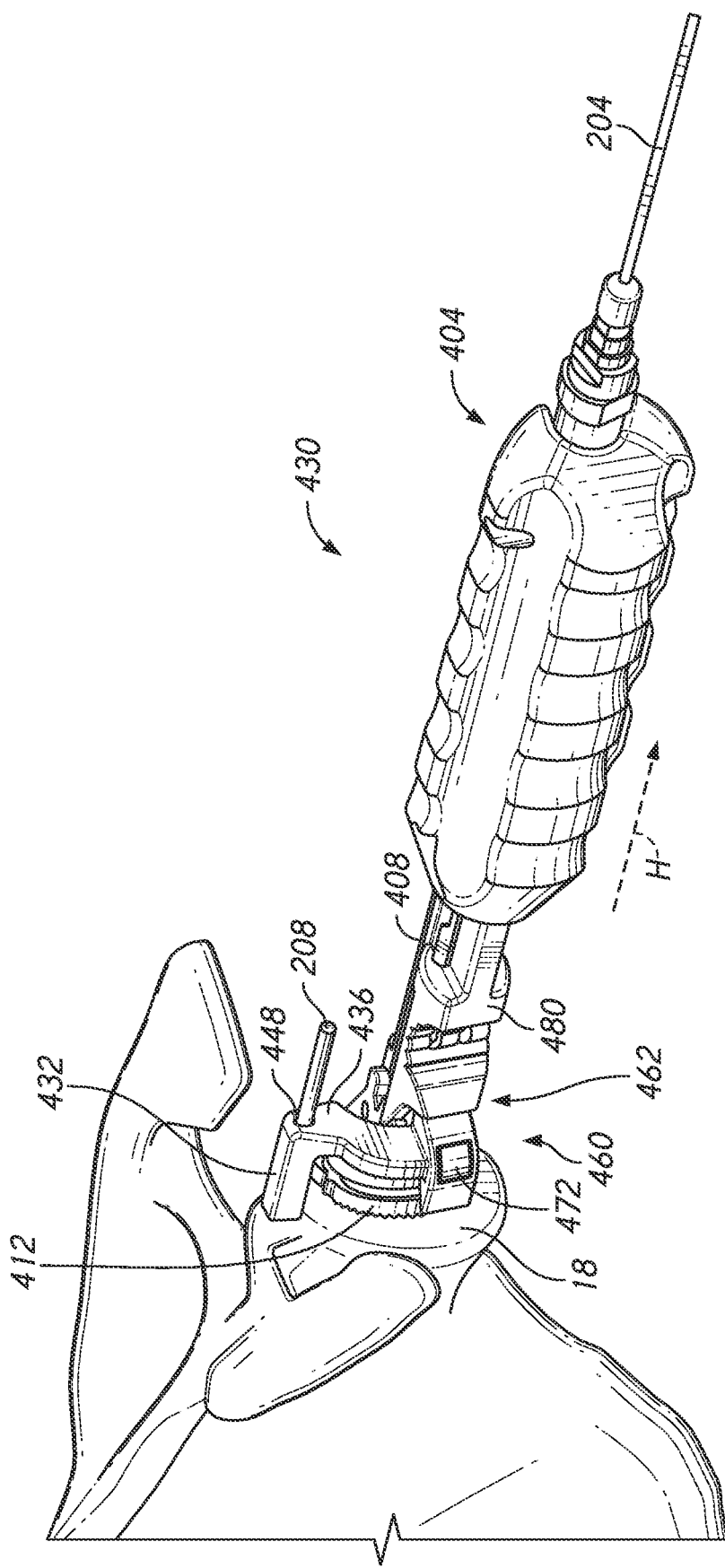
FIG. 12 illustrates further methods of reaming a glenoid surface by reference to a peripheral guide pin placed using the patient specific glenoid guide of FIG. 5.

FIGS. 6, 7, and 12 show that other guide features can be used in other methods as discussed herein. For example, the aperture 198 can be used to direct the peripheral guide pin 208 into the scapula 14 to form a peripheral aperture 212 in the scapula 14. A drill, punch or other channel forming tool can be directed into the scapula 14 through the aperture 198 to form the peripheral aperture 212 in the scapula 14. The peripheral aperture 212 can extend into the scapula 14 a sufficient distance to receive in a later part of a various methods the peripheral guide pin 208, a peg or other guide member or reference device.

In one variation, one of the central guide pin 204 and the peripheral guide pin 208 is placed using the patient specific shoulder guide 100. The guide 100 can be used to form the peripheral aperture 212 or another guide feature but not to place the peripheral guide pin 208 initially. After the central guide pin 204 and/or the peripheral guide pin 208 are placed or after the peripheral aperture 212 or a central aperture are formed or other reference provided in the glenoid 18 the patient specific shoulder guide 100 can be removed from the glenoid 18 as indicated by the arrow C. The patient specific shoulder guide 100 and the pin guide 140 can be removed together through the incision (not shown) which is provided in the tissue over the glenoid 18 to provide access to the glenoid as discussed above. The patient specific shoulder guide 100 and the pin guide 140 can be removed over the central guide pin 204 which may be sufficiently long to extend out of the proximal end of the tubular body 144 and out of the incision in some cases. In another method, the pin guide 140 is decoupled from the patient specific shoulder guide 100 and is removed first along the direction indicated by the arrow C. After the pin guide 140 is removed, the patient specific shoulder guide 100 is removed along the direction indicated by the arrow C. If the peripheral aperture 212 is formed and a corresponding central aperture is formed through the tubular body 144 or the hub 104 the pin guide 140 and the patient specific shoulder guide 100 can be removed in an unguided manner.

FIG. 6 shows a further step of determining the size of the glenoid 18 after the central guide pin 204 has been inserted and the peripheral aperture 212 has been formed. A sizer 240 can be advanced along the central guide pin 204 in a direction indicated by the arrow D from a proximal end thereof (not shown) to adjacent to the glenoid 18. The sizer 240 can include an outer periphery 244 that has a diameter that matches the anterior to posterior dimension of the glenoid 18. The sizer can have indicia 248 that correspond to a suitable size of the baseplate 54 or the baseplate 54A. In another method, the peripheral guide pin 208 is retained in the scapula 14. The patient specific shoulder guide 100 is removed by sliding it proximally over the peripheral guide pin 208. The patient specific shoulder guide 100 can be removed by sliding it proximally over the central guide pin 204 and at the same time over the peripheral guide pin 208. FIG. 6 shows that the sizer 240 can be configured to be advanced over the central guide pin 204 without contacting the peripheral guide pin 208. One approach to providing this capability is to configure the peripheral member 108S to extend a distance greater than the width of the glenoid 18 so that outer periphery of the sizer 240 does not extend to the peripheral aperture 212.

If the peripheral guide pin 208 is provided as illustrated in FIG. 5, the sizer 240 can be modified to be advanced over the peripheral guide pin 208 rather than over the central guide pin 204. For example, the sizer 240 can be generally circular as shown but can have a projection 252 on one side that extends at least to the location of the peripheral aperture 212. The projection 252 can be positioned on a superior side of the sizer 240 if the sizer 240 is asymmetric other than the presence of the projection 252. The projection 252 can be positioned relative to the indicia 248 such that the indicia are upright when the projection 252 is on the peripheral guide pin 208 or mated with the peripheral aperture 212. The projection 252 can be mated with the peripheral aperture 212 by providing a peg or other projection disposed on a lower portion thereof. The use of a peg to mate with the peripheral aperture 212 is discussed below in connection with FIGS. 14-16B, which concept is fully applicable to the projection 252 of the sizer 240. By engaging the sizer 240 with the guide pin 204 and with the aperture 212 or the pin 208 the sizer can be aligned with a direction of the glenoid 18, such as anterior-posterior or inferior-superior.

Because the patient bony anatomy is characterized by CT or scan images or the like pre-operatively, using the sizer 240 to confirm the size the glenoid 18 and/or to pick an appropriate baseplate 54 or baseplate 54A is optional or can be merely confirmatory. In some embodiments, the step illustrated in FIG. 6 is not needed. If used, the sizer 240 is thereafter removed in a direction opposite the direction indicated by the arrow D over the central guide pin 204 and/or over the peripheral guide pin 208.

FIG. 7 shows that before or after determining or confirming the size of the glenoid 18 or the appropriately size for the baseplate 54 or the baseplate 54A the natural articular surface of the glenoid 18 can be modified, e.g., can be reamed. In one method a cannulated reamer 270 is provided. The cannulated reamer 270 has a channel therethrough that can be inserted over the central guide pin 204. The cannulated reamer 270 can be advanced over the central guide pin 204 to the surface of the glenoid 18. The cannulated reamer 270 can be rotated to move cutting features thereof over the glenoid 18. Further medially directed motion toward or pressure on the glenoid 18 (e.g., in the direction indicated by the arrow E) will result in a small amount of bone removal to provide a controlled, e.g., planar surface. The reamer can take any suitable form but preferably includes a stationary outer sheath 274, a rotatable cutting head 278 and a lumen to receive the central guide pin 204. An internal drive shaft (not shown) coupled with the cutting head 278 can rotate within the outer sheath 274 to provide safe control cutting action at the cutting head 278 without harming other structures in the surgical field. After the surface of the glenoid 18 has been prepared to mate with the baseplate 54, the reamer 270 can be removed from the central guide pin 204 in a direction opposite that of the arrow E.

As discussed below in connection with FIG. 11, the cannulated reamer 270 can be exchanged for another reamer configured to create more complex geometries at the surface of the glenoid 18. A rotation control device can be provided for reamers that are configured to ream a glenoid surface asymmetrically, as discussed below in connection with FIGS. 12-16B. Asymmetrical reaming can prepare the glenoid 18 for the baseplate 54A as discussed further below.

Figure 8:
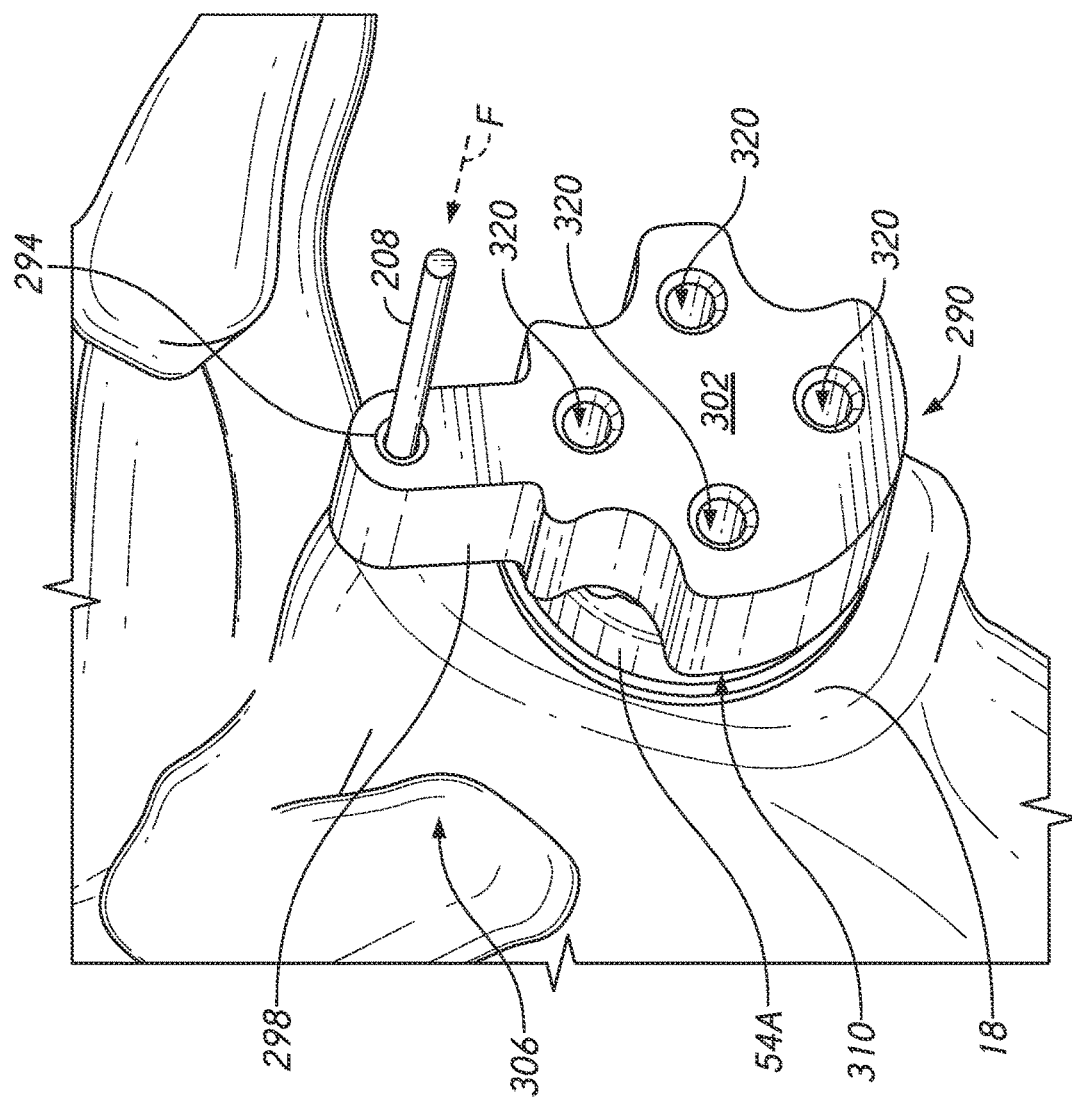
FIG. 8 shows a method of advancing an anchor trajectory guide over a peripheral guide pin to a location adjacent to a glenoid surface, the anchor trajectory guide adapted to form a peripheral anchor channel in the scapula, the peripheral guide pin placed using the patient specific glenoid guide of FIG. 5.

B. User of Peripheral Guide Feature to Control Formation of Peripheral Anchor Channels FIG. 8 shows a step of a method that can follow removal of the cannulated reamer 270 from the glenoid 18. The peripheral guide pin 208 can be disposed in the peripheral aperture 212 in a superior location. In one method, reaming as in FIG. 7 is conducted without the peripheral guide pin 208 being present. For such a method, the peripheral guide pin 208 can be placed after the reaming is complete. In other methods, the peripheral guide pin 208 is present during reaming and may be used to control the position of the reamer 270 on the face of the glenoid 18.

The peripheral guide pin 208 is used to control the position of an anchor trajectory guide 290 in one embodiment. The anchor trajectory guide 290 has an aperture 294 that can be advanced over the peripheral guide pin 208 along a medial direction, as indicated by the arrow F. The aperture 294 can be disposed through a projection 298 of a body 302 of the anchor trajectory guide 290. The body 302 can have a first side configured to face toward a glenoid surface in use and a second side opposite the first side. The projection 298 of the anchor trajectory guide 290 can comprise part of a superior portion 306 of the body 302 of the anchor trajectory guide 290. An inferior portion 310 of the body 302 of the anchor trajectory guide 290 can include one or more, e.g., a plurality of, peripheral screw apertures 320.

Figure 8A:
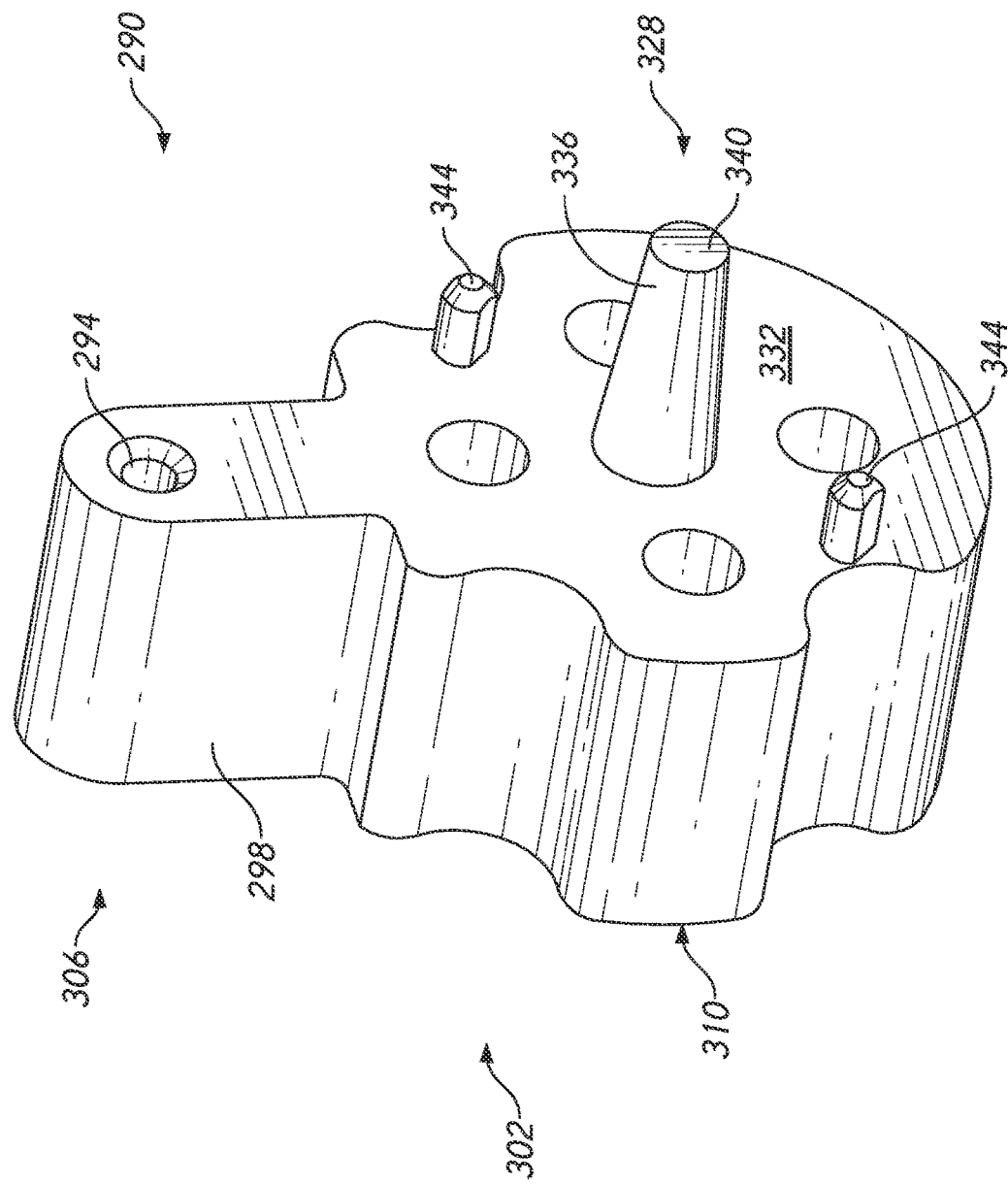
FIGS. 8A-8E show details of the anchor trajectory guide of FIG. 8, alone and in combination with a baseplate, the anchor trajectory guide adapted to form peripheral anchor channels in the scapula to assure good purchase in the bone for a specific patient.
Figure 8B:
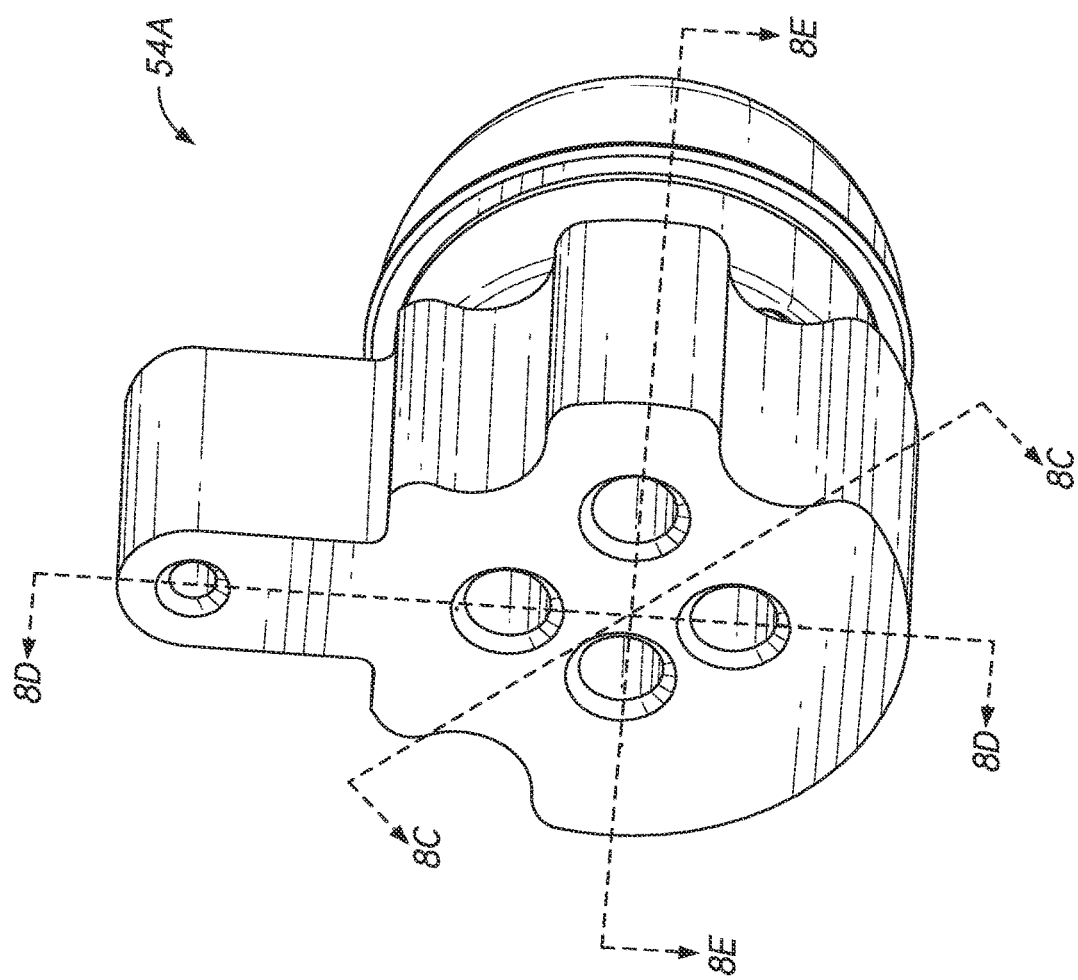
Figure 8C:
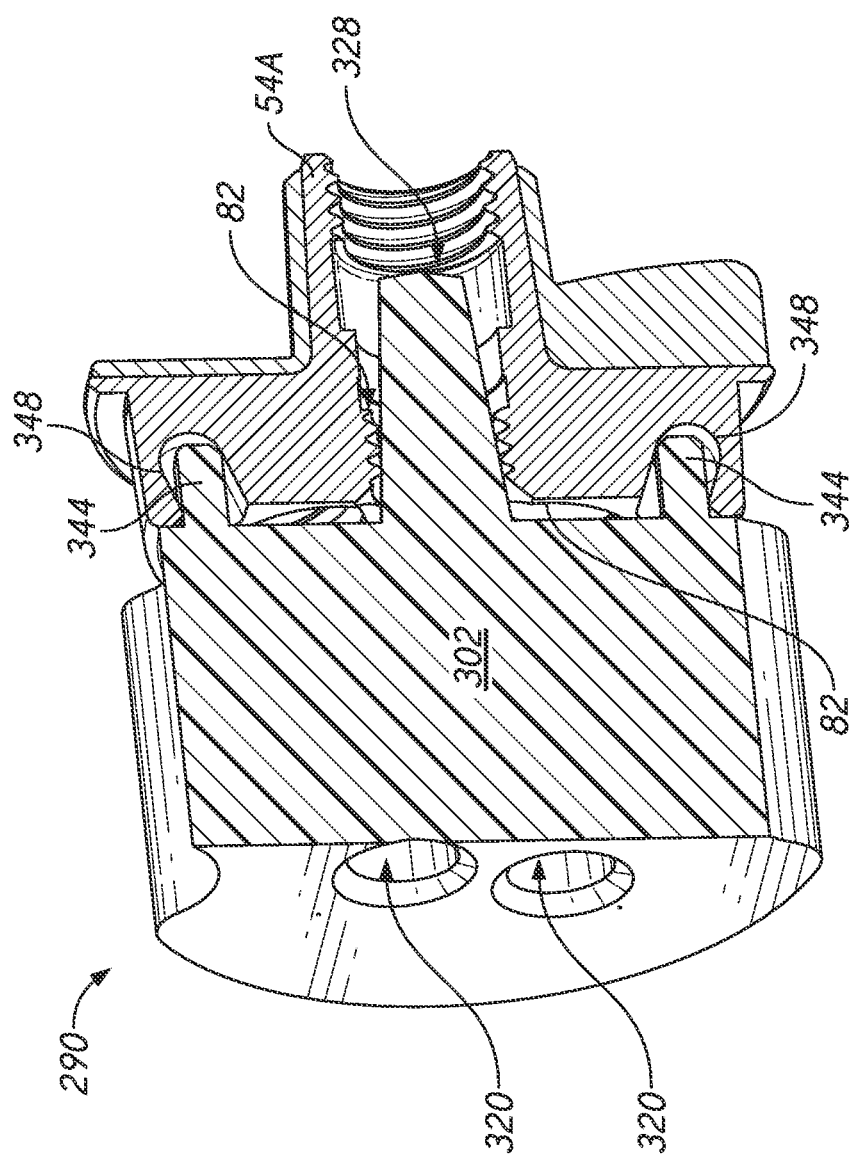
Figure 8D:
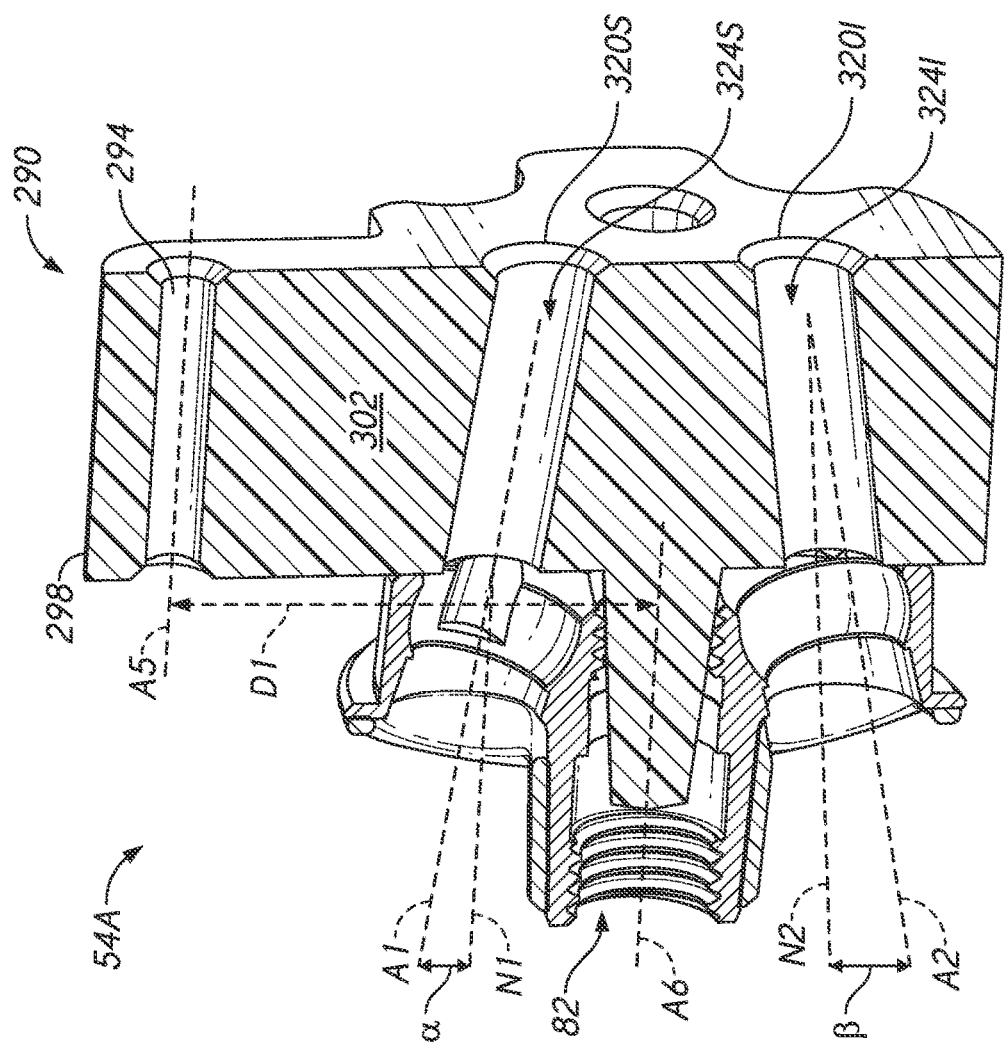

FIGS. 8A-8C show further details of the anchor trajectory guide 290. The anchor trajectory guide 290 can be patient specific, e.g., manufactured for a particular patient. As discussed, the bone around the glenoid 18 is not symmetric and can be highly irregular. CT scan images or the like can direct the manufacturing of some or all portions of the body 302 of the anchor trajectory guide 290 to a specific patient. In particular, based on a patient's shoulder anatomy and geometry, an anchor trajectory guide 290 can be manufactured that is complementary to the patient's specific anatomy. The manufacturing of the anchor trajectory guide 290 can be accomplished using additive manufacturing techniques to be specifically configured to be complementary to the patient's specific anatomy. For example, a distance D1 from a central axis A5 of the aperture 294 to a central axis A6 of the aperture 82 of the baseplate 54 or the baseplate 54A when coupled with the guide 290 can be configured to suit a specific patient so that the distance from the peripheral aperture 212 to the entry point of a peripheral anchor 86 placed at the superior location will be as predetermined. Also, an angle α of a central longitudinal axis A1 of the channel 324S to normal axis N1 perpendicular to a medial or lateral side of the body 302 defines a bone channel extending to the entry point on the glenoid 18 into the scapula 14 and medially therefrom. A drill or punch following the channel 324S will define a pathway that will provide a good outcome as discussed below in connection with FIG. 9. The channel 324S will be generally in a medial and superior direction (from the perspective of use when mounted as shown in FIG. 8). The medial end of the channel 324S will be medial and generally superior of the lateral end of the channel 324S.

Similarly the inferior peripheral screw aperture 320I is positioned on the body 302 of the anchor trajectory guide 290 to enable the inferior peripheral screw aperture 320I to direct a drill, a punch or similar tool to form a channel in the glenoid 18. The inferior peripheral screw aperture 320I can provide access to a channel 324I disposed through the body 302. The channel 324I defines a central longitudinal axis A2 along which the drill or punch can be directed. The central longitudinal axis A2 can be oriented in a patient specific manner, e.g. along an angle β relative to the normal axis N2. The angle β is selected such that the trajectory directed through the body 302 and through the baseplate 54A causes the peripheral anchors 86 to reach cortical bone through the cancellous bone beneath the glenoid 18 but not to protrude therefrom or to protrude only a prescribed amount for a specific patient.

Figure 8E:
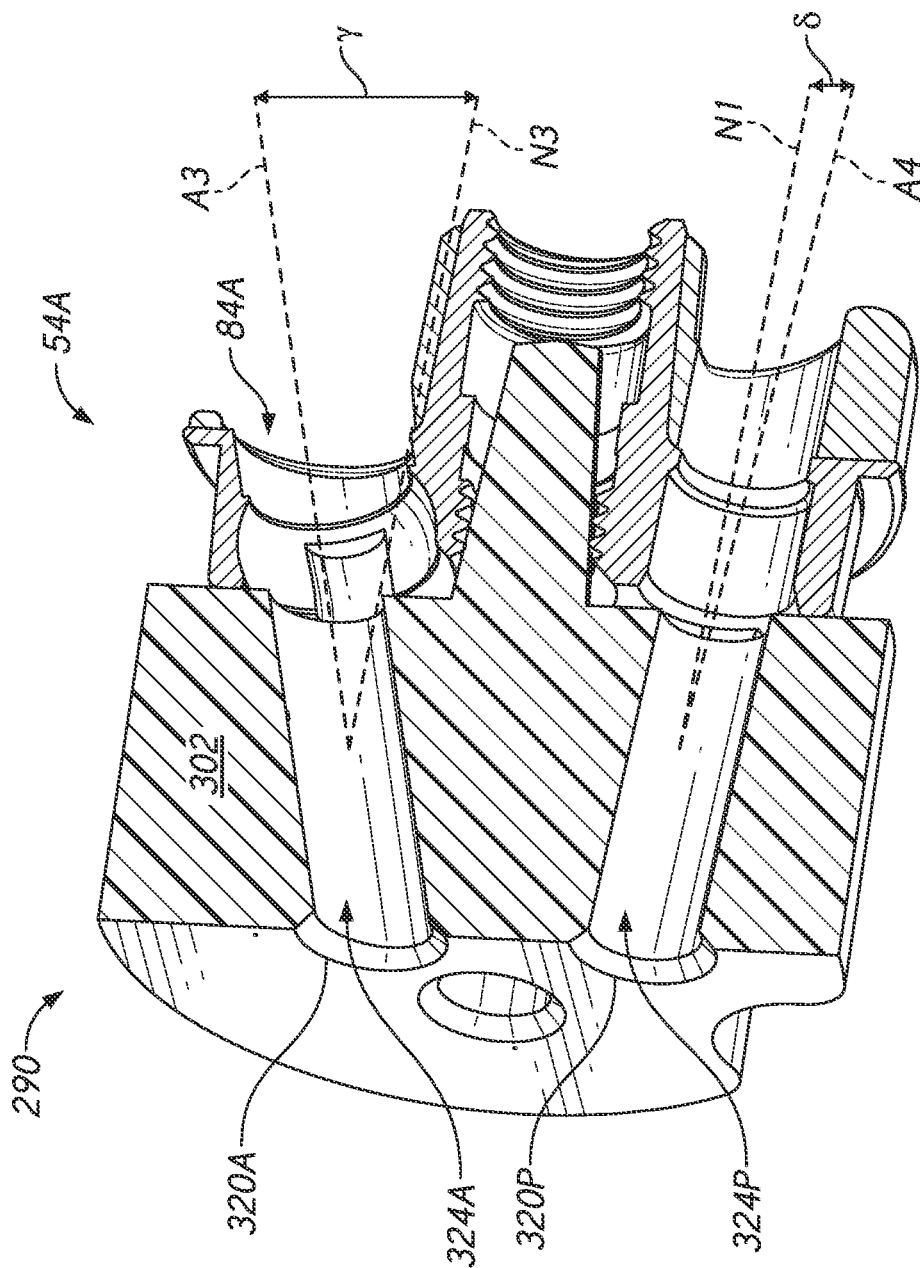

FIG. 8E shows further details of the anchor trajectory guide 290 including patient specific configurations of peripheral screw apertures 320. An anterior peripheral screw aperture 320A and a posterior peripheral screw aperture 320P can be provided each of which can be patient specific. The anterior peripheral screw aperture 320A can open to a channel 324A that is oriented at an angle γ relative to a normal axis N3. The posterior peripheral screw aperture 320P can open to a channel 324P that is oriented at an angle δ relative to a normal axis N4. The angles γ and δ can be different from each other and can be patient specific. The angle δ can be smaller than the angle γ. The angle δ is configured such that the axis A4 extends through the augmented part of the baseplate 54A. The angle γ can be configured such that a screw directed along a central longitudinal axis A3 of the channel 324A extends through the holes 84A of the baseplate 54A on a side opposite the bone engaging surface 74A.

FIG. 8 shows that in one embodiment the anchor trajectory guide 290 can support the baseplate 54A in contact with the glenoid 18. FIGS. 8A and 8C show more details of one embodiment for holding the baseplate 54A in place on the anchor trajectory guide 290. FIG. 8A shows that the anchor trajectory guide 290 can include a central projection 328 disposed on a distal side 332 of the body 302. The distal side 332 is a first side of the body. The projection 328 is configured to be received in a recess of a glenoid baseplate to facilitate positioning the baseplate at the same time the screw guide is positioned to form peripheral screw channels. The central projection 328 can include an elongate body 336. In one embodiment, the elongate body 336 is tapered between the distal side 332 of the body 302 and a distal end 340 of the elongate body 336. The tapered profile of the elongate body 336 provides one convenient manner of coupling the anchor trajectory guide 290 with the baseplate 54A. The distal end 340 can be smaller in diameter than the second aperture 82. As such the second aperture 82 can be easily inserted over the elongate body 336. The diameter of the elongate body 336 adjacent to the distal side 332 can be larger than the diameter of the second aperture 82. In one approach an interference fit can be achieved between the anchor trajectory guide 290 and the baseplate 54A at a location along the length of the elongate body 336. In one approach the anchor trajectory guide 290 and the baseplate 54A is configured with a slip fit to the elongate body 336.

In addition, one or a plurality of peripheral members 344 can be provided on the distal side 332 of the body 302. The members 344 are peripheral in that they are disposed in positions generally anterior and posterior to the protrusion 328, which is central compared to the position of the members 344. The members 344 are circumferentially between adjacent screw apertures 320 and in some cases are radially farther from the projection 328 than are the apertures 320. The members 344 can be offset in superior and inferior directions from each other. If an anterior-posterior line intersecting the projection 328 is provided, one of the members can be seen to be disposed inferior to this line and one can be seen to be disposed superior to this lien in one embodiment. Each of the peripheral member(s) 344 can be configured to be received in a corresponding tooling interface 348 on the lateral side of the baseplate 54A. The engagement of the peripheral members 344 with the tooling interface 348 assures that the baseplate 54A and the anchor trajectory guide 290 can be coupled along a specific axis. The members 344 facilitate positioning the baseplate 54A. The baseplate 54 is rotationally symmetrical so the baseplate 54 can be coupled in one of two rotational positions or at any rotational position. The baseplate 54A is asymmetric in one embodiment where the wedge portion 394 is provided. The baseplate 54A is oriented such that the wedge portion 394 is aligned with a location of the glenoid 18 to be augmented. The baseplate 54A is then coupled with the anchor trajectory guide 290. The baseplate 54A and the anchor trajectory guide 290 can then be mounted to the peripheral guide pin 208. In one patient wear pattern, the portion to be augmented is the posterior portion of the glenoid 18. The baseplate 54A is asymmetric so that the baseplate 54A is attached in the orientation in which the wedge portion 394 is aligned with a posterior side of the anchor trajectory guide 290 (e.g., to the right as viewed from the lateral side for a left shoulder and to the left as viewed from the lateral side for a right shoulder).

In a different approach, the baseplate 54A is held in place on the glenoid 18 and the anchor trajectory guide 290 is aligned with the baseplate 54A and then mounted thereto or separately supported.

A drill or punch can be directed through each one of the peripheral screw apertures 320 and when so directed can also be direct through the holes 84A of the baseplate 54A. When so directed channels or pilot holes are formed in the scapula 14 from the reamed surface of the glenoid 18. The channels or pilot holes control the trajectory of the peripheral anchors 86 that are advanced through the holes 84.

Figure 9:
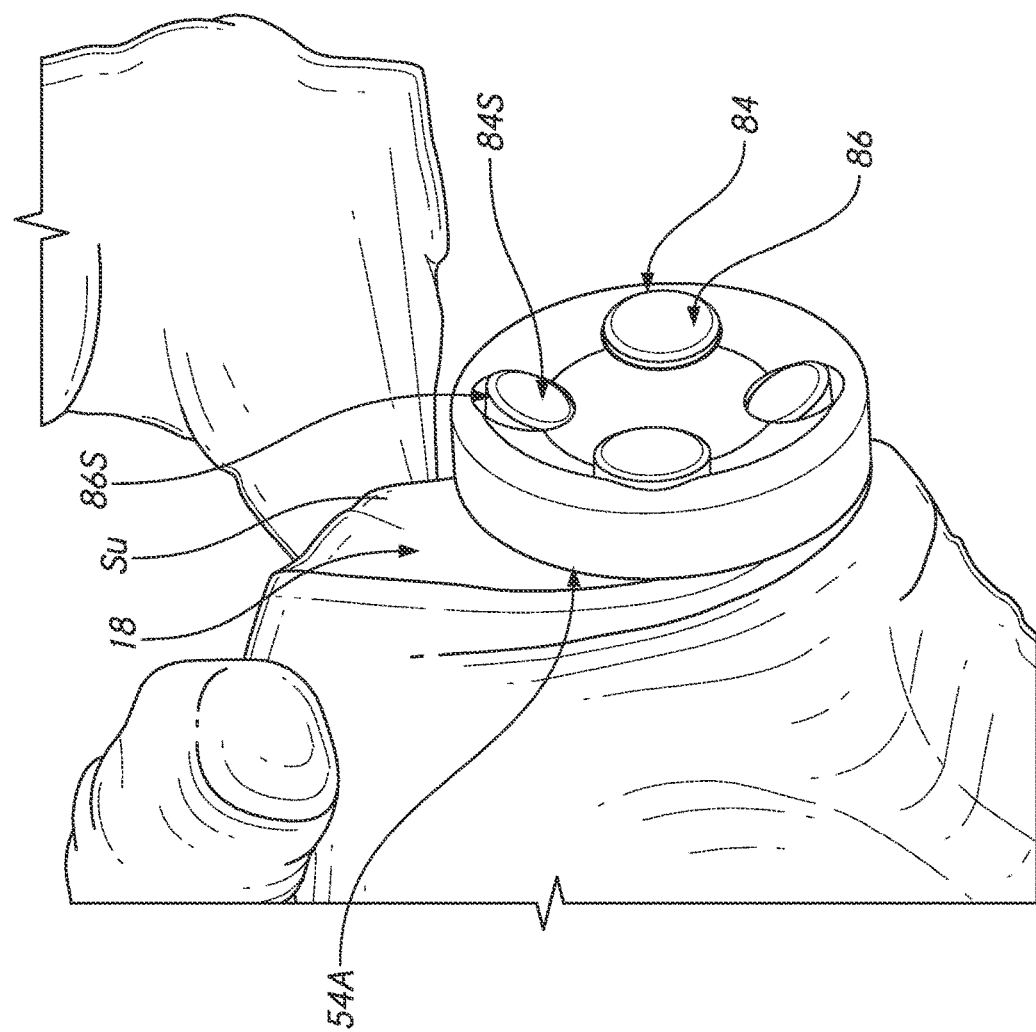
FIG. 9 is a view similar to FIG. 4 showing the baseplate oriented such that each of peripheral anchors thereof find good purchase for a specific patient.

FIG. 9 shows that the use of the anchor trajectory guide 290 improves the connection of the baseplate 54A to the scapula 14. In particular, the superior hole 84S with the peripheral anchor 86S disposed therethrough is in the superior position of the glenoid 18 at or adjacent to the superior portion Su of the glenoid rim. The other three peripheral anchors 86 are placed in the inferior, anterior, and posterior holes 84 of the baseplate 54A. In contrast with the outcome shown in FIG. 4, the distal portions of each of the peripheral anchors 86 and of the superior peripheral anchor 86S are embedded in bone and are not protruding through the bone by significant amounts. In past practice clinicians have been instructed to advance screws until they protrude from the scapula 14. This was done to assure that the tips of the screws were advanced into the cortical bone at the tip thereof. With a patient specific approach, this practice is not needed. For example, any number or combination of patient specific configurations can make the mounting of the baseplate 54A (or other baseplates discussed herein or other glenoid implants) more accurate such that the surgeon can be certain of how the implant is seated. CT or MRI scan images and, as needed, surgeon input can be processed to determine preoperatively how long the peripheral anchors 86, the superior peripheral anchor 86S, or any combination of the screws 86, 86S should be. Also, if the anchors 86, 86S are threaded, the thread pattern (e.g., pitch) can be made patient specific. For example, the thread pattern (e.g., pitch) of portions thereof will be lodged in cortical bone upon completion of the implantation process can have a more suitable configuration for mating with cortical bone and portions to mate with cancellous bone can have a more suitable configuration for mating therewith. The diameter of the anchors 86, 86S can be patient specific, such as providing larger diameters for thicker and larger segments of bone of the specific patient. The diameter of the anchors 86, 86S can be different at different positions along the length thereof in a patient specific manner, such that narrower sections will be provided in some areas that will mate with thinner or smaller bone sections and larger diameter sections can be provided for areas that will mate with thicker and larger segments of bone of the specific patient. Also, as discussed above the anchor trajectory guide 290 can be formed in a patient specific manner to assure that the trajectory of any or all of the screws 86, 86S is/are predefined and accurate to the specific anatomy of a specific patient. Any one or a combination or all of these patient specific approaches including those defined by the anchor trajectory guide 290 can enable the tips of the peripheral anchors 86 and the superior peripheral anchor 86S will be in pre-defined positions in the cortical bone of the scapula 14.

III. Enhanced Control of Glenoid Reamer

FIGS. 10 and 10A show further details of the glenoid implant 50A, which not only replaces the natural articular surface but also fills in some worn area of the glenoid 18. The implant 50A is similar to the glenoid implant 50 except as described differently below. The glenoid implant 50A includes the glenosphere 58, the anchor member 52 and the peripheral anchors 86. Although illustrated with two peripheral anchors 86, the glenoid implant 50A can be configured to have four peripheral anchors 86. One of the peripheral anchors 86 extends through an augment portion configured to supplement the worn area.

The baseplate 54A has a proximal end 66 that is configured to be received in the glenosphere 58. A connection can be formed between an internal surface of the glenosphere 58 and a peripheral surface of the baseplate 54A just distal to the proximal end 66. The baseplate 54A has a bone engaging surface 74A having a non-planar shape. In particular, the bone engaging surface 74A has a planar portion 390 that extends away from approximately a mid-portion of the central protrusion 78 of the baseplate 54A and a wedge portion 394 that extends away from the planar portion 390. The planar portion 390 can rest on a reamed surface of the glenoid 18 that has been reamed in a traditional manner. The wedge portion 394 is configured to fill in a portion of the scapula 14 of the patient. The portion filled in can be a portion that has been worn away or can be just a relatively low area of the glenoid 18 that is desired to be filled. The location and extent of the bone of the glenoid 18 to be filled by the wedge portion 394 is determined via pre-operative CT scan, MRI images or the like. That information can be supplied to a manufacturing facility to custom make a patient specific baseplate 54A. Alternatively, the baseplate 54A can be in a kit with a range of sizes, shapes and angles of the wedge portion 394. A reaming process can be used to form a surface in the glenoid 18 to receive the wedge portion 394.

Figure 11:
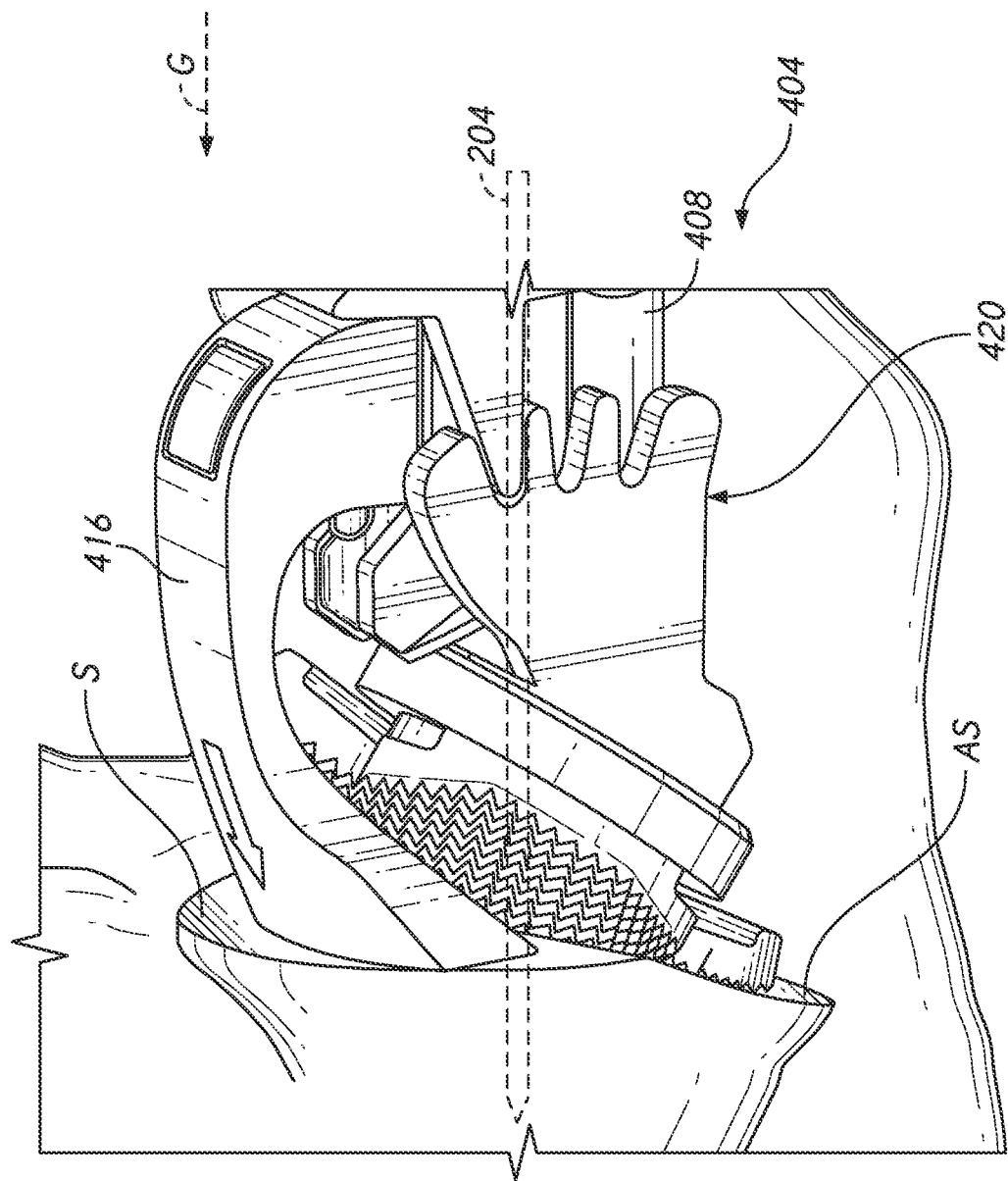
FIG. 11 shows a portion of a method of reaming a glenoid surface to form a complex reamed geometry thereon, the reamer having a depth stop and being advanceable over a central guide pin.

FIG. 11 shows a step of a method that could follow the steps illustrated by FIG. 7. In FIG. 7 the cannulated reamer 270 is used to modify a surface of the glenoid 18. The cutting head 278 can be configured to form a generally planar surface S on the glenoid 18. After the cannulated reamer 270 has completed forming the glenoid 18, the cannulated reamer 270 can be removed along the central guide pin 204. FIG. 11 shows that thereafter an angle surface reamer 404 can be advanced over the central guide pin 204. The angle surface reamer 404 can include a cannulated handle 408 and a head 412 for reaming bone that is rotated by a shaft within the cannulated handle 408. The angle surface reamer 404 is advanced to ream a bone surface to form an angled surface AS. The angled surface AS is at a non-zero angle to the planar surface PS. Further advancement of the angle surface reamer 404 in a direction indicated by an arrow G after initial contact with the planar surface PS transforms a portion thereof into the angled surface AS. In one case, the angle surface reamer 404 includes a head 416 that limits the advancement along the central guide pin 204 in the direction of the arrow G. The angle of the head 416 to the cannulated handle 408 can be adjusted by the adjuster 420, for example to angles such as 15 degrees, 25 degrees, and 35 degrees.

FIG. 12 shows an enhanced reaming assembly 430. The reaming assembly 430 includes the angle surface reamer 404 and a reaming guide 432. The reaming assembly reaming assembly 430 and the reaming guide 432 are examples of rotational position control guides, sometimes referred to herein as rotation guides. The reaming assembly 430 and the reaming guide 432 can control unwanted rotation or other movement of the center of rotation of the head 412 as the head 412 rotates. This helps prevent the head 412 from moving or walking or wandering across the glenoid which would result in imprecise reaming. The angle surface reamer 404 has been discussed above. The reaming guide 432 includes a reamer interface 460 and a rigid body 436 that extend from the interface 460. The reamer interface 460 engages a guide interface 462 that forms a portion of the angle surface reamer 404.

The reaming guide 432 is configured to be patient specific and to provide advantages in preparing the glenoid of the specific patient. For example, as discussed further below the guide 432 is configure to mate with a specific side of the reamer 404, e.g., the side of the reamer opposite the side toward which the head 412 can be oriented to provide the angled surface AS in the glenoid. The position of the angled surface AS can be different for each patient. In the illustrated treatment the angled surface AS will be on the posterior side of the glenoid. So, the rigid body 436 is made patient specific in being configured such that the reaming guide 432 extends from a superior position coupled with the pin 202 to an anterior position for coupling with the reamer 404. Other patients may require the angled surface AS to be formed in an inferior position, so the rigid body 436 should be configured in a patient specific manner to enable the reaming guide 432 to couple with the pin 202 at a superior position and also with the reamer 404 in a superior position. Other patients may require the angled surface AS to be formed in an anterior position, so the rigid body 436 should be configured in a patient specific manner to enable the reaming guide 432 to couple with the pin 202 at a superior position and to extent posteriorly to couple with the reamer 404 in a posterior position. Other patients may require the angled surface AS to be formed in a superior position, so the rigid body 436 should be configured in a patient specific manner to enable the reaming guide 432 to couple with the pin 202 at a superior position and to extend anteriorly or posteriorly around the reamer to couple with the reamer in an inferior position. In some cases, the reaming guide 432 is patient specific in providing a depth stop for the reamer 404. Thus the medial-lateral length of a portion thereof can be configured for the specific patient to define the extent of the reaming that is appropriate based upon pre-operative imaging. Also, the medial end can include a bone contacting surface that is patient specific, e.g., has a complementary contour which can be concave to nest on or receives a convex bone portion.

In one embodiment, the reaming guide 432 is configured to be removeably attached to the angle surface reamer 404 by the reamer interface 460 and the guide interface 462. The reamer interface 460 can include an actuator 480 that is moveable along the longitudinal axis of the cannulated handle 408. The actuator 480 can be retracted in the direction of the arrow H. The guide interface 462 includes an axial member or other mating structure on a distal end thereof that translates with the cannulated handle 408. The angle surface reamer 404 can include a lateral peg 472 that is fixed thereon and is not moveable with the actuator 480. Retracting the actuator 480 moves the axial member or mating structure proximal of the lateral peg 472. The reaming guide 432 can then be moved laterally such that a first aperture 464 thereof receives the lateral peg 472. After the first aperture 464 is fully received the actuator 480 can be released allowing the axial member or mating structure to move back into the second aperture 468 to secure the reaming guide 432 to the angle surface reamer 404. Movement of the actuator 480 to secure the reaming guide 432 to the angle surface reamer 404 can be in the direction opposite to that illustrated by the arrow H. The movement can be upon action of a spring that is compressed when the actuator 480 moves in the direction of the arrow H. Further details of the guide interface 462 are discussed in US2015/0374502, which is hereby incorporated by reference herein in for this purpose and in its entirety.

Figure 13:
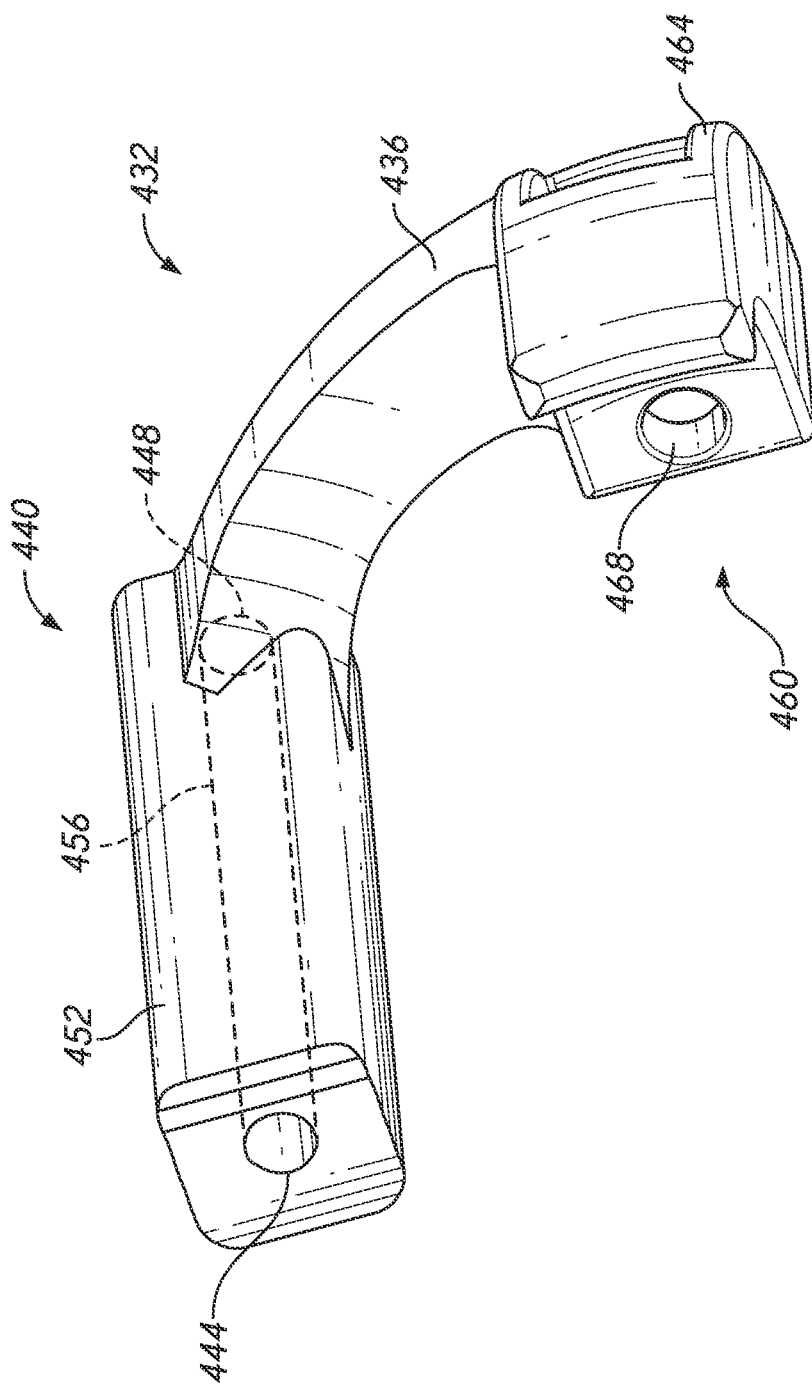
FIG. 13 is a perspective bottom view of a reaming guide that can be used to control reaming of a glenoid surface.
Figure 14:
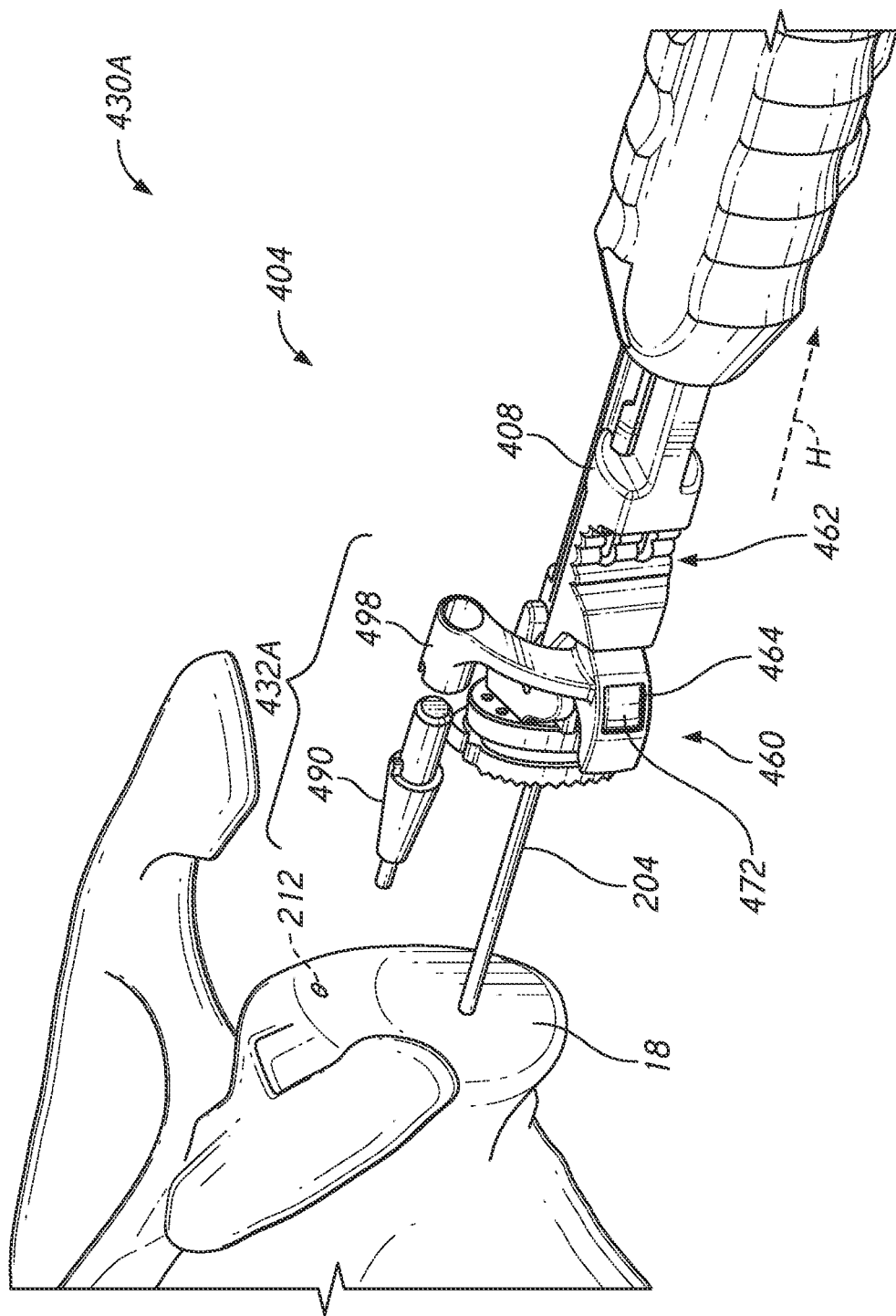
FIGS. 14-15 illustrate further methods of reaming a glenoid surface by reference to a peripheral guide peg assembly and a peripheral aperture formed using the patient specific glenoid guide of FIG. 5.
Figure 15:
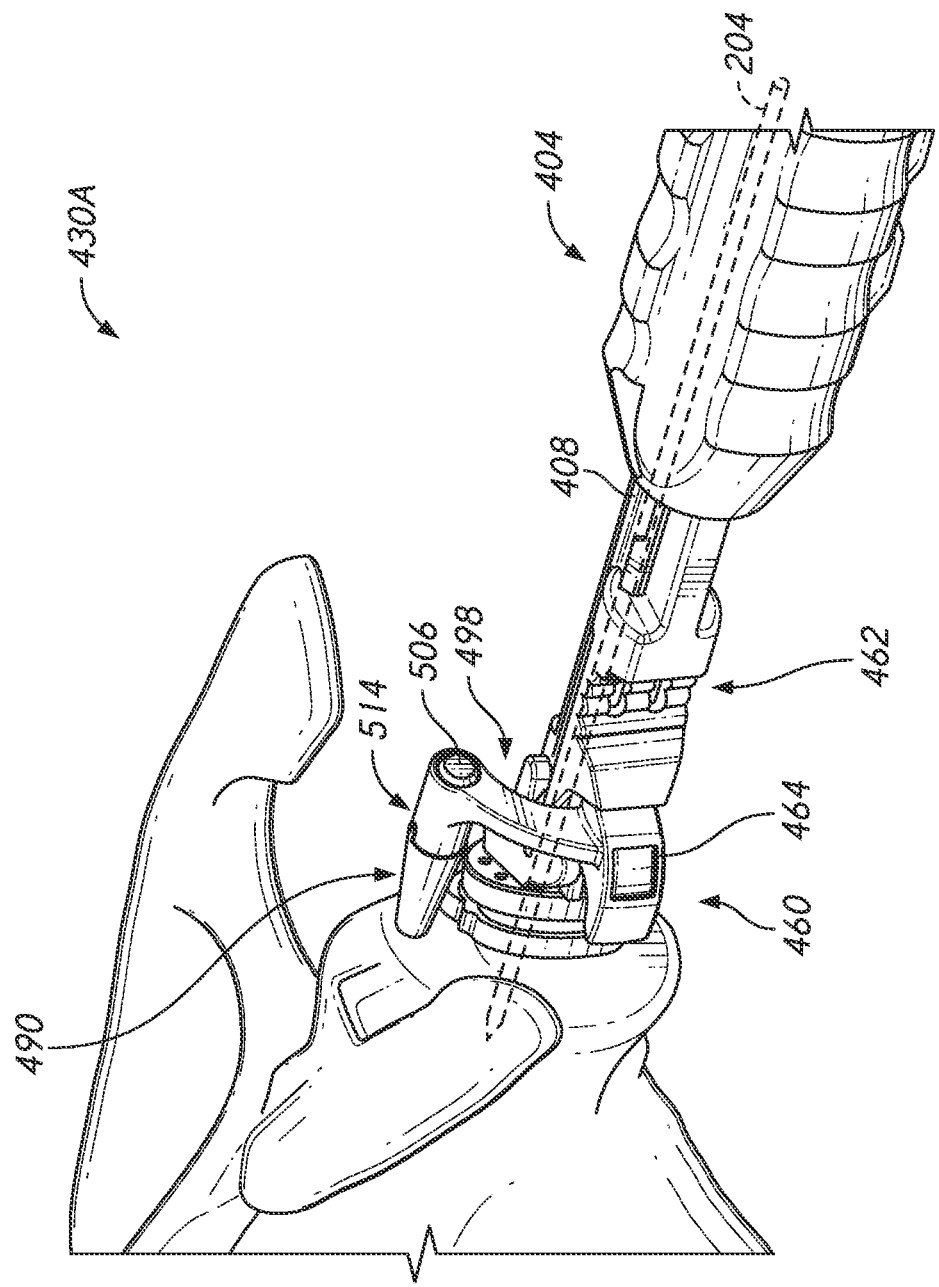
Figure 16B:
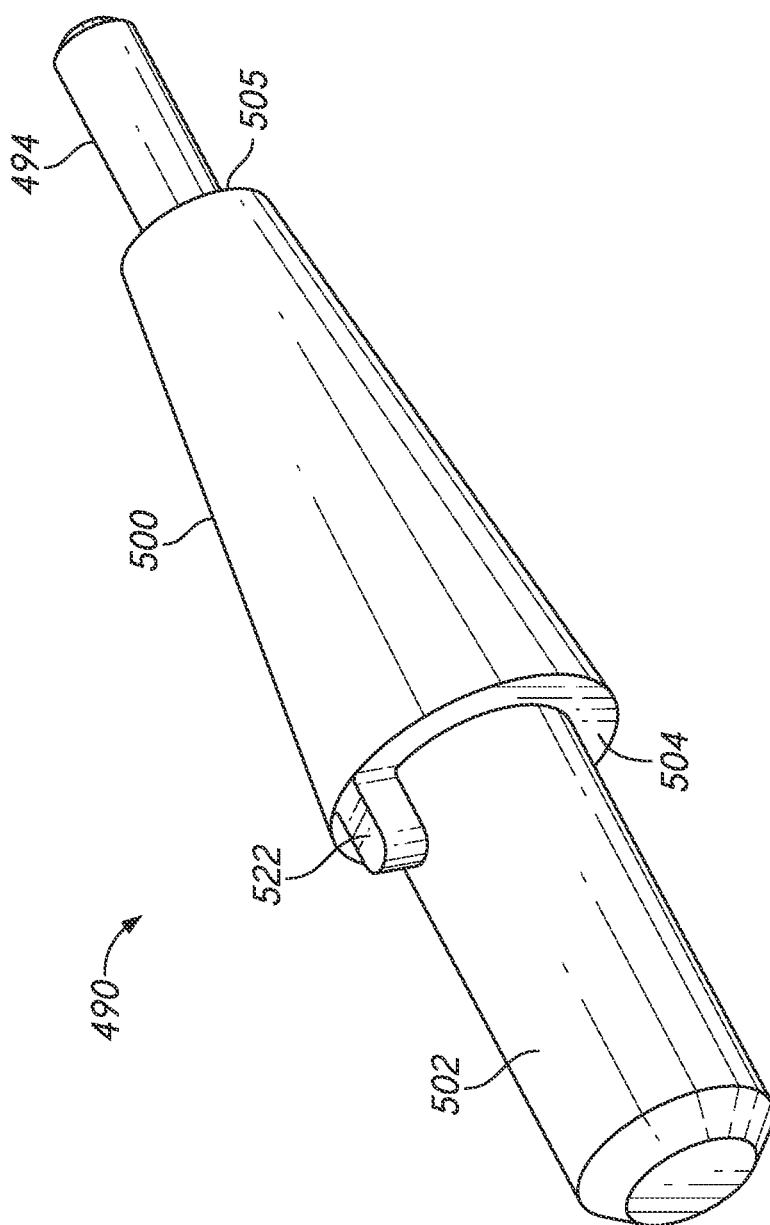

FIG. 13 shows that the rigid body 436 includes a projection 440 that extends distally and proximally. The projection 440 includes a distal opening 444 and a proximal opening 448. An elongate body 452 extends between the projection 440 and the distal opening 444. The elongate body 452 preferably comprises a tubular member that encloses a guide lumen 456 on all sides while the guide lumen 456 remains open on the ends. The elongate body 452 is configured as a depth stop, e.g., having a length that is specific to the patient such that the free end (the medial end) thereof contacts the surface of the scapula 14 to prevent further reaming when the full planned extent of reaming has occurred.

FIG. 12 shows that after the reaming guide 432 is coupled to the angle surface reamer 404, the rigid body 436 of the reaming guide 432 is disposed medial of the head 412 of the angle surface reamer 404. The reaming guide 432 does not obstruct motion of the head 412. The reaming assembly 430 can be moved over the central guide pin 204 and over the peripheral guide pin 208 in a guided manner. The distal opening 444 can be advanced over a proximal end of the peripheral guide pin 208 following advancement of the angle surface reamer 404 over the central guide pin 204. After initially advancing the distal opening 444 over the peripheral guide pin 208 the elongate body 452 can surround the peripheral guide pin 208. The guide lumen 456 can be sized slightly larger than the peripheral guide pin 208 such that there is little to no lateral movement as the reaming assembly 430 is further advanced in a distal direction along both the central guide pin 204 and the peripheral guide pin 208. Upon further distal motion the distal end of the elongate body 452 makes contact with the scapula 14 adjacent to the periphery of the glenoid 18 at an intended depth. The proximal-distal position of the reaming assembly 430 over the central guide pin 204 and the peripheral guide pin 208 provided upon contact of the distal end of the elongate body 452 is as shown in FIG. 12.

The advancement of the reaming guide 432 over the peripheral guide pin 208 enables the angle surface reamer 404 to remain in a proper, prescribed rotational position over the central guide pin 204. This position can assure that the head 412 acts as was intended based upon CT scan images or the like. As a result, the angled surface AS can be in the position that was intended and the reamer 404 can be prevented from operating in other areas of the glenoid 18. By keeping the cannulated handle 408 in a proper rotational orientation relative to the central guide pin 204 the location of the angled surface AS can be assured.

The rigid body 436 between the reamer interface 460 and the projection 440 can be configured to locate the angled surface AS. In the illustrated embodiment, the rigid body 436 between the reamer interface 460 and the projection 440 is curved to extend from a superior position to locate the reamer interface 460 at an anterior position of the glenoid 18 when the guide lumen 456 is over the peripheral guide pin 208. If it is desired to ream the angled surface AS in an inferior position, the rigid body 436 between the reamer interface 460 and the projection 440 could be arranged to extend straight inferiorly to locate the reamer interface 460 at a superior position when the guide lumen 456 is over the peripheral guide pin 208. If it is desired to ream the angled surface AS in an anterior position, the rigid body 436 between the reamer interface 460 and the projection 440 can be curved to extend from a superior position to locate the reamer interface 460 at a posterior position of the glenoid 18 when the guide lumen 456 is over the peripheral guide pin 208. If it is desired to ream the angled surface AS in a superior position, the rigid body 436 between the reamer interface 460 and the projection 440 can be curved to extend from a superior position anteriorly or posteriorly to locate the reamer interface 460 at a position opposite the superior position, e.g., second end 180 degrees from the superior position of the glenoid 18 when the guide lumen 456 is over the peripheral guide pin 208. The rigid body 436 can have other patient specific configurations to locate the reamer interface 460 at a position relative to, e.g., second end 180 degrees offset from a location of the glenoid 18 to be reamed. Further to the discussion above, the rigid body 436 can be patient specific in a circumferential extent, such that it is configured to extend about 90 degrees counterclockwise from a superior position when applied. In one embodiment the rigid body 436 is patient specific in a circumferential extent, such that it is configured to extend about 180 degrees counterclockwise from a superior position when applied. In one embodiment the rigid body 436 is patient specific in a circumferential extent, such that it is configured to extend about 90 degrees clockwise from a superior position when applied. In one embodiment the rigid body 436 is patient specific in extending radially from a first superior position to a second superior position, e.g., not extending circumferentially.

In on further variations discussed more fully below in connection with FIGS. 27A-28B the reamer 404 can be guided free-hand or over the guide pin 204 without requiring the guide pin 208. Rather the referencing the guide pin 208 the reamer 404 can be advanced free hand or over the guide pin 204 with reference another rotation control feature, such as a mark. The mark can be formed via a channel such as an enclosed channel 1010 or an open channel 1060. The mark so formed can provide visual guidance of the reamer 404 relative to the glenoid to properly orient the head 412 to assure that the greatest extent of the reaming is at the proper location of the glenoid as identified from pre-operative imaging.

FIGS. 14-16B show another embodiment of a reaming assembly 430A and various components thereof. The reaming assembly 430A includes the angle surface reamer 404. The reaming assembly 430A also includes a reaming guide assembly 432A. As with the reaming assembly 430 and the reaming guide 432, the reaming guide assembly 432A is a rotation guide assembly in that it guides the reamer 404 in controlling rotational position of the head 412 while uncontrolled movement of the rotational axis thereof. In one embodiment, the reaming guide assembly 432A includes a peg 490 and a rigid body 498 that is engageable with the peg 490. The peg 490 is configured to mate with a peripheral aperture 212. The peg 490 can include a slender distal projection 494 that can be inserted into the peripheral aperture 212. The peg 490 can include a distal facing shoulder 505 configured to rest on the surface of the bone, e.g., in a superior portion of the glenoid 18 when the distal projection 494 is disposed in the peripheral aperture 212. The distal facing shoulder 505 extends radially outward from the distal projection 494 to an enlarged body 500. The distal facing shoulder 505 can be perpendicular to one or both of the distal projection 494 and the body 500. In some embodiments the distal facing shoulder 505 can be a patient specific surface as discussed elsewhere herein, e.g., contoured to mate with the shape of the underlying bone. For example, the distal facing shoulder 505 can have an annular surface extending radially away from the distal projection 494. The annular surface can be patient specific, e.g., having one or more contours in the axial or circumferential direction to nest over underlying bone. Such patient specific contours enable the peg 490 to be placed in the peripheral aperture 212 in a specific rotational position such that a mating feature between the peg 490 and the rigid body 498 is properly positioned. The enlarged body 500 is disposed proximally of the distal projection 494. The peg 490 can include a proximal portion 502 that extends proximally of the enlarged body 500. A proximal facing shoulder 504 can be disposed between the enlarged body 500 and the proximal portion 502. The rigid body 498 can mate with the peg 490. In one embodiment, the rigid body 498 has a guide channel 506 that can comprise a recess formed in the rigid body 498. The guide channel 506 can comprise a lumen that extends entirely through the proximal-to-distal thickness of a free end of the rigid body 498. The guide channel 506 is configured to receive a portion of the peg 490. The guide channel 506 can be disposed in a superior portion 510 of the rigid body 498. The guide channel 506 can be configured to mate with the proximal portion 502 of the peg 490. The proximal facing shoulder 504 can mate with a distal side of the rigid body 498 when the peg 490 is fully received in the guide channel 506 of the rigid body 498. The peg 490, in combination with the rigid body 498, is configured as a depth stop, e.g., having a length and a location of the proximal facing shoulder 504 that is specific to the patient such that the proximal facing shoulder 504 mates with the distal side of the rigid body 498 to prevent further reaming when the full planned extent of reaming has occurred.

The reaming guide assembly 432A is advantageous in enabling a lower cost approach to providing patient specific reaming control. Cost is reduced because a portion of the reaming guide assembly 432A need not be patient specific. That is, the rigid body 498 need not be patient specific so long as the peg 490 is patient specific. Only the peg 490 need be made for a specific patient in some embodiments. In more detail, the peg 490 can be configured in terms of length, surface geometry of patient contact surface, size of contact surface, for example. The rigid body 498 and the rest of the reaming assembly 430A can be universal and used for many different patients. To ensure that the reaming assembly 430A operates in a patient specific manner, in various embodiments a rotation control interface 514 can be provided between the peg 490 and the rigid body 498. The rotation control interface 514 can include a slot 518 disposed on the superior portion 510. The slot 518 can extend from an outside surface of the superior portion 510 to the guide channel 506. The slot 518 can be U-shaped as shown whereby a distal end thereof is open. The open end of the slot 518 can be initially inserted over a proximal end of the peg 490 and advanced over the proximal portion 502 until the slot 518 reaches the ridge 522. The ridge 522 can extend proximally from the enlarged body 500. In one embodiment, a stepped profile is provided between the proximal portion 502 and the enlarged body 500. The stepped profile can have a height (e.g., a change in diameter from the enlarged body 500 to the proximal portion 502) that is approximately equal to the wall thickness of the superior portion 510 of the rigid body 498. The ridge 522 can have a length in the direction between the proximal and distal ends of the peg 490 that is approximately the same as the length in the same direction as the slot 518. The ridge 522 can be fully received in the slot 518 when the rigid body 498 is placed over the proximal portion 502 of the peg 490. When the ridge 522 is received in the slot 518 rotation between the rigid body 498 and the peg 490 (and thus between the angle surface reamer 404 and the bone) is limited, reduced or eliminated.

Figure 17:
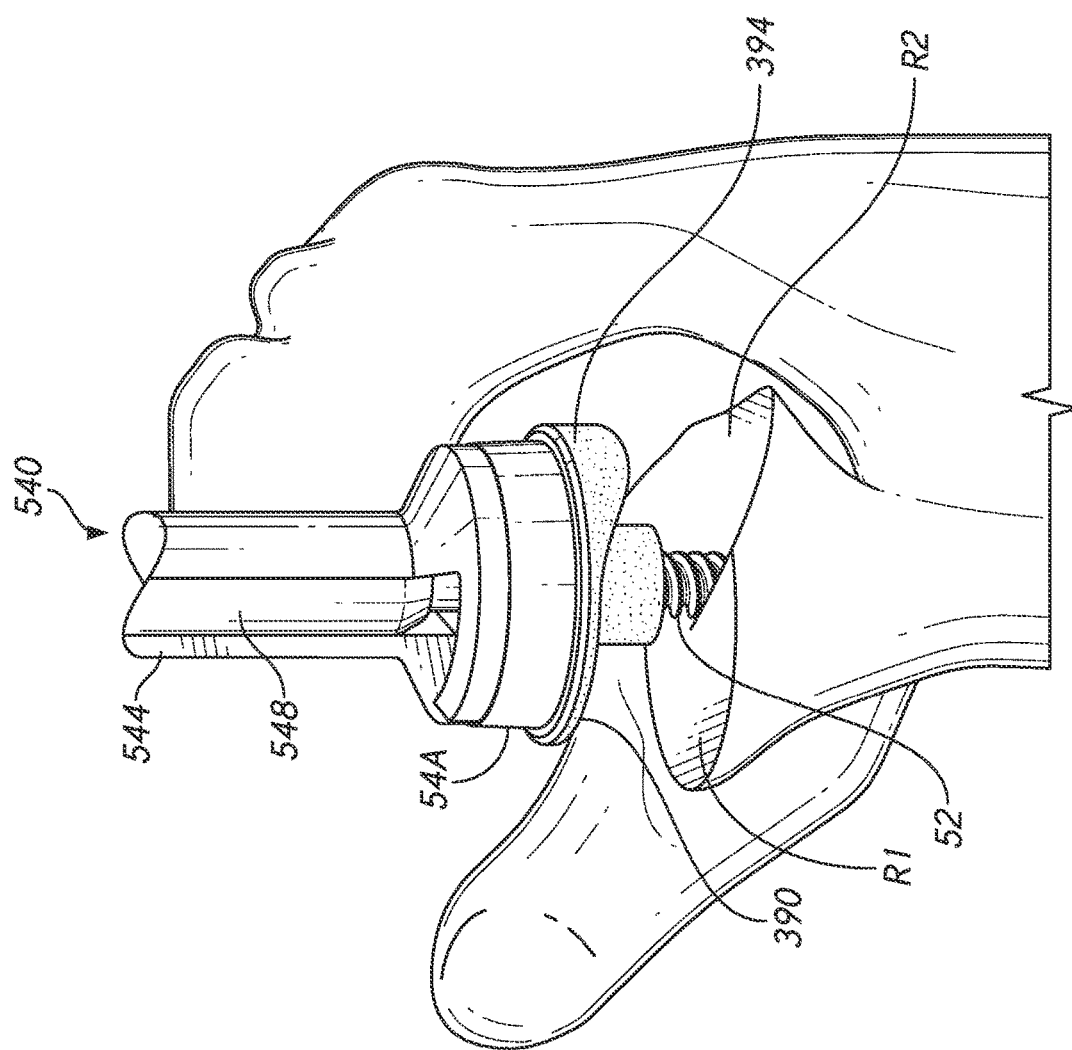
FIGS. 17-18 show a method involving advancing the baseplate of FIG. 10A to and seating the baseplate on a glenoid surface that has been reamed according to one of the methods disclosed herein.
Figure 18:
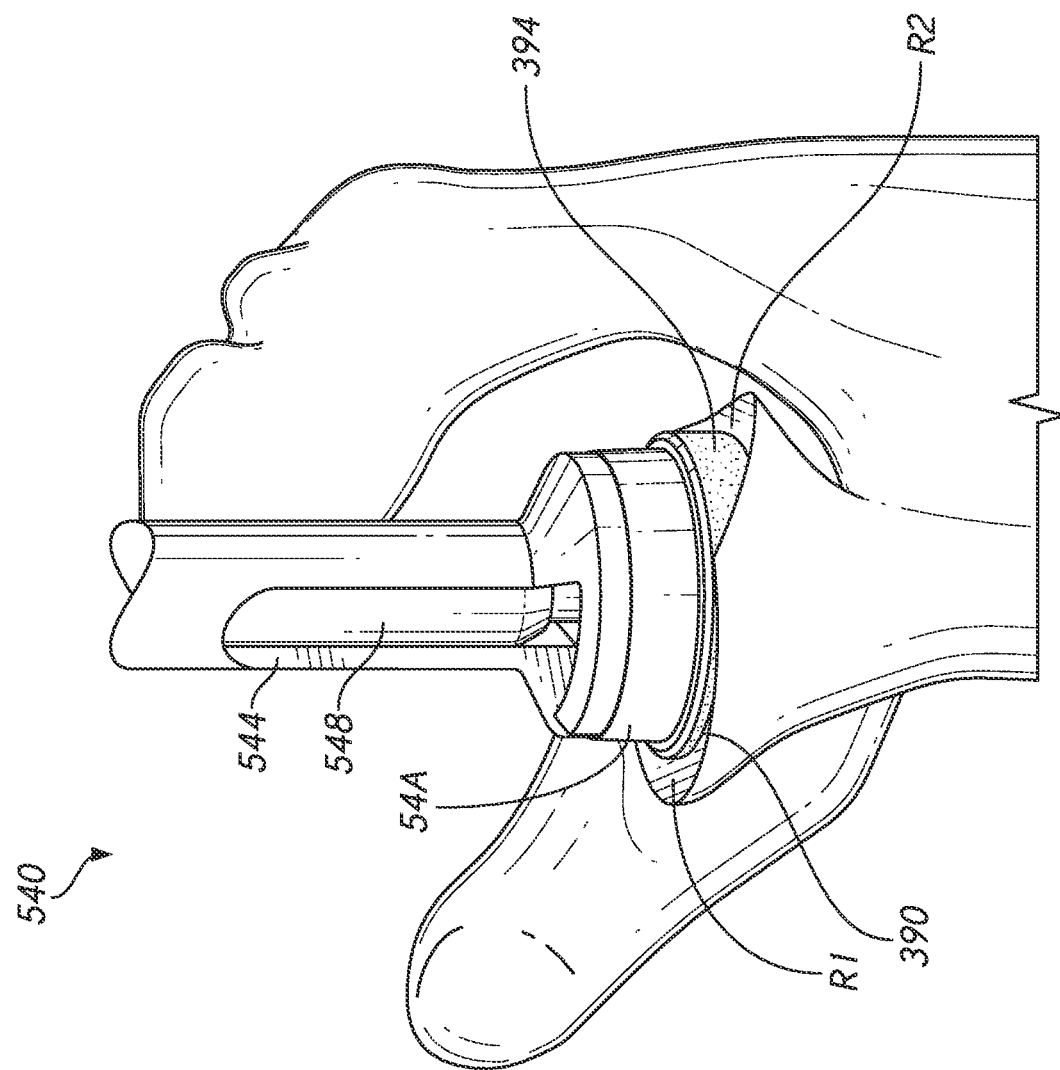

By at least limiting or reducing or in some cases by eliminating rotation of the cannulated handle 408 while permitting rotation of the head 412, the location of the angled surface that is reamed at an angle is more precisely controlled. FIGS. 17 and 18 show that a flat reamed surface R1 and a posteriorly inclined surface R2 can be thus formed as prescribed. The flat reamed surface R1 can be generally perpendicular to a medial-lateral direction or plane of the patient. The angled reamed surface R2 can be oriented relative to the flat reamed surface R1 in an amount and direction prescribed for the patient. Many patients suffer from erosion of the posterior portion of the glenoid 18. Such patients can be treated more effectively using the angle surface reamer 404 and reaming guide 432. Other patients have erosion or degradation of bone in other zones of the glenoid 18. For such patient, the reaming guide 432 or reaming guide assembly 432A can be modified to orient the head 412 to ream the angled reamed surface R2 at the proper orientation, e.g., in an anterior portion, in an inferior portion, in a superior portion, or in other portions of the glenoid 18 such as posterior and inferior, posterior and superior, etc. The location to be reamed can be controlled by forming a portion of the reaming guide 432, 432A to be patient specific as discussed above.

FIG. 17 shows that after the flat reamed surface R1 and the angled reamed surface R2 have been formed a driver 540 can be used to place the baseplate 54A on the glenoid 18. The driver 540 can include an outer shell 544 with a distal end configured to mate with the baseplate 54A. The driver 540 can also include an inner shaft 548 configured to mate with the anchor member 52. The inner shaft 548 can rotate within the outer shell 544 so that the baseplate 54A can be held stationary while the anchor member 52 is rotated by the inner shaft 548. The wedge portion 394 can be aligned with the angled reamed surface R2 as the baseplate 54A is held without rotation by the outer shell 544. The inner shaft 548 can rotate the anchor member 52 to advance the anchor member 52 and the baseplate 54A toward the bone until the planar portion 390 contacts the flat reamed surface R1 and the wedge portion 394 contacts the angled reamed surface R2 as shown in FIG. 18.

FIGS. 17 and 18 are inferior side views of the scapula 14 and the glenoid 18. Although not shown, the peripheral guide pin 208 or a peg, such as the peg 490 can be placed in the peripheral aperture 212 at or adjacent to the superior side of the glenoid 18 to control, minimize or eliminate rotation of the outer shell 544 away from a prescribed orientation such that the alignment of the wedge portion 394 is to the angled reamed surface R2 as prescribed.

IV. Enhanced Rotational Position Control of Glenoid Component

Figure 18A:
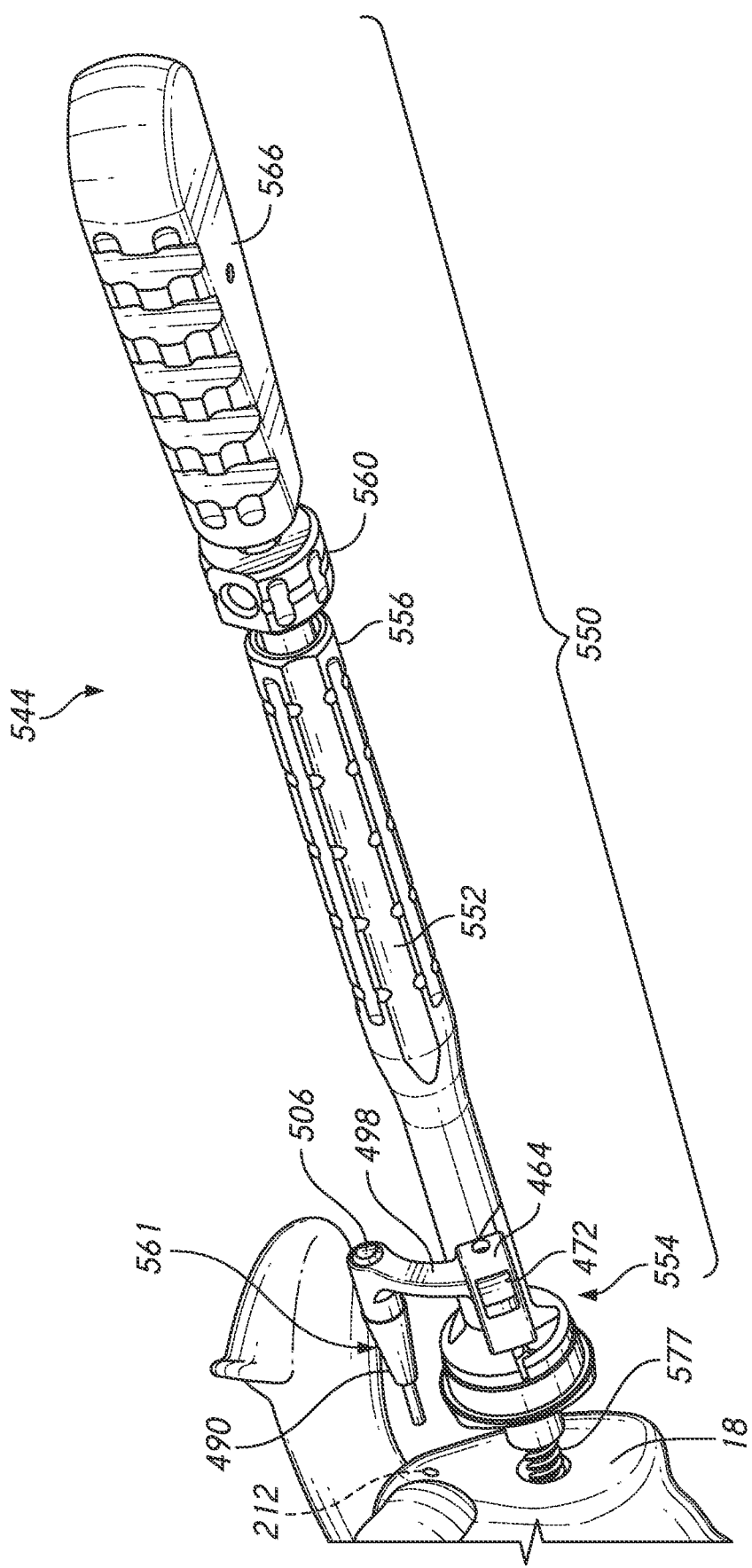
FIG. 18A shows an instrument the use thereof in a further method of advancing an augmented glenoid component such as the baseplate of FIG. 10A to and seating component on a glenoid while providing control of the rotational position of the component.
Figure 18B:
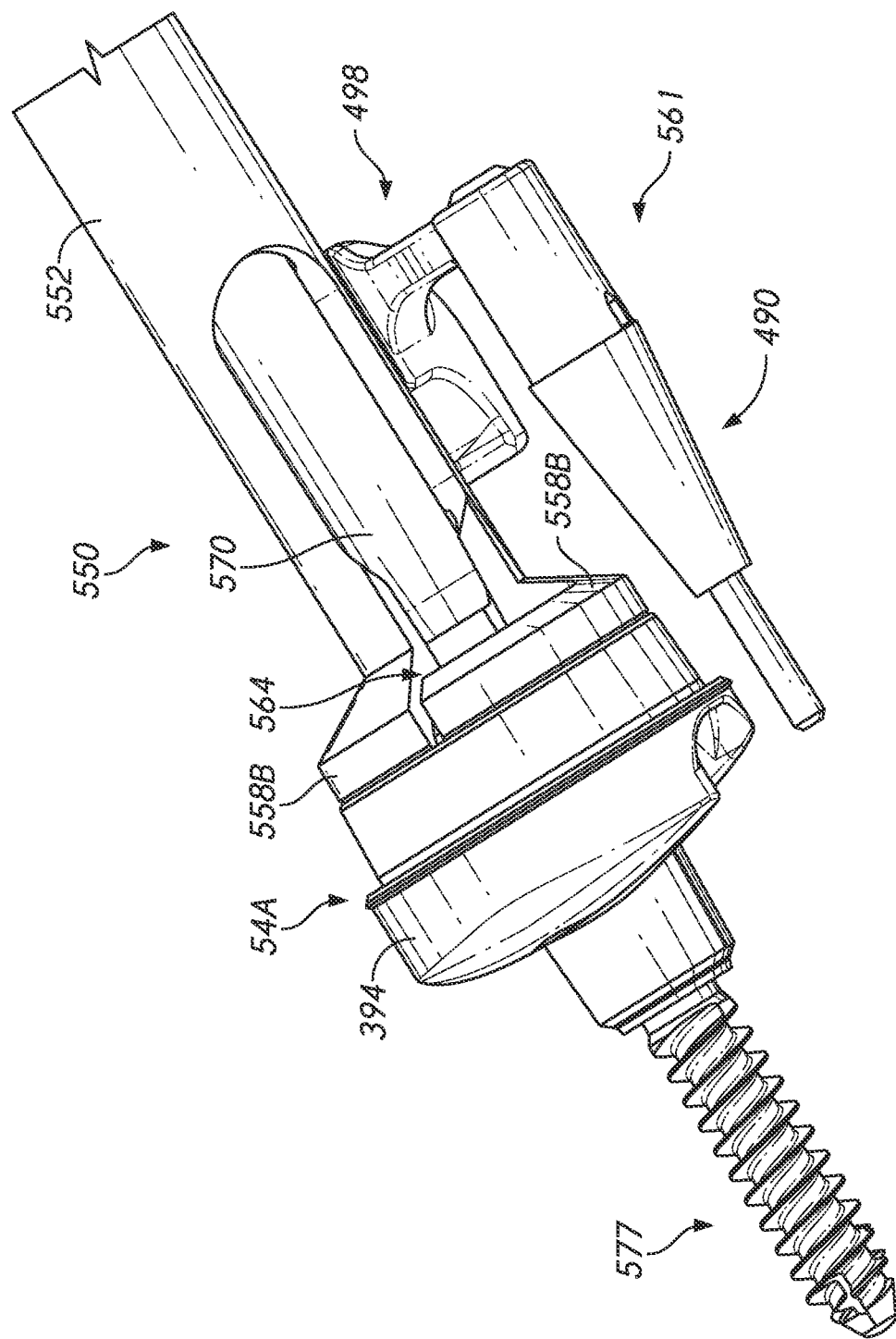
FIG. 18B shows a posterior side perspective view of a medial end of the instrument of FIG. 18A coupled with a rotationally asymmetric glenoid component.
Figure 18C:
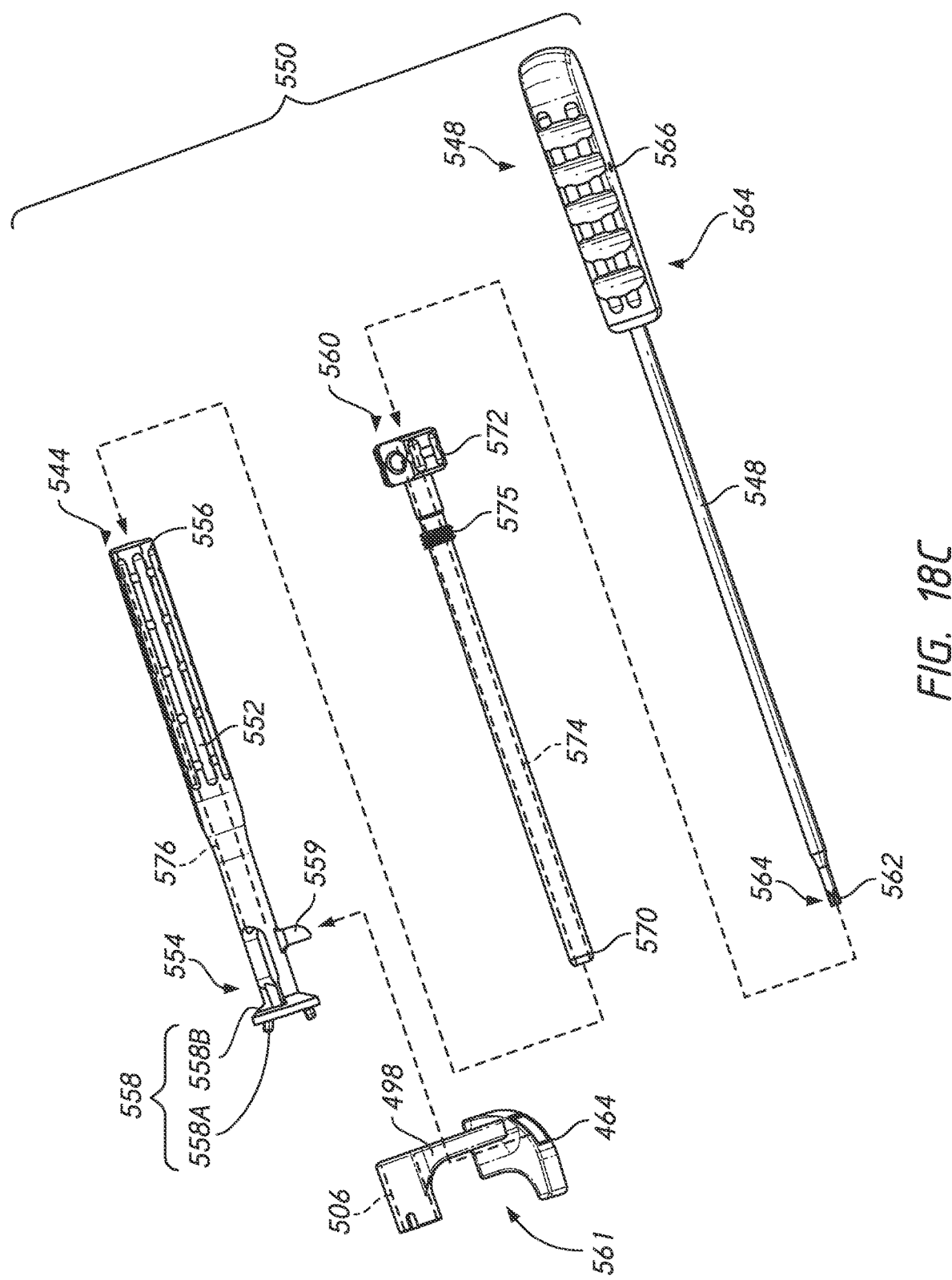
FIGS. 18C and 18D show exploded views of certain portion of the surgical instrument illustrated in FIG. 18A.

While the driver 540 can provide for adequate placement and control of certain implants, it may be advantageous in certain instances to more precisely control one or more components. Examples of components that could benefit from more precise control include rotationally asymmetric components that perform most optimally when aligned to an intended rotational position. The baseplate 54A is one such component in that the thicker wedge portion 394 is intended to be placed at the angled reamed surface R2 which is a surface that has been prepared for such placement. FIGS. 18A-18C show certain patient specific instruments and assemblies that can improve angular position control with reference to an aperture formed in the scapula in a surgical method step. FIGS. 27A-28B show methods of using a glenoid guide to form a rotation control feature, e.g., a mark on or a channel or pin in the bone as a visual reference for subsequent steps of advancing and securing the baseplate 54A or other rotationally asymmetric implant component.

A. Surgical Instrument for Enhanced Position Control of Glenoid Implant

FIG. 18A shows a surgical instrument 550 that is well suited for implanting the baseplate 54A or another augmented glenoid implant or component. The surgical instrument 550 includes an outer shell 544. The outer shell 544 includes an elongate body 552 that has a first end 554 and a second end 556. The outer shell 544 has a glenoid implant component retention feature 558. The glenoid implant component retention feature 558 can be disposed at the first end 554. The glenoid implant component retention feature 558 is adapted to securely couple with a glenoid component, such as the baseplate 54 or the baseplate 54A.

In one embodiment, the glenoid implant component retention feature 558 with one or more tines 558A located on each of two peripheral members 558B for engaging a tooling interface 348 of the baseplate 54A. The peripheral members are able to flex such that the tines 558A can be moved away from and toward a longitudinal axis of the elongate body 552. The peripheral members can each comprise a semi-circular arc 558C. Each of the tines 558A can be disposed in the approximate center of one of the arcs 558C. The ends of one of the arcs 558C can face but be spaced apart by gaps from the ends of the other arcs 558C. The gaps 558C between the ends of the arcs allow the arcs to move away from each other and toward each other.

FIG. 18B shows an enlarged view of a medial end of the surgical instrument 550. This view shows the screw 577 and the baseplate 54A coupled with the elongate body 552 of the outer shell 544. Also, the rotation guide 561 is coupled with the outer shell 544 of the surgical instrument 550. The rigid body 498 of the rotation guide 561 is coupled with the peg 490.

Figure 18D:
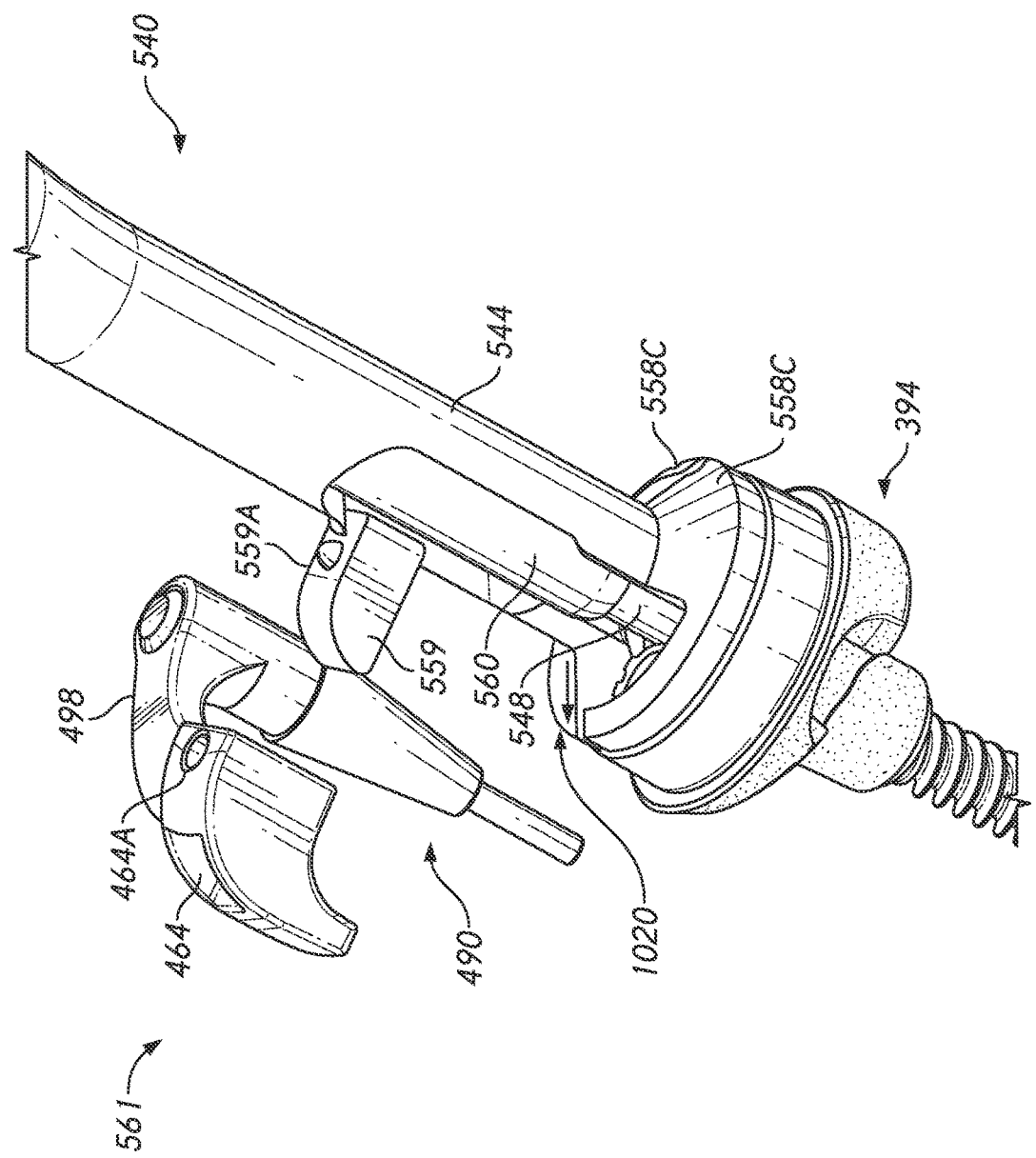

FIG. 18C shows that the surgical instrument 550 can also include an interface portion 559 that is adapted to interface with, e.g., to releasably engage a rotation guide 561 as described further below. FIG. 18D shows that the interface portion 559 can include a spring-loaded ball 559A or other detent structure to engage an aperture 464A or other recess in the rotation guide 561 such that secure but releasable connection can be made between the outer shell 544 and the rotation guide 561. The aperture 464A and the first aperture 464 can be contiguous with one another. In some variations the rotation guide 561 is integrated into and is not removeable from other components of the surgical instrument 550, such as the outer shell 544.

An inner shell 560 is disposed within the outer shell 544. In certain embodiments the inner shell 560 is configured to slide within the outer shell 544. For example, the outer shell 544 can have a lumen that is larger than an outer periphery of the inner shell 560 at least along a length thereof adjacent to the second end 556. This allows a first end 570 of the inner shell 560 to be inserted into the second end 556 of the elongate body 552. The first end 570 can then slide toward the first end 554 of the elongate body 552. The lumen of the elongate body 552 can be smaller than an outer periphery of the inner shell 560 at least adjacent to the first end 570 of the inner shell 560. Further advancement of the inner shell 560 within the lumen of the outer shell 544 can result in retention of the baseplate 54A or other component to be placed.

In certain embodiments, the inner shell 560 can have a first position and a second position within the outer shell 544. The first position can be somewhat retracted from the first end 554 such that the tines 558A of the glenoid implant component retention feature 558 can be allowed to deflect or can be located toward the longitudinal axis of the elongate body 552. The second position can be one in which the first end 570 of the inner shell 560 is advanced relative to the first end 554 of the outer shell 544 such that the first end 570 is located within the glenoid implant component retention features 558. In some embodiments, the second position is one in which the first end 570 is within or adjacent to a portion of the glenoid implant component retention feature 558 which causes the tines 558A to expand into a retention configuration with the baseplate 54A.

Certain embodiments are configured for maintaining the retention configuration without continued surgeon manipulation of the surgical instrument 550. For example, a threaded interface can include threads 575 disposed on an elongate body of the inner shell 560. The first position of the inner shell 560 can be provided by sliding or longitudinal translation, e.g., without requiring rotation. The second position can be achieved by engaging through rotation the threads 575 with corresponding threads in the lumen 576 of the elongate body 552. The threaded interface can enhance the force applied to the glenoid implant component retention feature 558 to provide greater security of the baseplate 54A (or other component) to the surgical instrument 550. Rotation of the inner shell 560 can be enhanced by a knob disposed at the second end 572 thereof. Upon complete rotation of the inner shell 560 the first end 570 is fully disposed in and fully actuates the glenoid implant component retention feature 558 to provide secure retention. The threaded interface also has sufficient friction against counter-rotation that the position of the inner shell 560 within the outer shell 544 can be maintained even after the surgeon releases the inner shell 560.

The surgical instrument 550 can include a rotation guide 561 configured to provide increased control of the surgical instrument 550 and thereby of a rotationally asymmetric glenoid implant, such as the baseplate 54A. The rotation guide 561 can have the same configuration as the reaming guide assembly 432A but of course is incorporated into the surgical instrument 550. The rotation guide 561 can include a rigid body 498. The rigidity of the rigid body 498 prevents the surgical instrument 550 from moving out of an intended position, as discussed further below. The rotation guide 561 can include an instrument interface, such as the first aperture 464 and/or the aperture 559B, and a bone interface portion. The first aperture 464 (or other instrument interface) is used to connect the rotation guide 561 with another part of the surgical instrument 550. The connection of the rotation guide 561 to another part of the surgical instrument 550 can be temporary. The instrument interface can engage the interface portion 559. In certain embodiments the interface portion 559 is the same as or similar to the lateral peg 472, discussed in connection with FIGS. 12 and 14 above. The lateral peg 472 can have the spring-loaded ball 559a disposed therein. The lateral peg 472 can be disposed on the surgical instrument 550, e.g., disposed on the outer shell 544 of the surgical instrument 550. The rotation guide 561 can interface with the bone with a separable structure such as the peg 490, which is discussed above. As discussed, the peg 490 can have a patient specific contact surface, e.g., at the distal facing shoulder 505. The bone interface portion of the rotation guide 561 can include the guide channel 506 of the rigid body 498.

FIG. 18C shows that the instrument and bone interfaces can be located on opposite ends of the rigid body 498. The configuration of the rigid body 498 between the instrument and bone interfaces controls the rotational position of the surgical instrument 550 and thereby the baseplate 54A or other rotationally asymmetric component coupled therewith as the baseplate or component is being coupled with the prepared glenoid. In some embodiments, the shape of the rigid body 498 is configured for a specific patient to control the rotational position of a glenoid implant component. In some embodiments the length of the rigid body 498 is configured for a specific patient to control the rotational position of a glenoid implant component. In some embodiments the shape and the length of the rigid body 498 is configured for a specific patient to control the rotational position of a glenoid implant component. In a specific example, the guide channel 506 is configured to be advanced over a peg 490 that is placed in the peripheral aperture 212 disposed at a superior glenoid position. In one case, the shape and length of the rigid body 498 result in the first aperture 464 being positioned at the anterior side of the glenoid generally in a mid-region along a superior-to-inferior axis. This position allows a thicker part of the baseplate 54A (e.g., the wedge portion 394) to be aligned to a more extensively reamed or otherwise more medial portion of the glenoid. As discussed elsewhere herein the shape and/or length of the rigid body 498 can result in placement of the thicker part of the baseplate 54A to be in any pre-defined position, which position can be patient specific based on pre-operative imaging (e.g., CT scan, MRI scan, X-ray or the like) and analysis as discussed herein.

The interface portion 559, e.g., the lateral peg 472, can be configured to releasable engage the outer shell 544 with the rotation guide 561. This configuration enables the rotation guide 561 to be used only one time and to enable the rest of the surgical instrument 550 to be cleaned and used again with another patient.

In one embodiment, the interface portion 559 is disposed on a side opposite to where the wedge portion 394 of the baseplate 54A is to be positioned when properly aligned to and coupled with the glenoid implant component retention feature 558. As a result, the surgeon knows without any visual confirmation that the baseplate 54A is properly aligned when the interface portion 559 is coupled with the rigid body 498 at the instrument interface, e.g., at the first aperture 464 and the guide channel 506 is coupled with the peg 490 placed in the peripheral aperture 212. The bone interface portion of the rotation guide 561, e.g., the guide channel 506, could be placed over the peg 490 which is placed inferiorly. The rigid body 498 could then extend anteriorly and superiorly to an anterior position to align the wedge portion 394 with the angled reamed surface R2 if that surface is located in the posterior portion of the glenoid. The bone interface portion, e.g., the guide channel 506 could be placed over the peg 490 when placed in the peripheral aperture 212 at a superior position. The rigid body 498 of the rotation guide 561 could then extend anteriorly and inferiorly to an anterior position to align the wedge portion 394 with the angled reamed surface R2 if that surface is located in the posterior portion of the glenoid. Many other variations can be employed to place the wedge portion 394 in any angular position around the glenoid, e.g., inferior, anterior, superior, posterior, or any location between these angular positions.

Although the rotation guide 561 is illustrated as an assembly of the peg 490 and the rigid body 498, the rotation guide 561 could be configured similar to or the same as the reaming guide 432 in which the elongate body 452 is adapted to be advanced over a guidewire until the distal opening 444 is abutting the surface of the glenoid. In such embodiments the wire can be considered a portion of the rotation guide 561. The elongate body 452 can include a patient specific medial face for contacting the patient. The length of the elongate body 452 can be such that the glenoid 18 when the medial face contacts the glenoid. The rigid body 436 extends to the first aperture 464 which can engage the interface portion 559 (e.g., receive the spring loaded ball 559a of the lateral peg 472 in the aperture 464A).

FIG. 18C shows how the surgical instrument 550 is assembled. The inner shaft 548 can be coupled with the inner shell 560 by inserting the first end 564 (of 566) into the second end 572 of the inner shell 560. The inner shaft 548 can slide within the lumen 574 until at least the torque interface 562 emerges from the first end 570. In this position the knob at the second end 572 is adjacent to the medial end of the handle 566 of the inner shaft 548. The inner shell 560 together with the inner shaft 548 can be inserted into the first end 570 of the outer shell 544. Specifically, the torque interface 562 and the first end 570 can be inserted into the second end 556 and advanced within the lumen 576 until at least the torque interface 562 emerges from the second end 556. In this position the knob of the inner shell 560 is between the handle 566 and the second end 556 of the outer shell 544. The rotation guide 561 can also be coupled with the interface portion 559 of the surgical instrument 550. As discussed above, in one embodiment the interface portion 559 is on the outside surface of the elongate body 552 of the outer shell 544. Thus, the interface portion 559 can be coupled to the outer shell 544. The baseplate 54A can then be coupled with the glenoid implant component retention feature 558. For example, the tines 558A can be inserted into the tooling interface 348 of the baseplate 54A. After being so inserted, the first end 570 of the inner shell 560 can be moved toward the first end 554 of the outer shell 544. This movement is to a second position, which is one in which the baseplate 54A is securely held to the surgical instrument 550. Such secure holding or retention can be achieved by engaging the threads 575 with internal threads in lumen 576 of the outer shell 544.

The inner shaft 548 can freely rotate within the lumen 574 when the inner shell 560 is in the first position and when the inner shell 560 is in the second position within the outer shell 544. As a result, the baseplate 54A can be held stationary on the glenoid implant component retention feature 558 while the inner shaft 548 rotates. The surgeon can hold the knob at the second end 572 of the inner shell 560 while rotating the handle 566 at the first end 564 of the inner shaft 548. In one embodiment, the inner shaft 548 is solid with no lumens. The trajectory of advancement of a screw 577 (see FIG. 18A) coupled with the torque interface 562 can be controlled either by pre-forming a central channel in the glenoid 18 or by the rigidity of the rotation guide 561 or a combination of these structures. In other embodiments, the inner shaft 548 is cannulated with a lumen for tracking over a guidewire.

Having described the structure of the surgical instrument 550, the following provides examples of how the surgical instrument 550 can be used. After the glenoid 18 is exposed, a peripheral aperture 212 can be formed in the scapula 14, e.g., at a superior position of the glenoid 18. The peripheral aperture 212 is one example of a rotation control feature as discussed herein. The peripheral aperture 212 can be placed anywhere around the glenoid 18 in variations of the method. The peripheral aperture 212 can be formed using a glenoid guide, such as the patient specific shoulder guide 100. For example, a drill or punch can be directed through the aperture 198 in the peripheral member 108S.

A rotationally asymmetric glenoid component, such as the baseplate 54A, can be advanced onto the glenoid 18. The advancement of the baseplate 54A can be with reference to the peripheral aperture 212 or to another rotation control feature. Such advancement can align the rotationally asymmetric glenoid component to the glenoid 18 in a prescribed rotational position for the specific patient. The reference to the peripheral aperture 212 can be in any suitable manner. FIG. 18A shows that in one example, the peg 490 and the rotation guide 561 are used to reference the peripheral aperture 212. The peg 490 and the rotation guide 561 are shown assembled together and the rotation guide 561 assembled to the outer shell 544 of the surgical instrument 550. The arrows in FIG. 18C show how this assembly can occur. That is the inner shaft 548 can be inserted into the inner shell 560. The inner shaft 548 and the inner shell 560 can thereafter be inserted into the outer shell 544. The first aperture 464 of the rotation guide 561 can then be advanced over the interface portion 559, which can be configured in a manner similar to the lateral peg 472.

FIG. 18A shows that as the screw 577 is initially advanced into a central region of the glenoid 18. As discussed above, the rotation of the screw 577 can be achieved by rotating the handle 566 relative to the inner shell 560 and/or the outer shell 544. The surgeon can grasp and hold stationary the knob at the second end 572 of the inner shell 560 while rotating the handle 566 to provide this relative rotation. The screw 577 can be advanced into a pre-formed central aperture, which can be formed by the patient specific shoulder guide 100 or by any other guide disclosed herein. Rotation of the screw 577 causes the threads thereof to advance the screw 577 into the glenoid 18 and the rest of the surgical instrument 550 toward the glenoid 18. Further advancement brings the distal projection 494 of the peg 490 into the peripheral aperture 212. The peripheral aperture 212 thereafter prevents any rotational movement of the elongate body 552 and therefor the glenoid implant component retention feature 558 and the baseplate 54A by its interaction with the distal projection 494 of the peg 490. The peripheral aperture 212 and the peg 490 therefor assist in maintaining the alignment of the baseplate 54A to the glenoid 18 in a prescribed rotational orientation for the specific patient.

Further rotation of the screw 577 draws the baseplate 54A into engagement with the lateral surface of the glenoid 18. The amount of advancement of the screw 577 can be patient specific. For example, the distal facing shoulder 505 of the peg 490 can be patient specific in mating with the glenoid 18 in a specific manner. The medial-lateral distance from the glenoid 18 to the interface portion 559 can determine for the specific patient how far the screw 577 is advanced. For example, the position of the rigid body 498 from the distal end of the inner shell 560 can determine how close the torque interface 562 is to the glenoid 18 when the distal facing shoulder 505 contacts the scapula 14 preventing further medial motion of the surgical instrument 550.

In one variation, part of advancing the baseplate 54A onto the glenoid 18 includes coupling a rigid body 436 with the baseplate 54A and with the peripheral aperture 212. This can be done by first mating the peg 490 with the peripheral aperture 212. Thereafter the screw 577 is advanced until the guide channel 506 is disposed adjacent to the proximal portion 502 of the peg 490. The guide channel 506 can be configured as a lumen in a cylindrical member and can be formed to slide over the proximal portion 502. Further advancement of the screw 577 causes the guide channel 506 to be advanced over the proximal portion 502 until the slot 518 mates with the ridge 522 that projects laterally of the proximal facing shoulder 504 of the peg 490. The peg 490 provides a direct bone interface portion. The guide channel 506 provides an indirect bone interface portion, e.g., through the peg 490.

In one variation, a peripheral wire is used in place of the peg 490. The guide 432 can mate with the outer shell 544 of the surgical instrument 550 and can slide over the wire. The guide 432 can be configured to contact the glenoid 18 of the specific patient when the screw 577 has been advanced an amount prescribed prior to the surgery. The guide 432 can be non-specific as to the depth of the screw 577 but be patient specific in other ways. For example, the guide 432 can be shaped or sized to couple with the interface portion 559 to retain the surgical instrument 550 and thereby the baseplate 54A in a prescribed rotational position relative to the glenoid 18 of the specific patient.

Once the screw 577 is fully advanced, additional peripheral screws can be placed. Prior to placing the peripheral screws the surgical instrument 550 is disengaged from the lateral side of the baseplate 54A. This can be achieved by retracting the inner shell 560 such that the first end 570 is spaced further away from the glenoid implant component retention feature 558 allowing the tines 558A to slip out of the tooling interface 348 of the baseplate 54A. Thereafter peripheral screws can be advanced through the peripheral holes 84 in the baseplate 54A. The placement of the peripheral screws can be made patient specific by any suitable method, such as any of the patient specific methods described herein. For example, the anchor trajectory guide 290 can be mated with the baseplate 54A to direct a punch or drill to form the peripheral screw apertures in a patient specific manner.

B. Surgical Instrument for Enhanced Position Control of Glenoid Implant

Figure 27B:
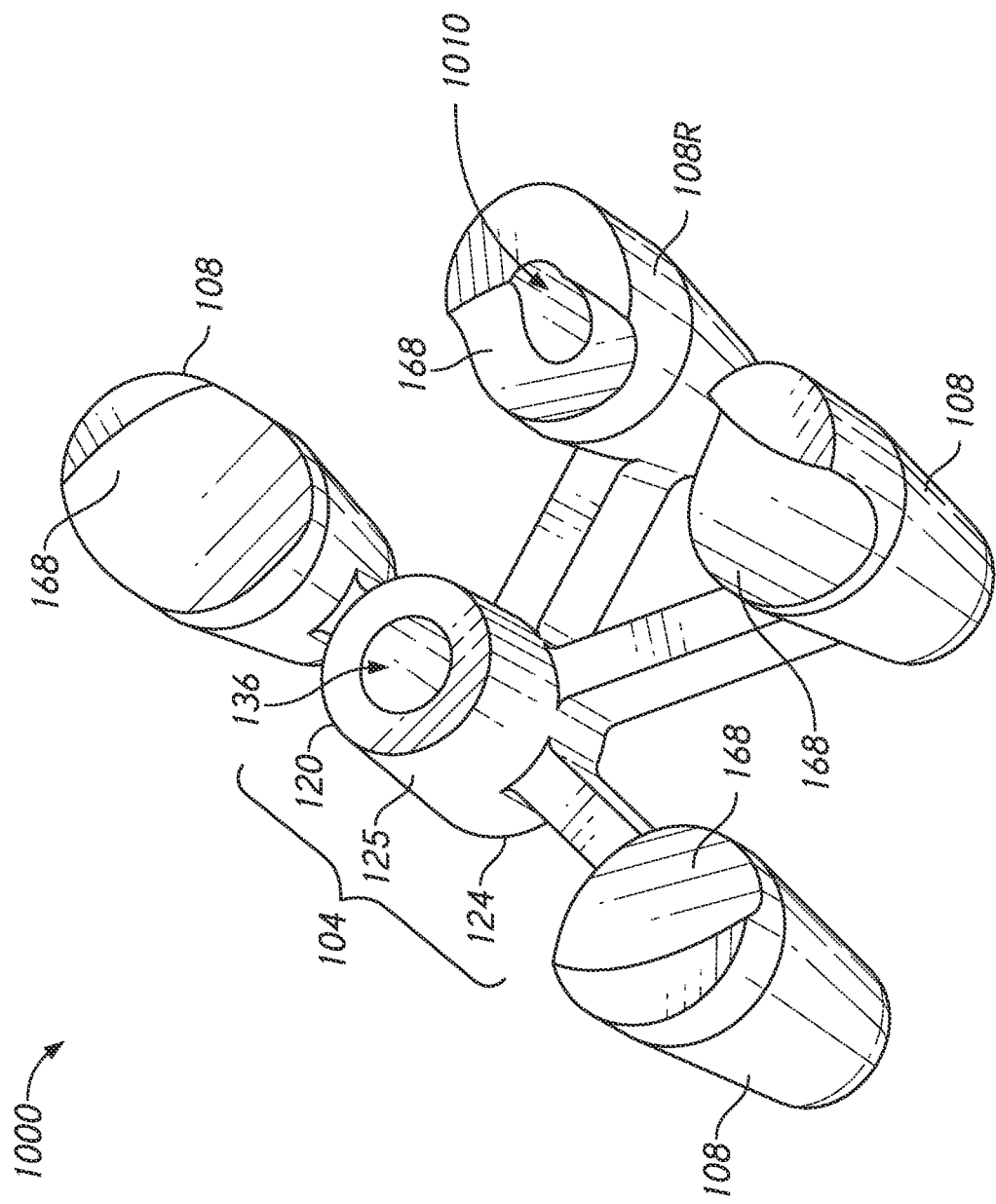
FIG. 27B is a medial perspective view of the patient specific glenoid guide of FIG. 27A.

While a surgical instrument with a patient specific rotation guide can be used to advance and secure an implant to the glenoid without requiring direct visualization of the scapula, FIGS. 27A-28B illustrate various apparatuses and methods that benefit from facilitating bone markings to control rotational position of a rotationally asymmetric glenoid component. FIGS. 27A-28B illustrate various devices that can provide a visible rotation control features, such as a mark. The mark can be used to guide a reamer to form a surface ready to receive a rotationally asymmetric glenoid component. The surface can be disposed at a non-orthogonal angle to a guide pin or to the orientation of a longitudinal axis of the reamer and/or at an acute angle to another reamed glenoid surface. Whether or not the rotation control feature is used to control the reamer, the mark or other rotation control feature can be used to control angular orientation of a rotationally asymmetric implant, such as the baseplate 54A. An advantage of the devices of FIGS. 27A-27B is that rotational position control can be provided in a shoulder guide that serves other purposes, e.g., to form a central or peripheral aperture for placement of pins therein to guide reaming, peripheral screw channel formation or other patient specific or generic methods.

FIG. 27A shows a glenoid guide 1000 that can be used to provide a mark 1014 on the scapula 14, e.g., on the glenoid rim 17 or the glenoid 18. The shoulder guide 1000 can have similar structures to any of the other glenoid guides described herein. The description of all of the other guides is therefore incorporated by reference here and will not be reiterated but should be considered to supplement the following discussion of the glenoid guide 1000.

The glenoid guide 1000 includes a posterior portion 1002 and an anterior portion 1004. The glenoid guide 1000 is configured such that when coupled with the glenoid 18 of a specific patient, the posterior portion 1002 is disposed over the posterior portion of the glenoid 18 and the anterior portion 1004 is disposed over the anterior portion of the glenoid. The glenoid guide 1000 includes a hub 104 that is disposed in a central region of the glenoid guide 1000, e.g., where the posterior portion 1002 and the anterior portion 1004 come together. Although generally centrally located, the hub 104 can be off-set from the geometric center of the glenoid 18 depending on the specific patient needs. The location of the hub 104 should correspond to the location of the geometric center of the baseplate 54 or the baseplate 54A to be placed on the glenoid 18. The location of the hub 104 and a central channel therethrough can be shifted superiorly of the geometric center of the glenoid 18 for a specific patient. The location of the hub 104 and a central channel therethrough can be shifted inferiorly of the geometric center of the glenoid 18 for a specific patient. The location of the hub 104 and a central channel therethrough can be shifted anteriorly of the geometric center of the glenoid 18 for a specific patient. The location of the hub 104 and a central channel therethrough can be shifted posteriorly of the geometric center of the glenoid 18 for a specific patient. The glenoid guide 1000 includes a plurality of peripheral members 108. The posterior portion 1002 includes one peripheral members 108 and the anterior portion 1004 includes three peripheral members 108. Each of the peripheral members 108 includes an inner end 160 coupled with the hub 104 and an outer end 164 disposed radially away from the hub 104.

The glenoid guide 1000 has height in a medial-lateral direction. FIG. 27B shows this dimension in connection with the hub 104, which has a first end 120, a second end 124, and an elongate body 125 disposed between the first end 120 and the second end 124. The first end 120 faces the glenoid 18 when applied thereto, and therefore is on the medial side of the glenoid guide 1000. The second end 124 faces away from the glenoid 18 and thus is on the lateral side of the glenoid guide 1000. Each of the peripheral members 108 can also have one or more height dimensions. The span between the inner end 160 and the outer end 164 can have a height dimension less than that of the hub 104. The radially outer portion of each of the peripheral members 108 can have a patient specific contact surface 168, as discussed in connection with the patient specific shoulder guide 100. The medial-lateral dimension or height of one or more of the peripheral members 108 can be less than that of one or more of the other peripheral members 108 as discussed more in connection with FIGS. 19-26B.

The glenoid guide 1000 can be configured with a central channel 136 and a channel 1010 that is located peripherally. The central channel 136 extends through the hub 104. The peripheral channel 1010 extends through the outer end 164 of one of the peripheral members 108. More specifically, the glenoid guide 1000 includes a peripheral member 108R having an enlarged radially outer end with a patient specific contact surface 168 on the medial side thereof. The peripheral channel 1010 extends through the enlarged outer end from the lateral side to the medial side of the glenoid guide 1000. The central channel 136 is configured for forming a channel and or placing a central guide pin 204 as discussed above. The peripheral channel 1010 is configured for forming a rotation control feature, e.g., a visual indicator on the scapula 14 of a specific patient in a prescribed position. The prescribed position is with reference to a portion of the glenoid 18 of the specific patient to be augmented by an augmented glenoid implant, such as the baseplate 54A. For example, the position can be at an angular position spaced away from a portion of the glenoid of the specific patient to be augmented. The position can be opposite, e.g., 180 degrees offset from, a position of the glenoid to be augmented by an augmented implant. In one embodiment the peripheral member 108R is located on the anterior portion 1004 of the glenoid guide 1000. The peripheral member 108R can be located in other parts of the glenoid guide 1000, e.g., in the posterior portion 1002 or in an inferior or superior portion, or at any positions between these locations. The angular position can be based on the imaging data and analysis, e.g., upon a study of one or more CT scans, MRI scans, X-rays or the like.

FIG. 27A shows that the configuration of the peripheral channel 1010 can comprise an enclosed periphery 1012 that surrounds the peripheral channel 1010 on all sides. The enclosed periphery 1012 provide for precise guiding of a marking instrument, which is not shown but can be similar to a bovie pen. In other techniques, a marking instrument can include a drill bit or a surgical pin. The enclosed periphery 1012 results in a small symmetrical mark that can be used in guiding an inserter as discussed below. As discussed further below, the peripheral channel 1010 can be used to form a mark 1014 in an anterior (or other) portion of the glenoid 18 that is spaced away from (e.g., opposite to) a posterior (or other) portion of the glenoid 18 to be augmented using a rotationally asymmetric glenoid implant, such as the baseplate 54A. In some embodiments, the peripheral channel 1010 is 180 degrees off-set form the location of the glenoid to receive the greatest augmentation. In some embodiments, the peripheral channel 1010 is located at a different off-set position that is amenable to visual confirmation, such as 90 degrees and superior to or 90 degrees and inferior to the location of the glenoid to receive the greatest augmentation. In the glenoid guide 1000 the peripheral channel 1010 is disposed in a peripheral member 108 such that the mark 1014 is made directly on the glenoid rim 17 of the specific patient. For example, the medial end of the peripheral channel 1010 can be located on a portion of the patient specific contact surface 168 of the peripheral member 108R.

Figure 27C:
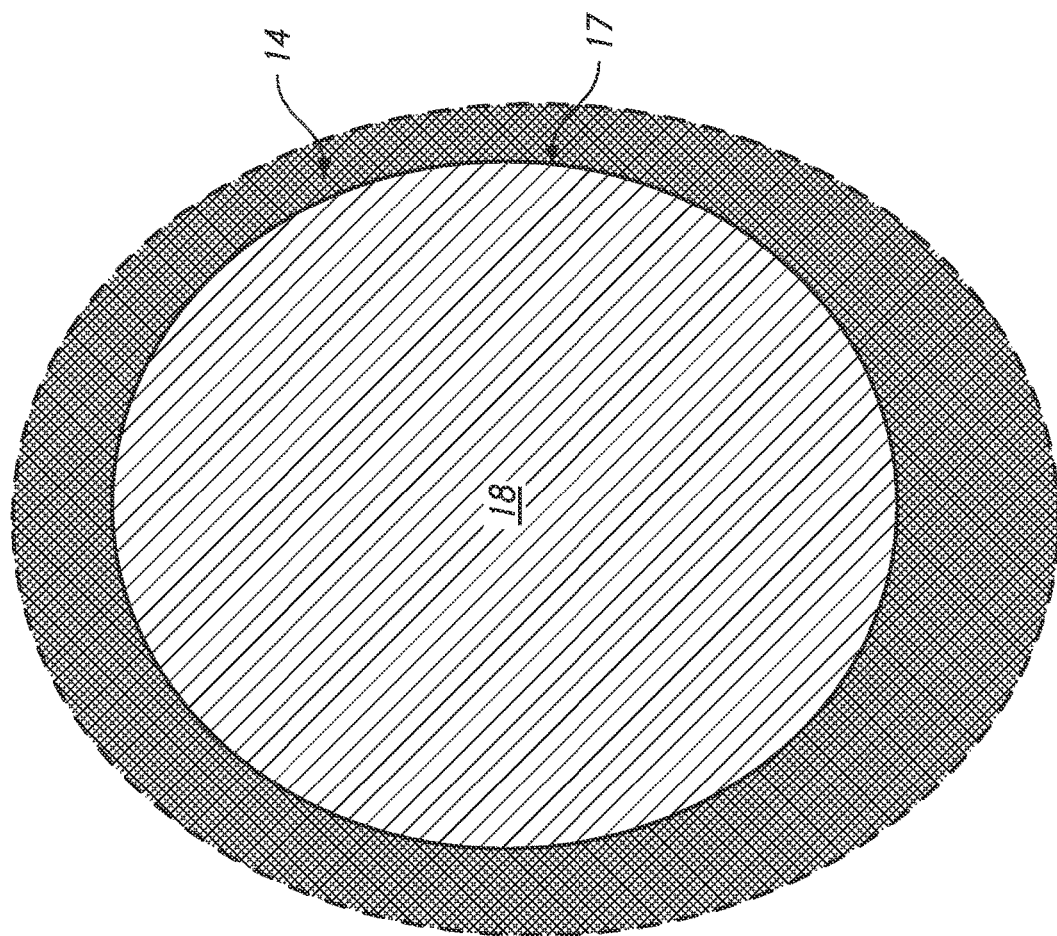
FIGS. 27C-H illustrate various methods of aligning rotationally asymmetric glenoid components using the patient specific glenoid guide of FIGS. 27A-27B.
Figure 27D:
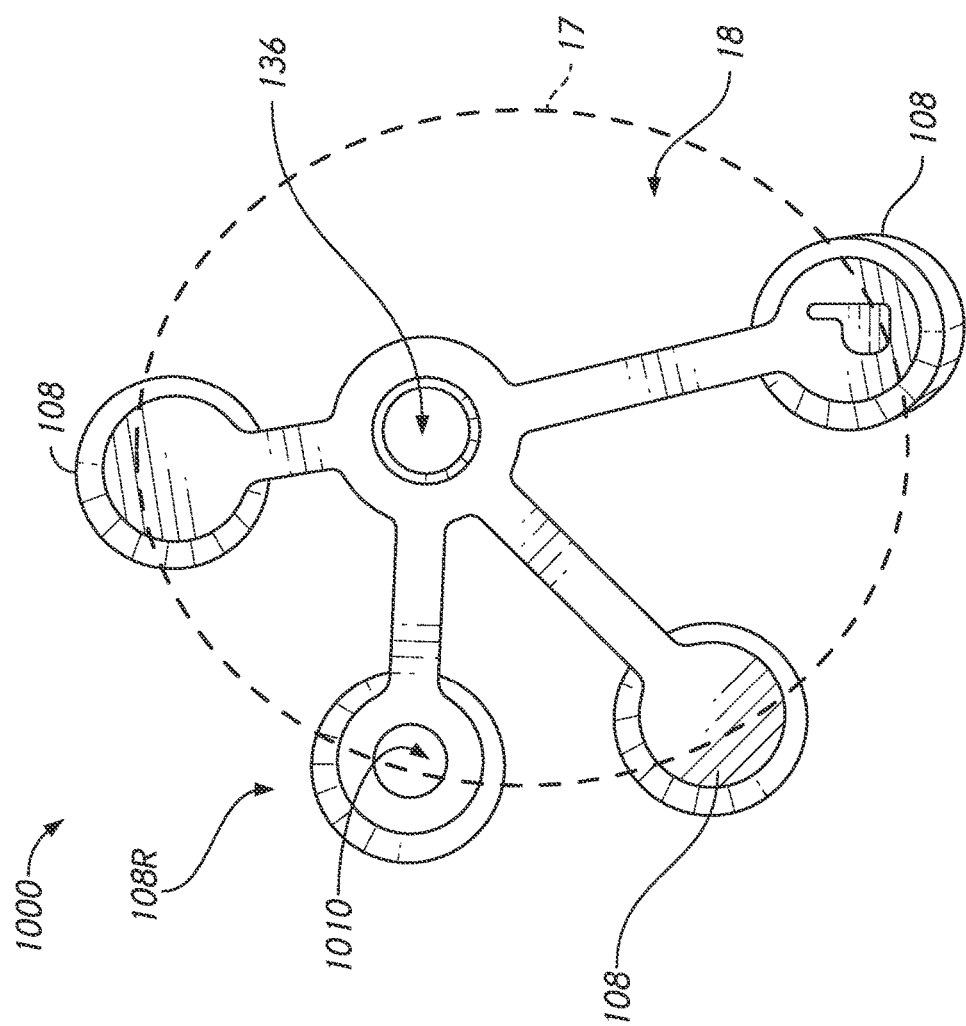

FIGS. 27C-27H illustrate methods of using the glenoid guide 1000. FIG. 27C shows relevant anatomy in a schematic form. The glenoid 18 is disposed in a lateral region of the scapula 14. The glenoid rim 17 defines a boundary that surrounds a central region of the glenoid 18. The anatomy shown schematically in FIG. 27C can be visualized after the glenoid 18 has been surgically exposed. The glenoid guide 1000 is patient specific, as discussed above, such that when the glenoid guide 1000 is applied to the glenoid 18 the peripheral members 108 are placed on the scapula 14, the glenoid 18, and in the method illustrated in FIG. 27D directly on the glenoid rim 17 in a preferred, optimal location. Application of the glenoid guide 1000 in this location can arise from forming the patient specific contact surface 168 based on imaging data of the specific patient, as discussed elsewhere herein. One of the peripheral members 108 is disposed on the posterior portion 1002 of the glenoid 18. Two peripheral members 108 and the peripheral member 108R are disposed on the anterior portion 1004.

Figure 27E:
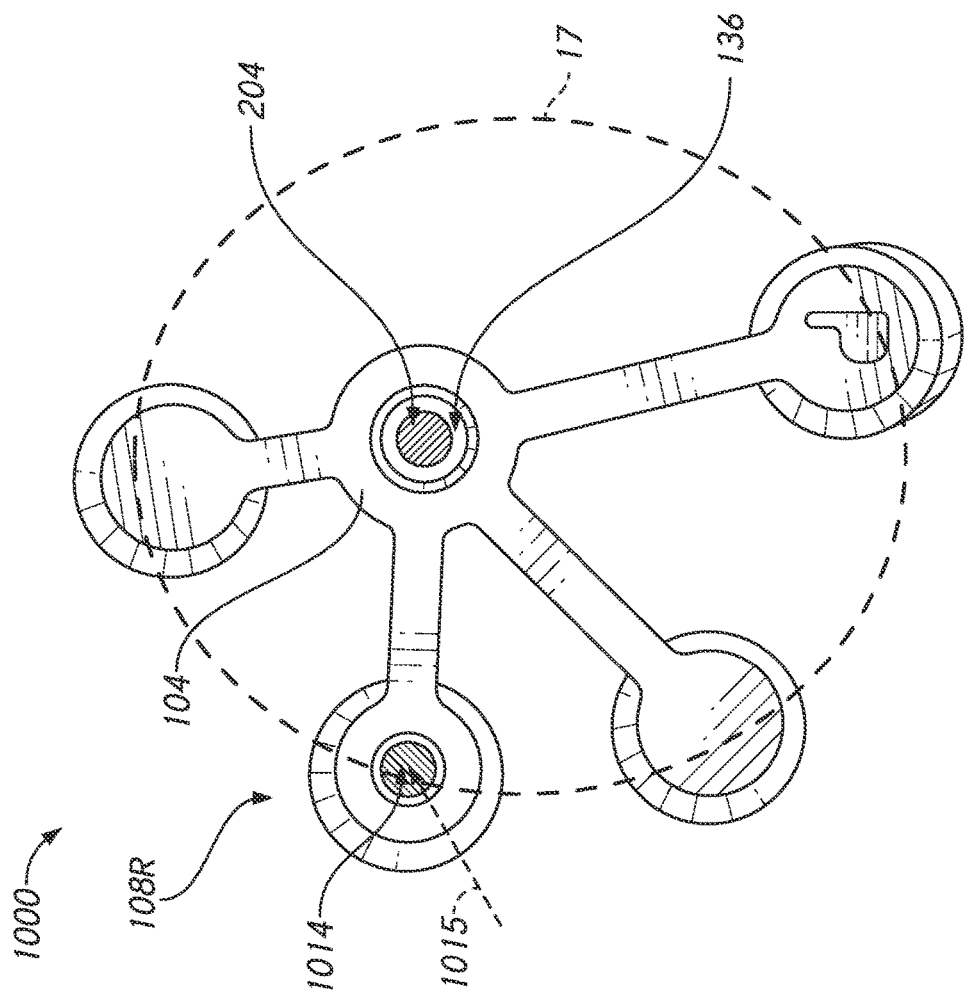

FIG. 27E shows a portion of a method involving forming a rotation control feature, in the form of a mark 2014, on the scapula 14, e.g., on or straddling the glenoid rim 17. The mark can be applied by a bovie pen 1015 which is illustrated schematically. In other techniques, the mark can be applied or made using a drill bit or a surgical pin. Also, a central mark, aperture or the central guide pin 204 can be placed using the central channel 136 as discussed above in connection with the patient specific shoulder guide 100.

Figure 27F:
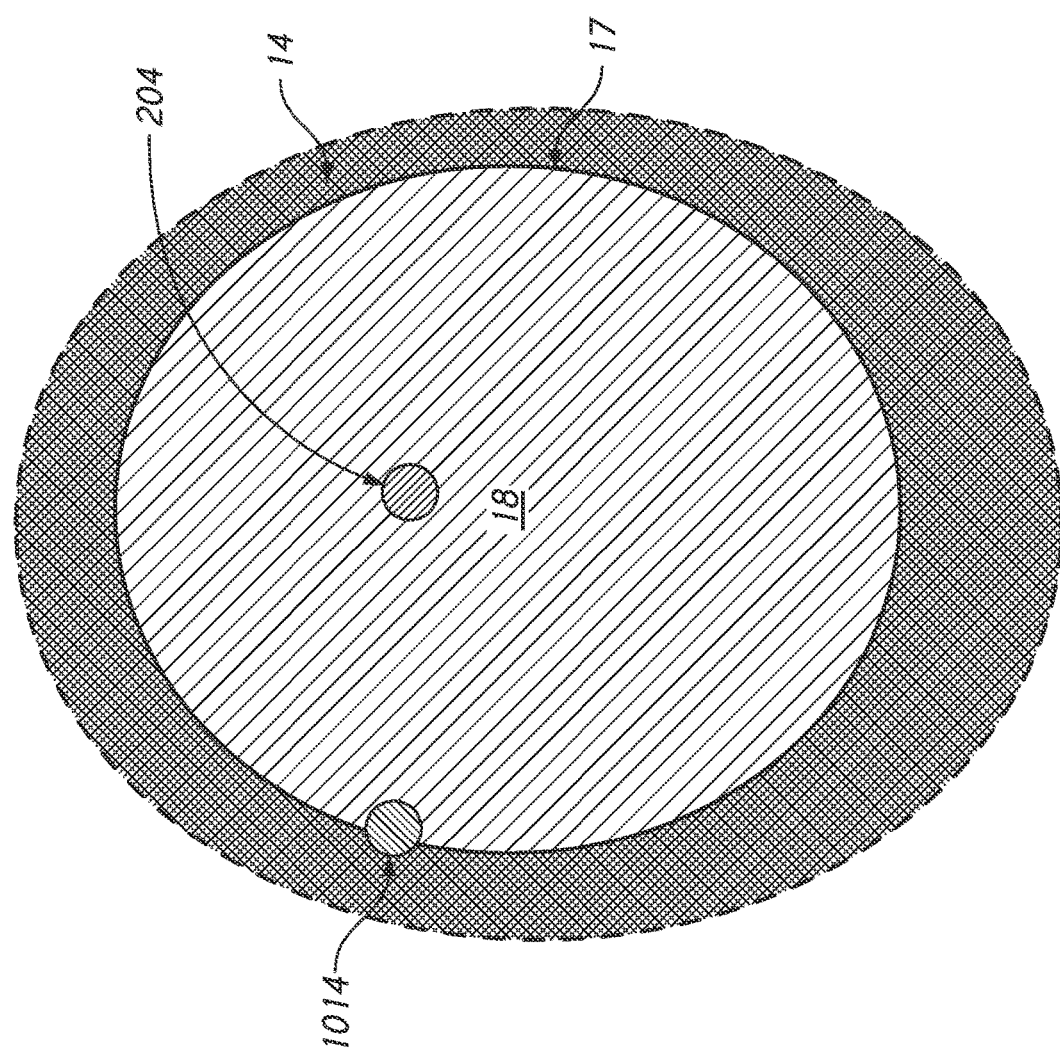
Figure 27G:
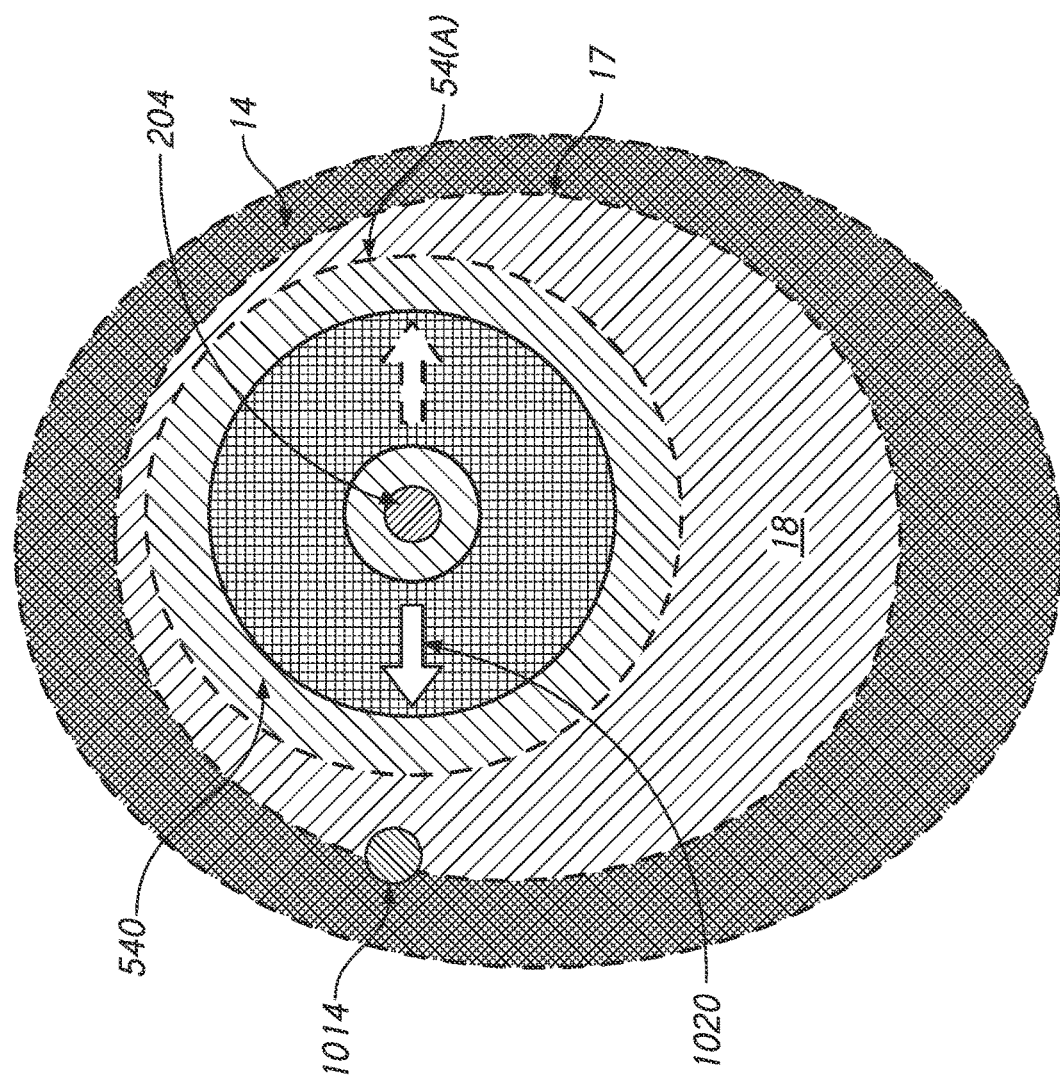
Figure 27H:
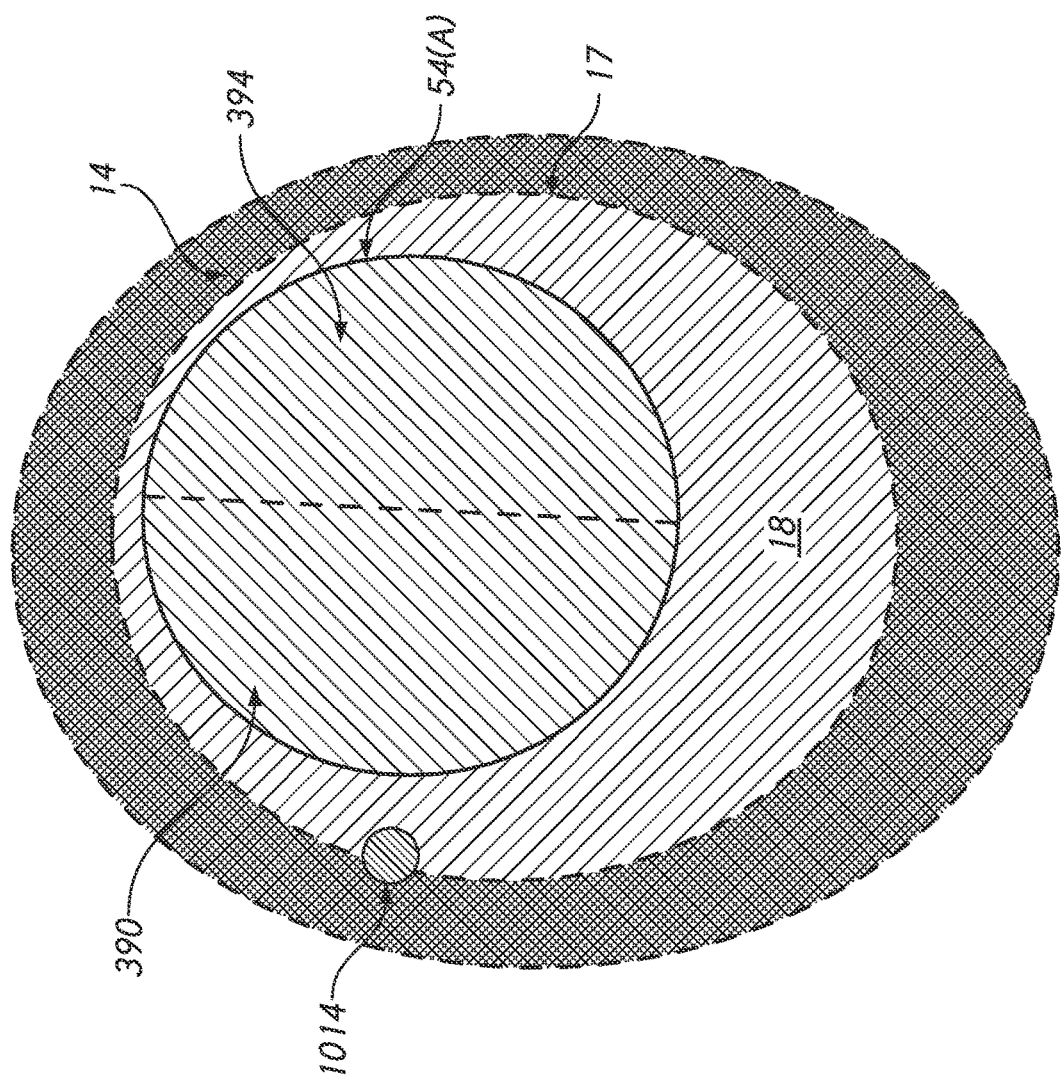

FIG. 27F shows that after the mark 1014 is made and the mark, aperture or central guide pin 204 is made or placed, the glenoid guide 1000 can be removed from the area of the glenoid 18. FIG. 27G shows that thereafter the baseplate 54A or another rotationally asymmetric implant can be delivered and secured to the glenoid 18. Although any suitable instrument can be used, the driver 540 is shown schematically with the baseplate 54A shown in dashed line. The baseplate 54A can be coupled to the driver 540 in any suitable manner, such as similar to the interaction between the outer shell 544 and the inner shell 560 to actuate the glenoid implant component retention feature 558 into a retention configuration. If the driver 540 is cannulated, the inner shaft 548 can be advanced over the central guide pin 204 which can be placed through the glenoid guide 1000. The driver 540 can include a pointer 1020 on one side. The pointer 1020 is disposed on a side of the driver 540 opposite of the side upon which the wedge portion 394 if the baseplate 54A includes the planar portion 390. If the baseplate 54A is a full wedge configuration, the thickest portion of the wedge is disposed away from the pointer 1020, e.g., at the location of the dashed arrow in FIG. 27G. With the baseplate 54A so placed, the inner shaft 548 can be rotated about a central longitudinal axis thereof to advance a screw such as the screw 577 or other central anchor can be secured in the central area of the glenoid 18. Advancing the screw 577 occurs while the pointer 1020 of the outer shell 544 continues to point at the mark 1014. The result is that the baseplate 54A remains in a rotationally stationary position, oriented according to the preoperative plan. This ensures that the wedge portion 394 of the baseplate 54A is aligned to the posterior side away from the location of the glenoid guide 1050. FIG. 27H shows this result after the driver 540 has been removed. In the illustrated embodiment, the thickest portion of the baseplate 54A, e.g., the wedge portion 394 is disposed posteriorly and somewhat inferiorly of the thinnest portion the baseplate 54A in the case of a full wedge baseplate. In the case of a partial wedge baseplate 54A such as where the augment is only on one-half (or less) of the baseplate 54A, as much as 180 degrees (or more) of the baseplate 54A will have the same thickness in the non-augmented periphery and each portion along the non-augmented periphery will correspond to the least thickness of the baseplate 54A. For partial wedge baseplates, the thickest portion of the baseplate 54A can be disposed posteriorly and somewhat inferiorly of the center of the circumference of the non-augmented periphery using the method illustrated in FIGS. 27A-27H. These positions and orientations are as prescribed from pre-operative imaging. In some cases, the boundary between the wedge portion 394 and the planar portion 390 can be at an angle to the superior-inferior plane of the glenoid 18, as prescribed from pre-operative imaging.

The mark 1014 is illustrated as being used to rotationally orient the baseplate 54A during insertion thereof. The mark 1014 can also be used to guide the advancement of the reamer 404 either free-hand or over the guide pin 204. A pointer on the reamer 404 can be aligned with the mark 1014 to cause the reaming head 412 to be in a desired position, e.g., a pre-determined amount off-set therefrom e.g., 180 degrees off-set therefrom. In further variations, the guide pin 208 can be placed through the channel 1010 and the reaming guides 432, 432A can be configured to mate with the pin 208 so placed.

Figure 28A:
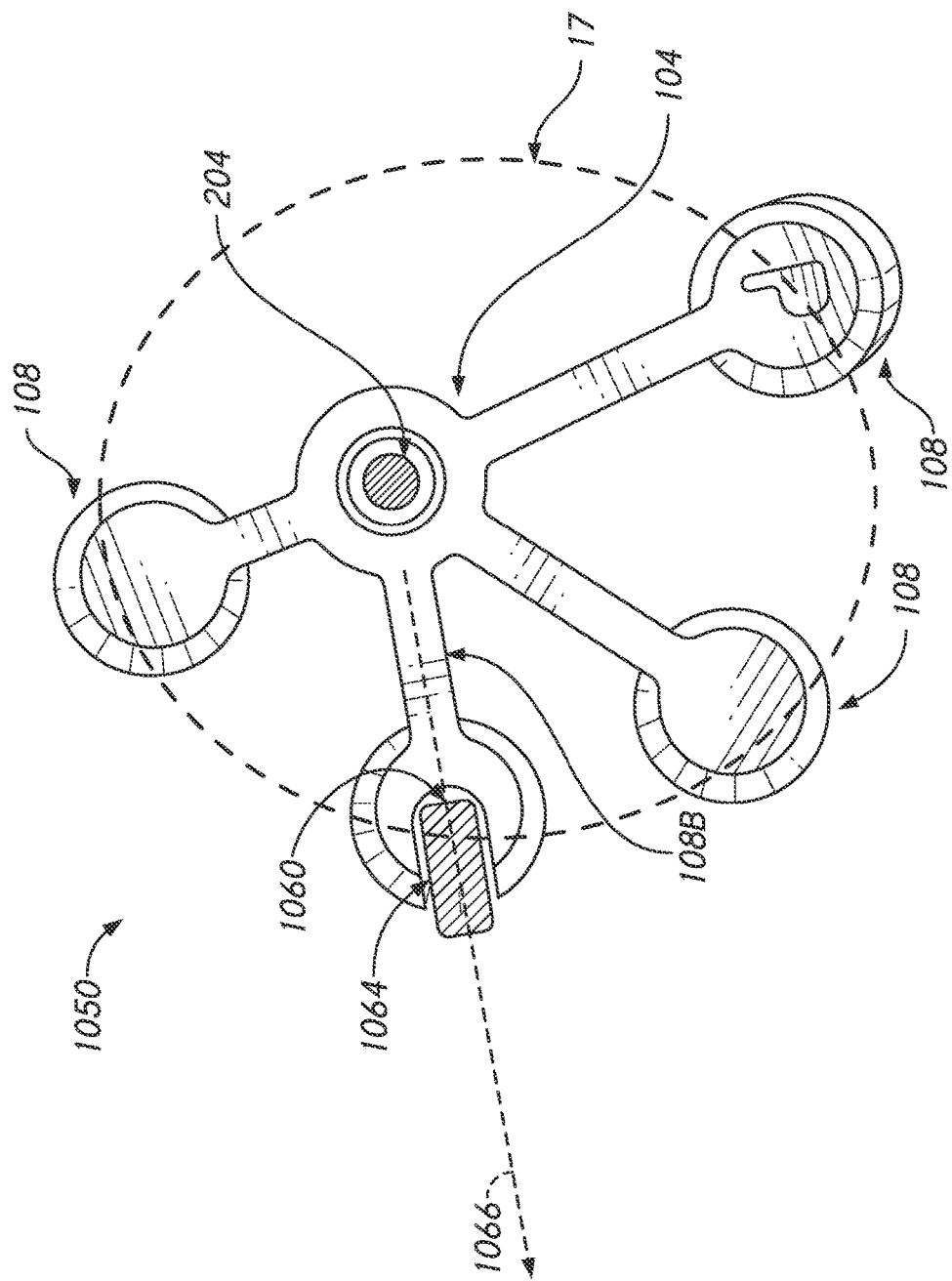
FIG. 28A is a lateral side view of another embodiment of a patient specific glenoid guide configured for forming a rotation control feature.
Figure 28B:
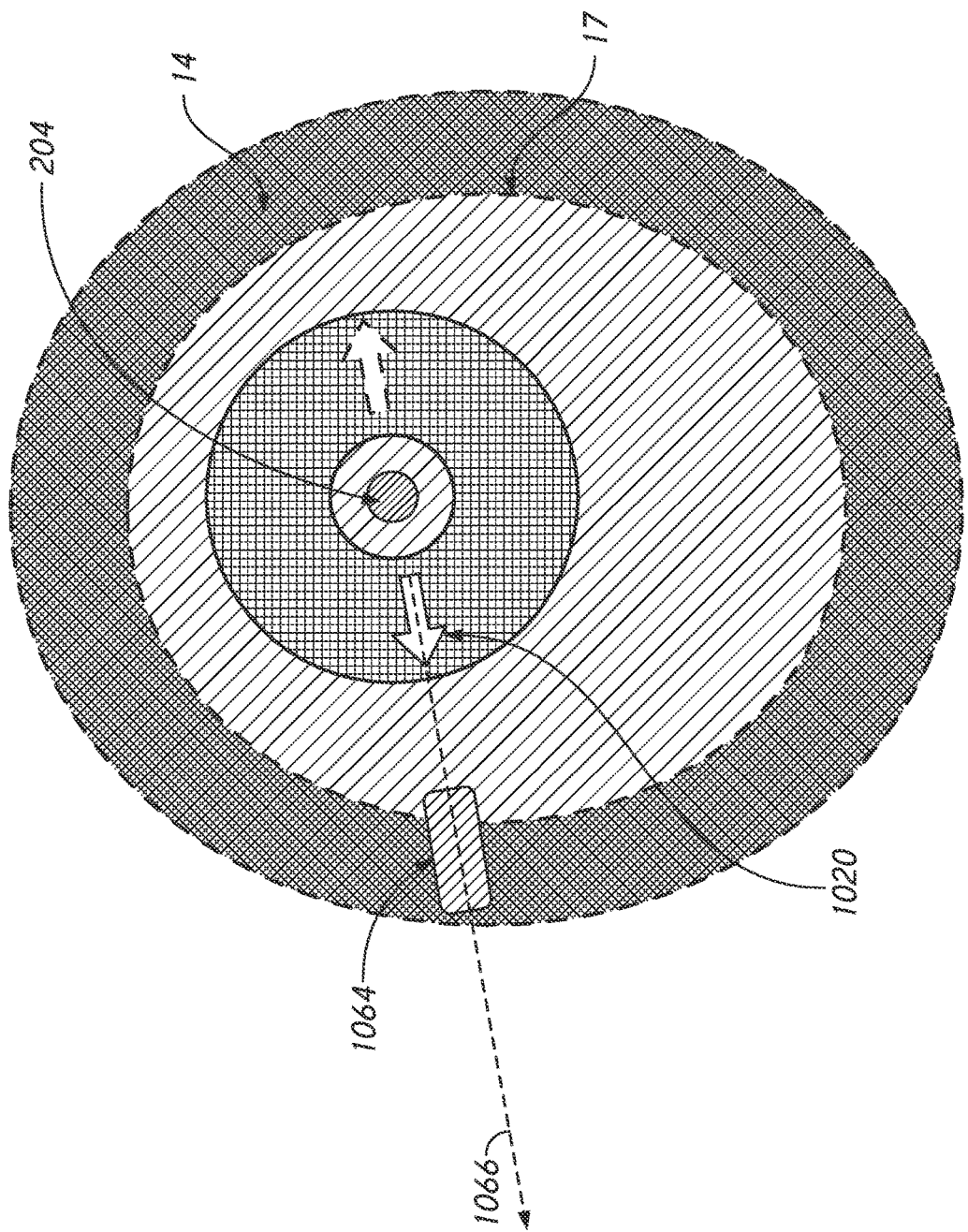
FIG. 28B illustrates various methods of aligning rotationally asymmetric glenoid components using the patient specific glenoid guide of FIG. 28A.

FIGS. 28A and 28B illustrate a glenoid guide 1050 that is similar to the glenoid guide 1000 except as described differently below. The glenoid guide 1050 includes a plurality of peripheral members 108 and also includes a peripheral member 108B configure for forming a mark 1064 or other rotation control feature. The peripheral member 108B provides a channel 1060 for making the mark 1064. Unlike the peripheral channel 1010, the channel 1060 is open on one side. The channel 1060 is enclosed on a side radially between the hub 104 and the radially outer-most portion of the peripheral members 108. The channel 1060 is open on the outermost radial periphery of the peripheral member 108B.

One advantage of the glenoid guide 1050 is that by providing an open channel 1060, the mark 1064 can be elongate. For example, the mark 1064 can be formed by directing a marker along the enclosed wall of the channel 1060 until the marker contacts the scapula 14. The marker can then be moved in a direction along the axis of the peripheral member 108B as shown by the arrow 1066 to configure the mark 1064 as elongated in the direction of the arrow 1066. The elongated form of the mark 1064 can enhance the ability of the surgeon to accurately align the pointer 1020 with the mark 1064, further enhancing the alignment of the wedge portion 394 of the baseplate 54A (or more generally the thickest portion) with the angled reamed surface R2 or other portion of the glenoid 18 that would benefit from the greatest amount of augmentation.

The mark 1064 can also be used to guide the advancement of the reamer 404 either free-hand or over the guide pin 204. A pointer on the reamer 404 can be aligned with the mark 1064 to cause the reaming head 412 to be in a desired position, e.g., 180 degrees off-set therefrom. In further variations, the guide pin 208 can be placed through the channel 1060 and the reaming guides 432, 432A can be configured to mate with the pin 208 so placed.

As discussed above, in connection with the patient specific shoulder guide 100, the glenoid guide 1000 and the glenoid guide 1050 can be formed using a protocol in which patient specific imaging information is gathered and processed. The processing can include inputs from the surgeon such as whether the surgeon wishes to use a bovie pen, drill bit, pin or the like to create a visual reference opposite the portion of the glenoid to be most augmented. The processing can include determining whether features can be formed in one of the peripheral members 108 configured to make patient specific contact with the glenoid rim 17 or should be disposed in a separate peripheral member. In one approach, the rotational position of one of the peripheral members 108 can be selected to be opposite to, e.g., 180 degrees off-set from the portion of the glenoid to be most augmented. Next either the surgeon or the protocol determines whether to form an enclosed channel, as in the peripheral channel 1010, or an open sided channel or slot, as in the channel 1060, in the peripheral member 108R. Next the protocol can output plans for forming the glenoid guide 1000 or the glenoid guide 1050. Upon outputting the plans, the glenoid guide 1000 or the glenoid guide 1050 can be produced using a preferred facility such as additive manufacturing or other guide forming process. In some embodiments a kit including at least the glenoid guide 1000 and the glenoid guide 1050 can be formed such that the surgeon can select whether to use a closed channel or an open channel, e.g., a slot to form a bovie mark on or a channel in or to place a pin in the bone.

V. Enhanced Access Glenoid Guides

Figure 1:
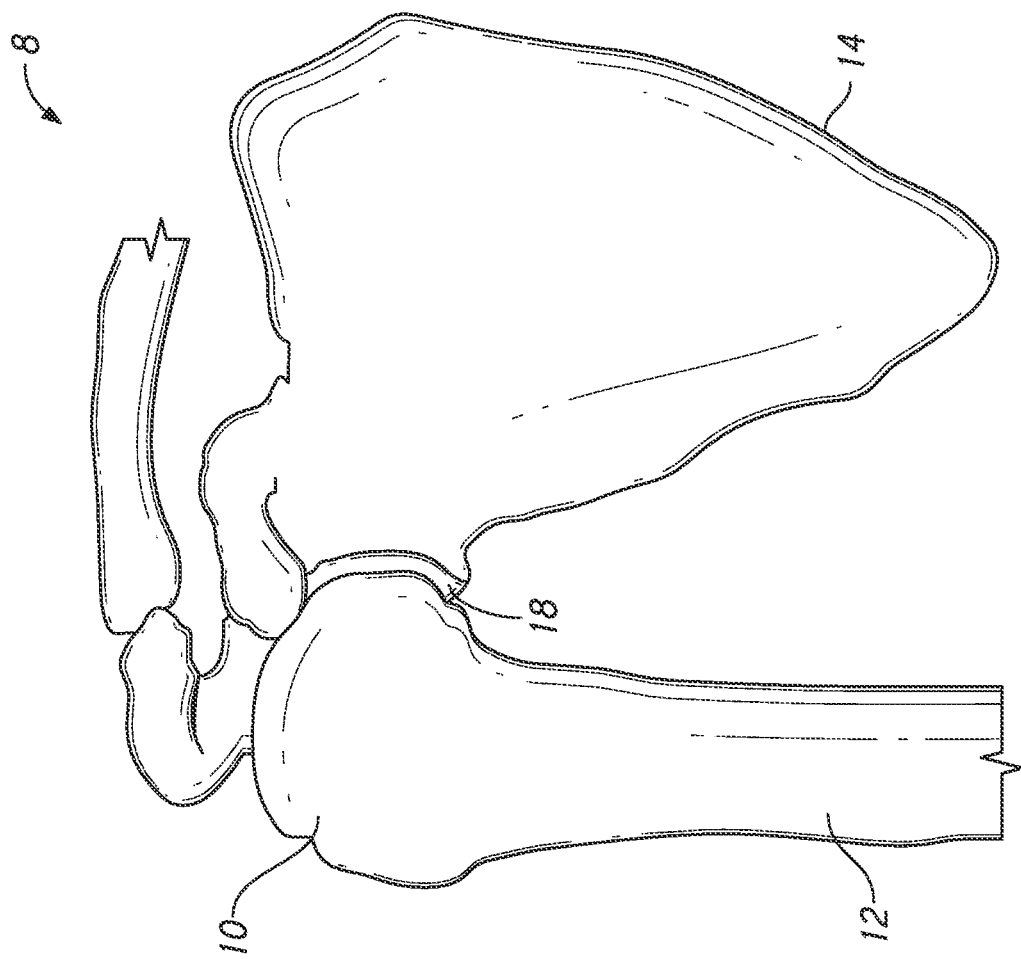
FIG. 1 is a schematic view of a human shoulder joint showing the bones thereof.
Figure 1A:
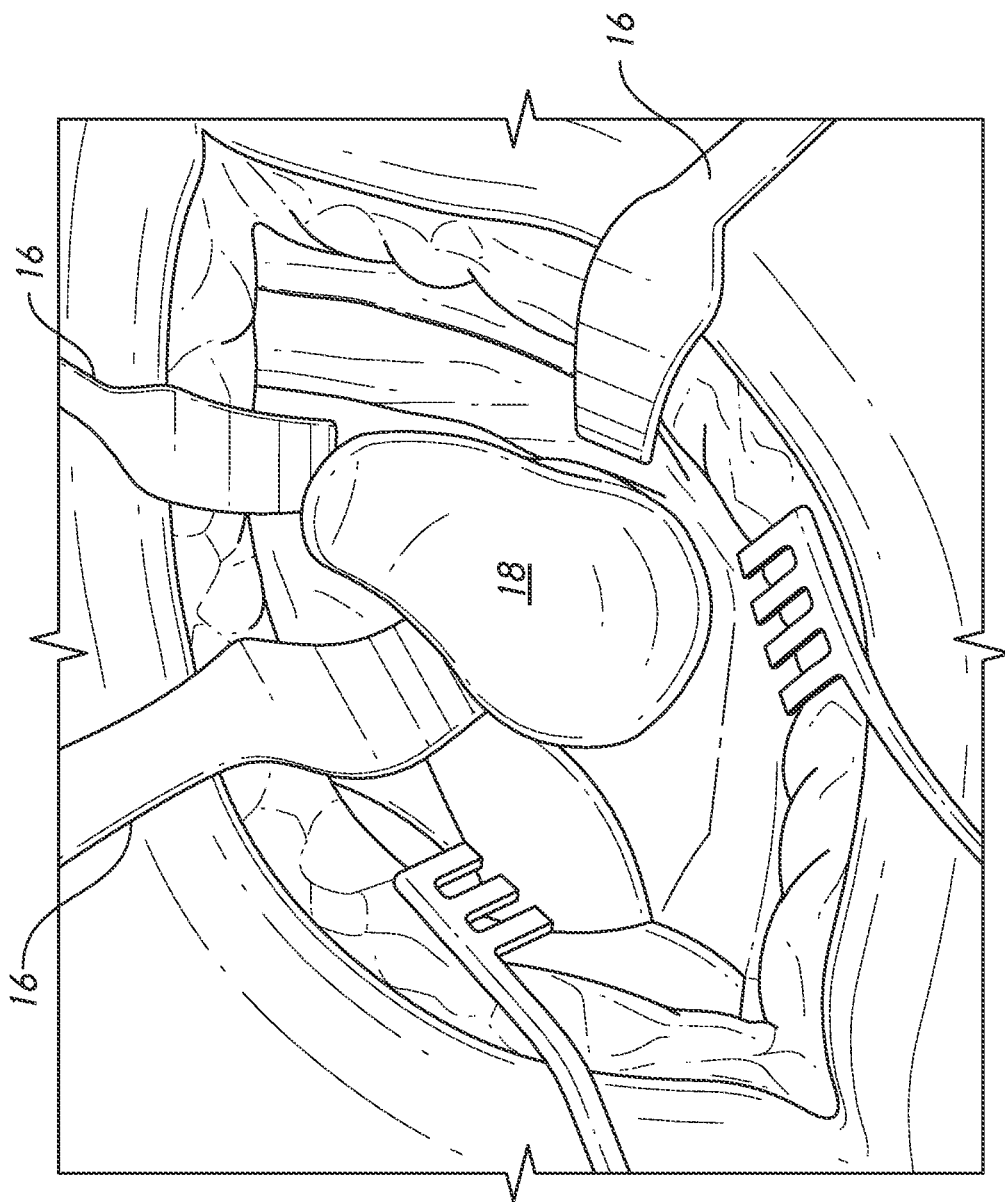
FIG. 1A is a schematic view of the glenoid surface of a scapula, access to which has been enhanced by retractors.
Figure 19:
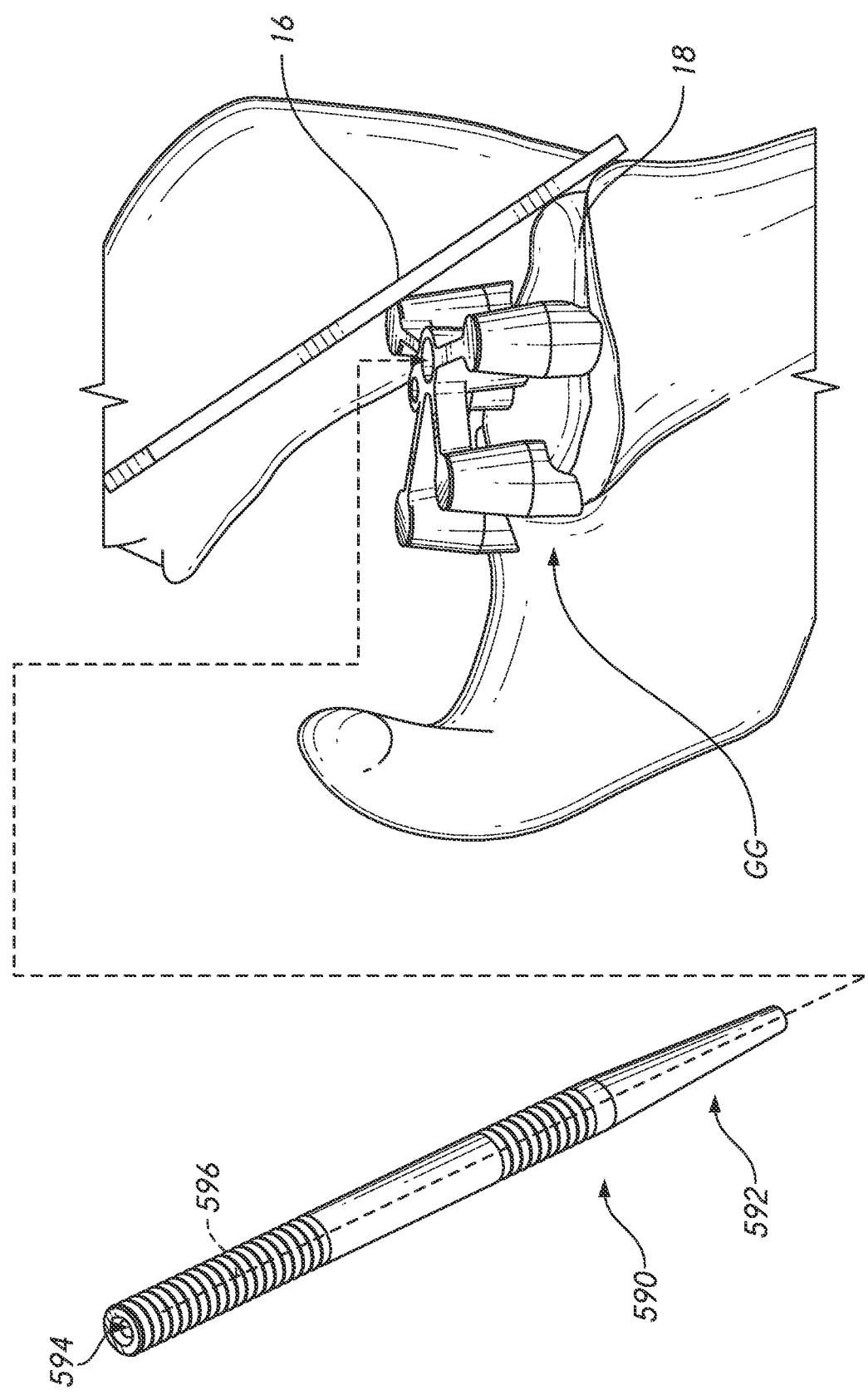
FIG. 19 is a side view of a scapula showing potentially disruptive interaction between a retractor and a glenoid guide.

FIGS. 1, 1A and 19 illustrate challenges of surgically accessing the glenoid 18 with a glenoid guide GG, which can be patient specific. The glenoid guide GG can be configured with at least a portion that extends toward the posterior side of the glenoid 18. The glenoid guide GG is adapted to mate with a pin guide 590. The pin guide 590 includes an elongate body having a tapered distal portion 592 that extends proximally from a distal end thereof. The tapered distal portion 592 can mate with a tapered central channel of the glenoid guide GG. The pin guide 590 includes a pin guide lumen 594 that can be aligned with the channel in the glenoid guide GG. The pin guide 590 enables the central guide pin 204 or other pin (e.g., a Steinmann pin, a K-wire, or another similar slender but rigid guide pin) to be placed along a longitudinal axis 596 of the pin guide 590. When placed on the glenoid 18, the glenoid guide GG stands at a height above the surface of the glenoid 18. The height of the glenoid guide GG is uniform throughout the guide. The height of the glenoid guide GG affects the stability of the pin guide 590. By increasing the height of the glenoid guide GG, a larger interface between the pin guide 590 and the central channel of the glenoid guide GG can be provided for increased stability. However, increased height may result in interference between the glenoid guide GG and the retractor 16 or other instruments, which can result in damage or displacement of the glenoid guide GG from the proper orientation.

Figure 21A:
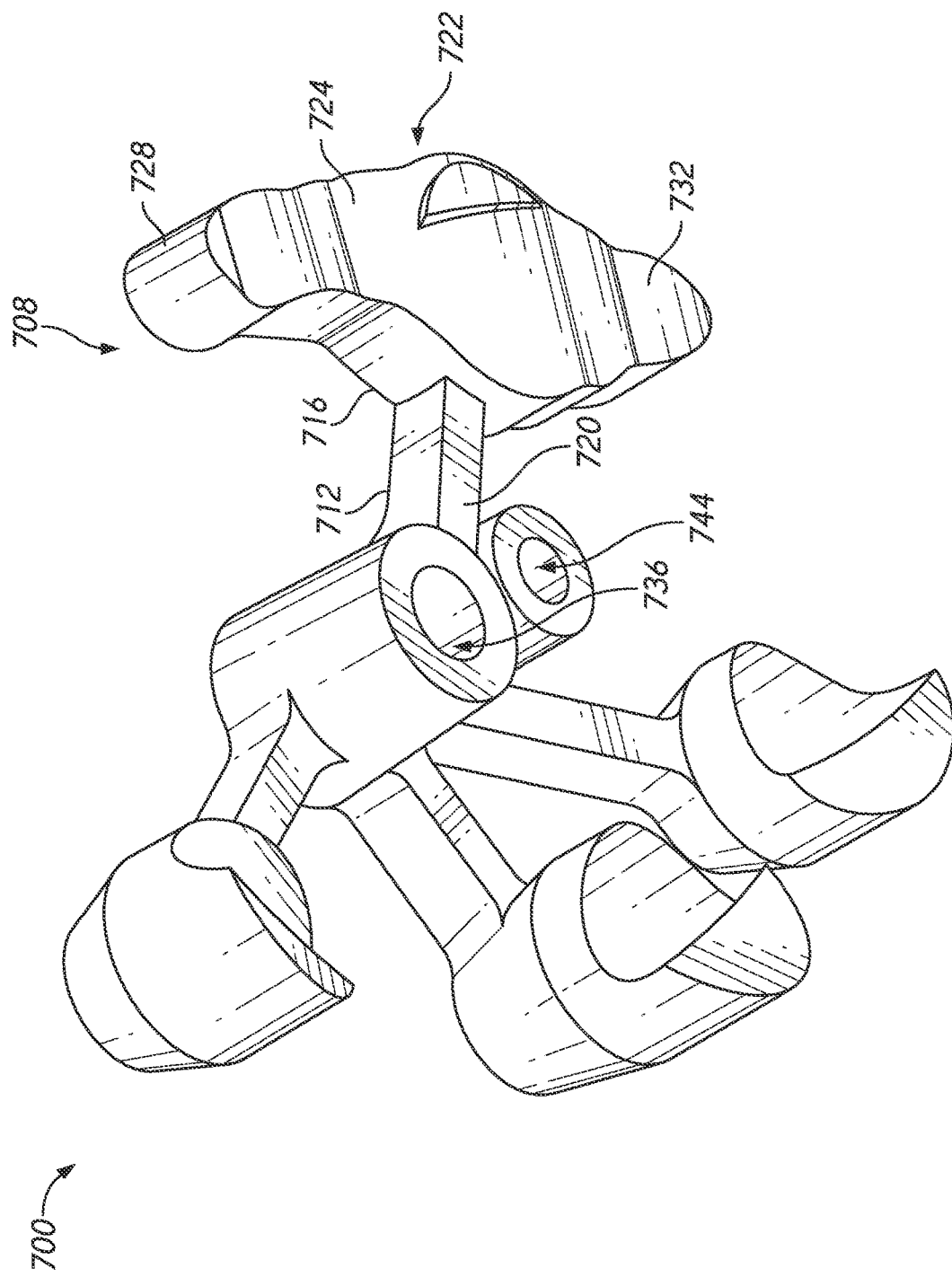
FIG. 21A is a medial or distal side view of the glenoid guide of FIG. 21.
Figure 21B:
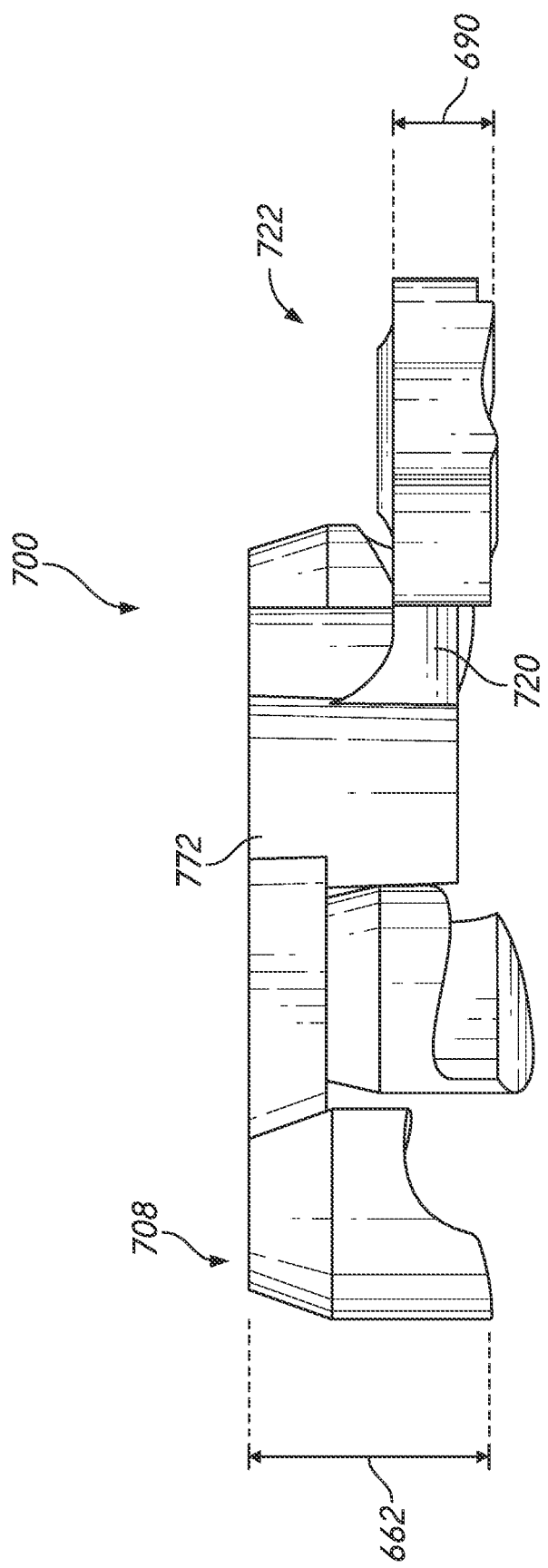
FIG. 21B is a side view of the glenoid guide of FIG. 21.
Figure 22:
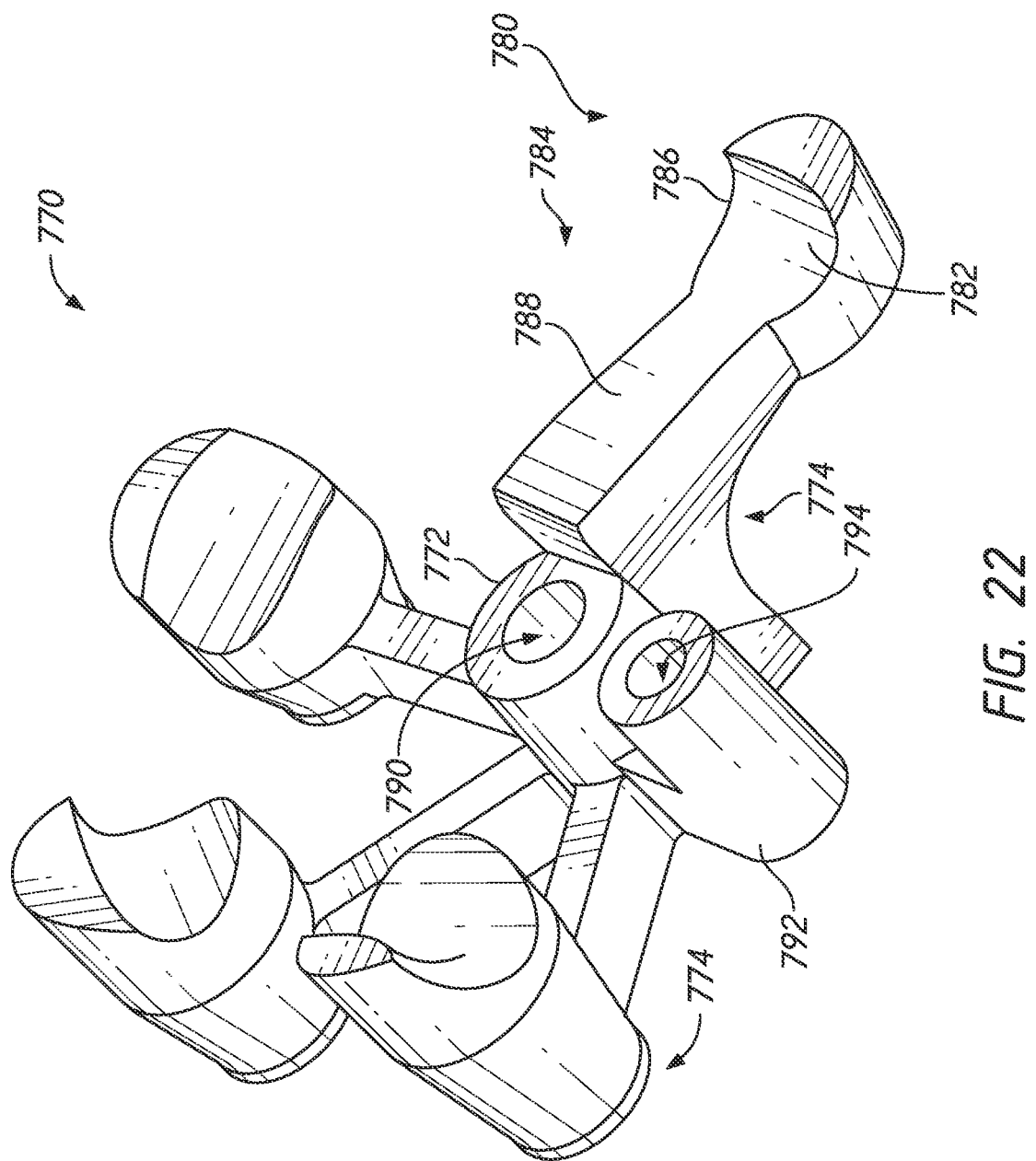
FIG. 22 is a medial or distal side view of another embodiment of a low profile glenoid guide providing improved clearance for a tissue retractor.
Figure 22A:
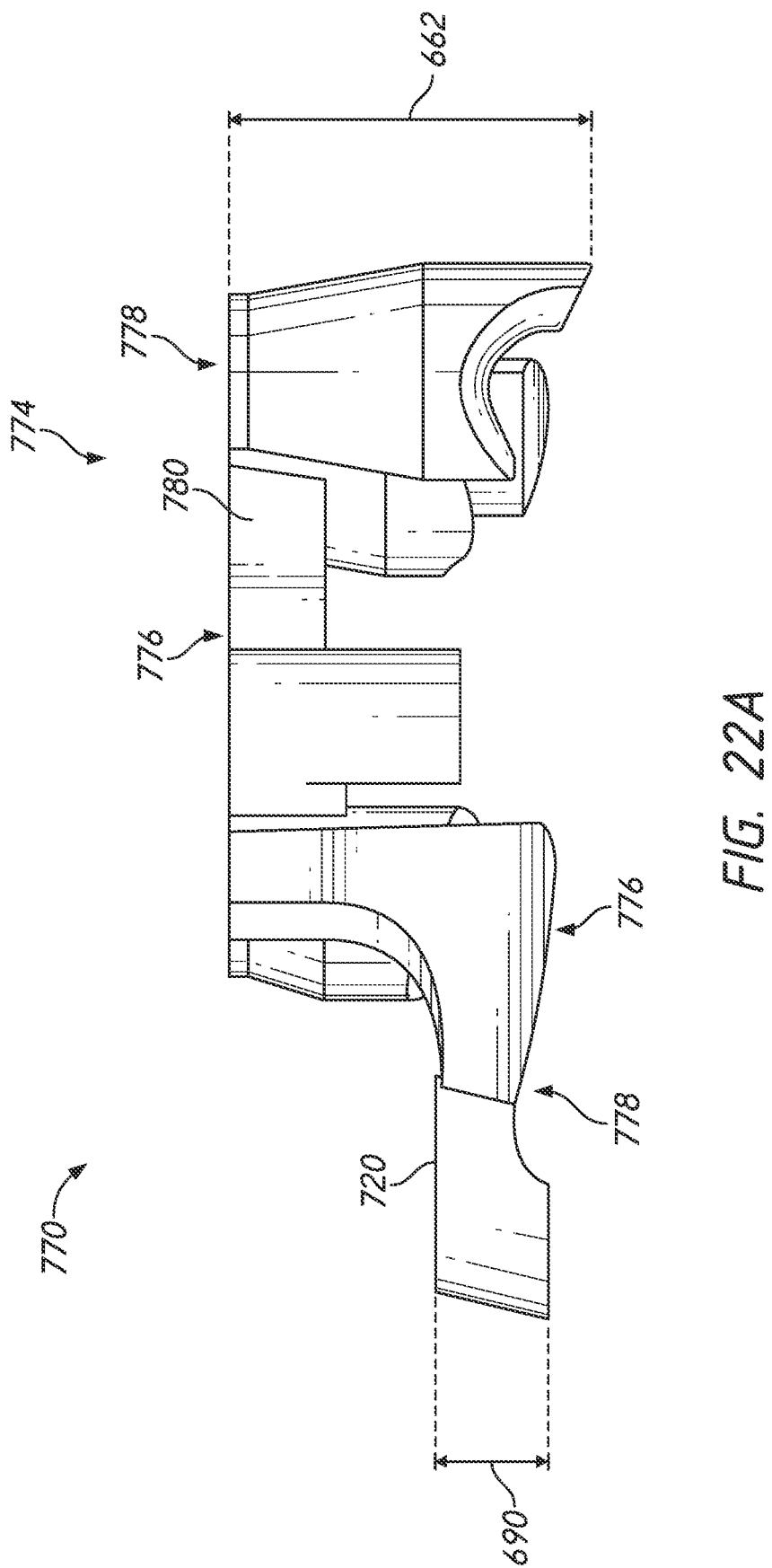
FIG. 22A is a side view of the glenoid guide of FIG. 22.
Figure 23:
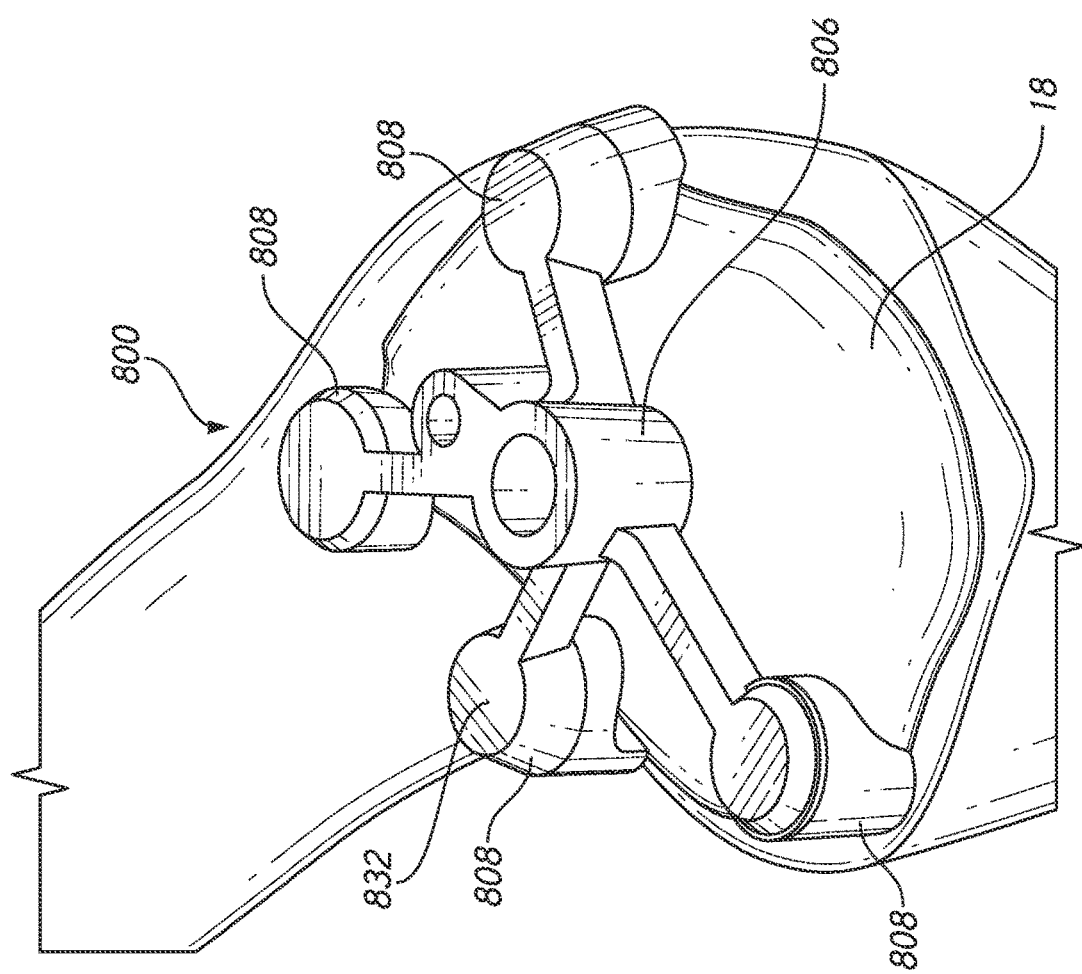
FIG. 23 is a lateral or proximal side perspective view of another embodiment of a low profile glenoid guide placed on a scapula, the guide providing improved clearance for a tissue retractor.

FIGS. 20-26 show embodiments of glenoid guides that provide enhanced access in the surgical field around the glenoid 18. These guides can be patient specific. As discussed above in connection with the guide 100, the guides herein described below can have central and peripheral members. The size and/or placement or orientation of the central or peripheral members or the gross dimensions of the guides described below can be patient specific. Medial bone contacting surfaces of the guides described below can be patient specific, e.g., having complementary form that may be concave or otherwise a substantial negative of specific underlying bone. As above-described, pre-operative scans can be utilized to configure patient specific surfaces to be complementary, e.g., negative, surfaces of the bone to which they are to mate such that the guide is seated according to the optimized fit as determined by the surgeon. The guides can be low profile in a number of different ways. For example, FIGS. 20-22A show guides in which a portion that extends into a posterior region of the glenoid 18 when applied has a lesser height, lesser length, e.g., extends a lesser amount in a direction away from the glenoid (e.g., in a vertical direction if the patient is placed on his or her side) when compared to at least some other portions of the guides. As used herein, the term "low profile" refers to this and other aspects in which the guides herein can be confined out of the way of other instruments to be used in the procedure. FIGS. 23-24B show guides where a plurality of peripheral members is of a low profile and a central portion extends above or below the members to mate in a stable manner with the pin guide 590. FIGS. 24-24B illustrate guides in which a posterior portion is shorter than in other configurations herein and thus can be configured to mate with a glenoid surface disposed inward of a glenoid rim. FIGS. 25A-26B illustrate guides with peripheral members configured to contact a glenoid structure are disposed in an anterior portion but not in a posterior portion of the guide.

A. Low Profile Glenoid Guides Having Reduced Proximal Height Features

FIGS. 20-22A show guides in which a portion that extends into a posterior region of the glenoid 18 when applied extends a lesser amount in a lateral direction (away from the surface of the glenoid) when compared to at least some other portions of the guides. In other words, a portion of the glenoid guide occupies less space with regard to at least one length dimension or distance (e.g., radial length, height, and/or circumferential width) compared to other portions of the guides. The glenoid guides can extend proximally or laterally a lesser amount in an anterior portion, in a posterior portion, in an inferior portion, or in a superior portion than other portions. For example, a posterior portion of the surgical field can be made less obstructed by limiting the lateral extent, length, distance or height of glenoid contact points of a guide.

Figure 20:
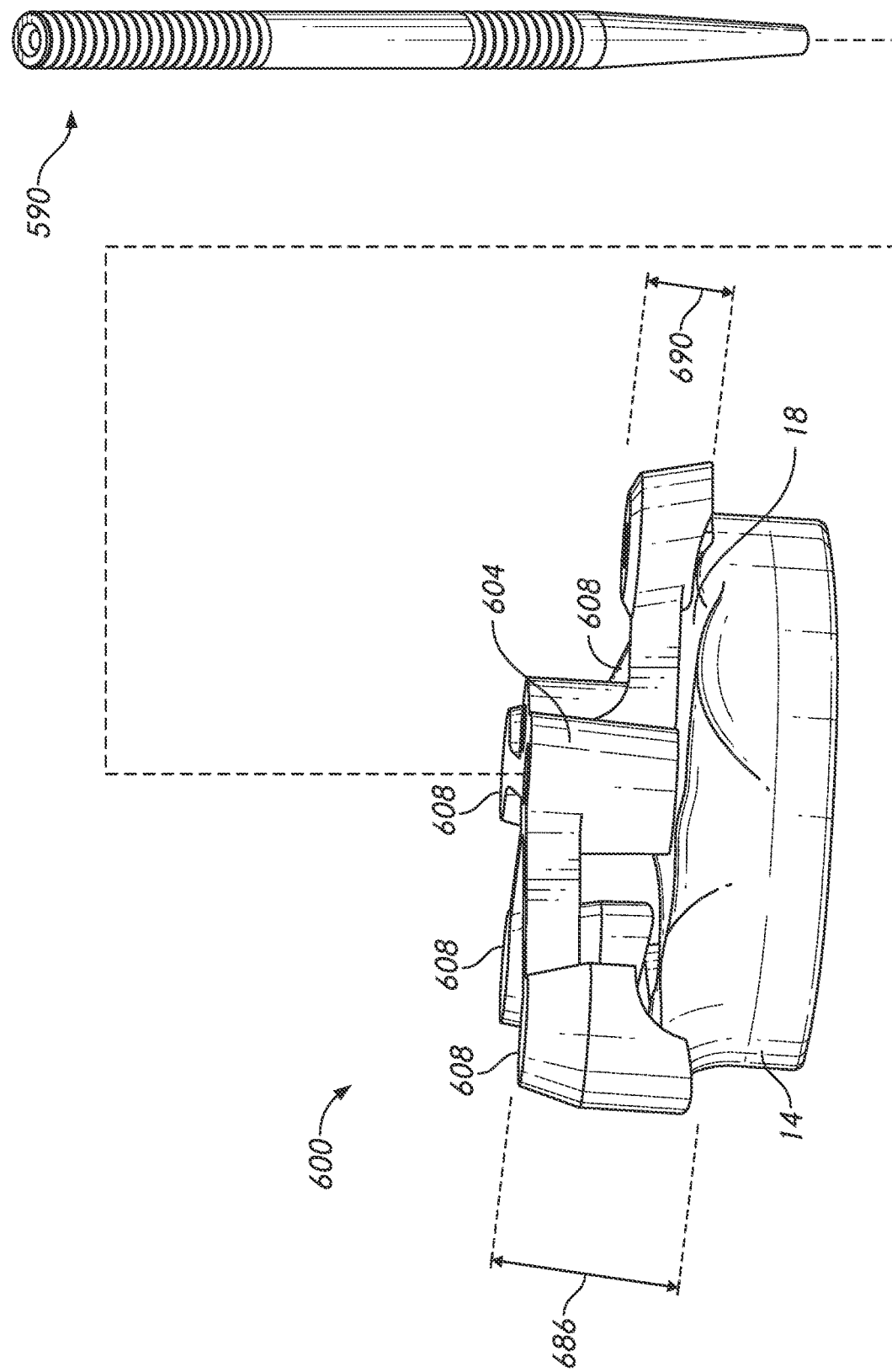
FIG. 20 shows a side perspective view of one embodiment of a low profile glenoid guide providing improved clearance for a tissue retractor.
Figure 20B:
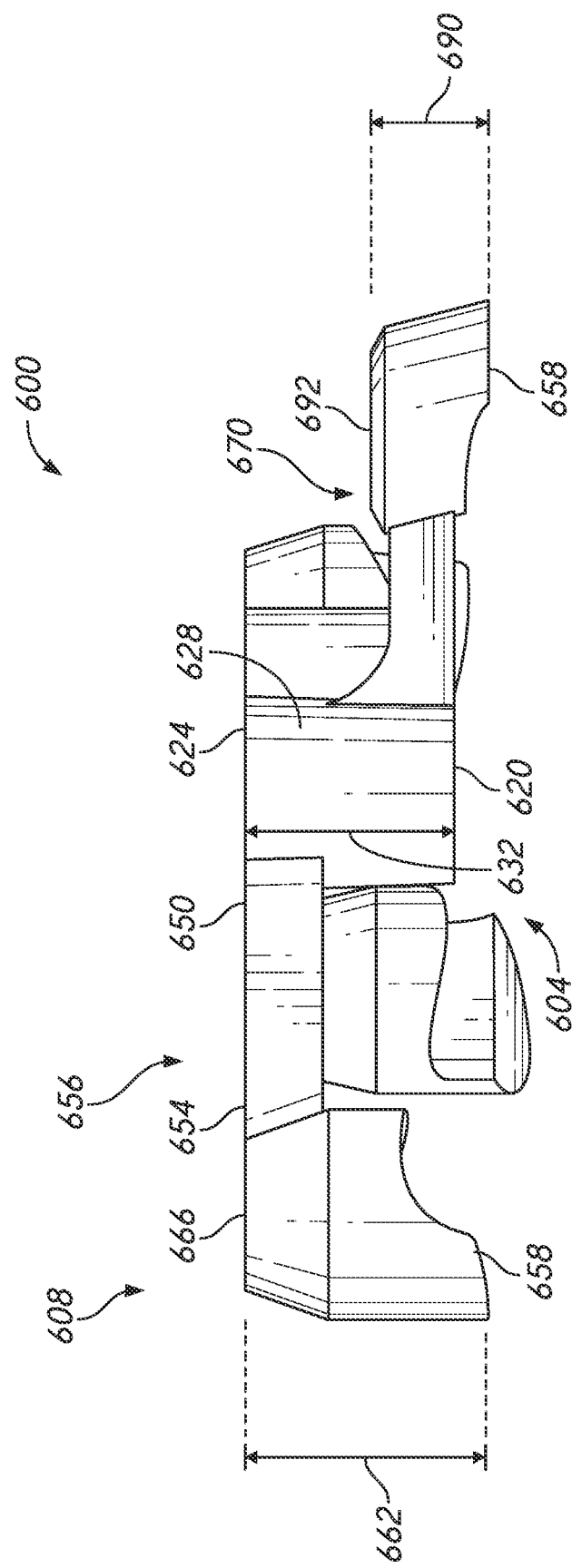
FIG. 20B is a side view of the glenoid guide of FIG. 20.

FIGS. 20-20B show a patient specific shoulder guide 600 that is configured to provide enhanced access for instruments such as the retractor 16 that is or are disposed posteriorly of or over a posterior portion of the shoulder guide 600. The shoulder guide 600 is shown on a schematic representation of a glenoid 18 of a scapula 14. By enhancing access to the anatomy around a posterior portion of the glenoid 18 (and also posterior thereto), the guide 600 enables the use of the retractor 16 and other instruments without interference between the patient specific shoulder guide 600 and such instruments.

The patient specific shoulder guide 600 includes a hub 604 and a plurality of peripheral members 608. The peripheral members 608 can be dispersed into a posterior portion 612 and an anterior portion 616 of the patient specific shoulder guide 600. In one embodiment, there is a plurality of (e.g., three) peripheral members 608 in the anterior portion 616 and there is at least one (e.g., only one) one peripheral member 608 in the posterior portion 612. The posterior portion 612 can be defined as the portion of the patient specific shoulder guide 600 that would align with a posterior side of the glenoid 18 when applied to a specific patient. The posterior portion 612 can be to the posterior side of a plane intersecting the hub 604 and extending generally superior and inferior when the patient specific shoulder guide 600 is applied to a patient. The patient specific shoulder guide 600 that is depicted would be suitable for a left shoulder joint of a specific patient.

As discussed further below, some embodiments can have as few as three contact points, e.g., three peripheral members 608 to define a stable position. Also in some embodiments, the shoulder guide 600 has no more than three peripheral members 608. A fourth contact point, e.g., a fourth peripheral member 608 of a fourth contact point in the articulating surface of the glenoid, provides an advantage of confirming that the patient specific shoulder guide 600 is properly positioned. For example, in an embodiment having four peripheral members, if a user were to find that only three of four contact points made contact one can conclude that a problem has arisen, such as the patient specific shoulder guide 600 is not properly positioned, has been distorted, etc.

FIGS. 20A and 20B shows that the hub 604 includes a first end 620 and a second end 624. The first end 620 is configured to face a central surface of the glenoid 18. The second end 624 is disposed oppose the first end 620, e.g., away from the glenoid 18. A hub body 628 extends between the first end 620 and the second end 624 and defines a hub height dimension 632. The hub 604 includes a central channel 636 disposed therethrough. The central channel 636 can be coupled with the pin guide 590 to provide a guide conduit that includes the pin guide lumen 594 and may include a portion extending through the central channel 636. In some embodiments of the patient specific shoulder guide 600 and of the other glenoid guides disclosed herein it is desired to provide the hub height dimension 632 above a threshold or minimum dimension. In some embodiments, the second end 624 is disposed at the proximal most part of the patient specific shoulder guide 600. Maintaining the hub height dimension 632 above a minimum dimension ensures that the contact region with the pin guide 590 is sufficient to reduce, minimize or eliminate deviation of the longitudinal axis 596 (and thus the trajectory of the pin placed through the pin guide 590) from the intended trajectory. The hub height dimension 632 can be maintained the same or can be no shorter than sufficiently long to provide this control of the intended trajectory.

The peripheral members 608 can each include an inner end 650, an outer end 654 and an elongate member 656 extending therebetween. A structure forming a patient specific contact surface 658 can be coupled with or can extend from or comprise a portion of the outer end 654. FIG. 20B shows that the patient specific contact surface 658 can be highly contoured to receive, to mate with, to follow, and in some cases to be formed as a negative of a natural bone surface of glenoid 18. The patient specific contact surface 658 can be highly contoured to receive, to mate with, to follow, and in some cases to be formed as a negative of a portion of the rim of the glenoid 18, an osteophyte other protuberances of the rim or other portion of or adjacent to the glenoid 18, or another portion of the scapula 14 close to the rim of the glenoid 18. A peripheral member height dimension 662 can be defined in a proximal-distal direction (which also is a medial-lateral direction away from the glenoid 18 when applied to the patient). The peripheral member height dimension 662 can be measured in one embodiment as the distance between a distal-most aspect of the patient specific contact surface 658 and a side 666 of the patient specific shoulder guide 600 opposite the patient specific contact surface 658.

In one embodiment, the patient specific shoulder guide 600 is formed by additive manufacturing. A high profile portion of the shoulder guide 600 provides a co-planar relationship between the second end 624 of the hub 604 and adjacent sides of each of a plurality of the peripheral members 608. These co-planar portions can be disposed on the same side 666. In one embodiment, the entire sided side 666 of the patient specific shoulder guide 600 is on a common plane other than a low profile portion. The low profile portion can include a low profile peripheral member 670. The low profile peripheral member 670 can include an inner portion 674 and outer portion 678 and an elongate member 682 that extends therebetween. At least the outer end 678 and preferably the entire low profile peripheral member 670 has a peripheral height dimension 690 that is less than, e.g., 75% lower than, in some cases 50% lower than, and in some cases 25% lower than, the peripheral member height dimension 662. As shown in FIG. 20B the peripheral height dimension 690 can be defined between the patient specific contact surface 658 of the low profile peripheral member 670 and a side 692 opposite the patient specific contact surface 658 of the low profile peripheral member 670. In one embodiment, the side 692 of the low profile peripheral member 670 is at a lower height than the side 666 of the elongate member 656 of the other peripheral members 608. In one embodiment, the side 692 of the low profile peripheral member 670 is at a lower height than the second end 624 of the hub 604. The low profile of the peripheral member 670 allows the retractor 16 to have greater access in the portion of the glenoid 18 over which the posterior portion 612 of the patient specific shoulder guide 600 extends or is disposed and to portions of the scapula that a posterior to that location. This allows the retractor 16 to be positioned posterior to the glenoid 18 and move soft tissue out of the surgical field to provide access to the glenoid 18 of the patient without risk of disruptive contact between the retractor 16 and the patient specific shoulder guide 600.

FIGS. 21-21B illustrate a low profile patient specific shoulder guide 700 that is similar to the guide 600 except as described differently below. The patient specific shoulder guide 700 is configured to provide enhanced engagement with a portion of a glenoid rim. The patient specific shoulder guide 700 is configured to provide enhanced stability on one side of the glenoid 18. The patient specific shoulder guide 700 includes a posterior side 702 and an anterior side 704. The posterior side 702 and the anterior side 704 are each disposed away from a hub 706 which is generally centrally located on the patient specific shoulder guide 700. The posterior side 702 extends from the hub 706 to a location over a posterior portion of the glenoid 18 when applied to the scapula 14. The anterior side 704 extends from the hub 706 to a location over an anterior portion of the glenoid 18 when applied to the scapula 14. The hub 706 is also disposed at a center of a plurality of peripheral members 708. The peripheral members 708 can each be coupled with an outside surface of the hub 706. The peripheral members 708 can extend radially away from the hub 706.

The peripheral members 708 can each include an inner end 712 and an outer end 716. The inner ends 712 can be directly coupled with the hub 706. The outer end 716 can be disposed away from the inner end 712 and away from the hub 706. In the illustrated embodiment, the posterior side 702 includes one peripheral member 708 and the anterior side 704 includes a plurality of, e.g., three, peripheral members 708. Other numbers of peripheral members 708 can be provided. Other distributions of peripheral members 708 can be provided. As in other guides herein, more than one peripheral member 708 can be provided in the posterior side 702 and fewer than three peripheral members 708 can be provided in the anterior side 704 of the patient specific shoulder guide 700.

The hub 706 can have a central channel 736 that extend therethrough. The central channel 736 can provide access for the pin guide 590 as discussed above in connection with the patient specific shoulder guide 600. The patient specific shoulder guide 700 also can have a side member 740 through which a side channel 744 is disposed. The side channel 744 can be configured to allow a pin to be placed therethrough into the glenoid 18. The side channel 744 thus allows access for a device to control rotation of patient specific shoulder guide 700 while in use.

In one embodiment, one or more of the hub 706, the side member 740, and the peripheral members 708 disposed on the anterior side 704 of the patient specific shoulder guide 700 have proximal portions that are disposed in a common plane. In other words, height dimension of each of these components are measured from a common proximal plane. In one variation the proximal portion of each of the hub 706, the side member 740, and the peripheral members 708 is disposed in a common plane. The peripheral member 708 disposed in the posterior side 702 of the patient specific shoulder guide 700 has a low profile. The low profile is similar to the low profile of the peripheral members 608 in the posterior portion 612 of the patient specific shoulder guide 600 as discussed above. That is the peripheral height dimension 690 of the peripheral members 708 in the posterior side 702 is much less than the peripheral member height dimension 662 of the peripheral members 708 in the anterior side 704 of the patient specific shoulder guide 700.

In one variation the peripheral member 708 in the posterior side 702 includes an elongate member 720 disposed between the inner end 712 and the outer end 716. A peripheral elongate member 722 can be disposed at or adjacent to the outer end 716 of the peripheral members 708 on posterior side 702 of the patient specific shoulder guide 700. The peripheral elongate member 722 can have a patient specific contact surface 724 that is formed by reference to CT scan images or the like that can be obtained pre-operatively, as discussed above. The patient specific contact surface 724 preferably is a substantial negative of an elongate zone of the rim of the glenoid 18. In one embodiment, the peripheral elongate member 722 includes an inferior end 728 and a superior end 732. The peripheral elongate member 722 can span a large portion of the rim of the glenoid 18 compared to the contact features of the peripheral members 708 on the anterior side 704 of the patient specific shoulder guide 700. In one embodiment, the peripheral elongate member 722 has an inferior-superior extent that is at least three times the largest dimension of, e.g., the diameter of, the contact feature of the other peripheral members 708. In one embodiment, the peripheral elongate member 722 has an angle between lines centered on the center of the central channel 736 and tangentially contacting the inferior end 728 and the superior end 732 is greater than 5 degrees, or is greater than 10 degrees, or is greater than 15 degrees, or in some cases greater than 20 degrees. The angle between lines centered on the center of the central channel 736 and tangentially contacting the inferior end 728 and the superior end 732 can be between about 5 degrees and about 60 degrees, e.g., between about 10 and about 45 degrees, between about 15 and about 35 degrees.

The patient specific shoulder guide 700 can perform similar to the patient specific shoulder guide 600 in being low profile and not interfering with the retractors 16 and other instruments in the surgical field. The patient specific shoulder guide 700 can provide an additional advantage in reducing unwanted movement of the patient specific shoulder guide 700 on the glenoid 18. The surface area of contact of the peripheral elongate member 722 is much greater than that in the outer end 678 of the elongate member 682 of the patient specific shoulder guide 600. This is achieved without additional elongate members 720, which allows the access to the glenoid 18 to remain relatively open and unobstructed. Also, by increasing the surface area of contact forces applied to the patient specific shoulder guide 700 are spread out more lessening the pressure on the contact area on the rim of the glenoid 18.

FIGS. 22 and 22A show another embodiment of a patient specific shoulder guide 770 that has a low profile peripheral member 774. The peripheral member 774 is shown in FIG. 22A. It has a low profile peripheral height dimension 690 compared to a high profile peripheral member height dimension 662. The patient specific shoulder guide 770 can be similar to the guides hereinbefore described except as where described differently below.

The patient specific shoulder guide 770 includes a hub 772 from which the peripheral members 774 extend radially. Each of the peripheral members 774 has an inner end 776, an outer end 778 and an elongate member 780 therebetween. At least one of the peripheral members 774 is adapted for enhanced patient specific contact. For example, a peripheral member 774 in the posterior side of the patient specific shoulder guide 770 can include a rim engaging portion 782 and a glenoid surface engaging portion 784. The rim engaging portion 782 can be similar to the rim engaging portions discussed above in various other guides. The glenoid surface engaging portion 784 can comprise a portion of the elongate member 780 between the inner end 776 and the outer end 778. In one embodiment, the peripheral members 774 are configured based on CT scan images or the like obtained pre-operative with a continuous patient specific contact zone that extends from the rim engaging portion 782 to the glenoid surface engaging portion 784. The continuous patient specific contact zone can extend up to one-half the distance from the rim of the glenoid 18 to the hub 772. The continuous patient specific contact zone can extend at least sixty percent of the distance from the hub 772 to a portion of the patient specific shoulder guide 770 adapted to contact an outside of the rim of the glenoid 18 when applied. The continuous patient specific contact zone can extend at least seventy percent of the distance from the hub 772 to a portion of the patient specific shoulder guide 770 adapted to contact an outside of the rim of the glenoid 18 when applied.

The patient specific shoulder guide 770 can be configured such that the entire distal surface of at least one of the peripheral members 774, e.g., of the posterior side peripheral member 774, is in contact with the glenoid rim or surface in a patient-specific manner, e.g., as a negative of those natural surfaces. In one variation, one peripheral member 774 is configured in this manner and two additional peripheral members 774 for a total of only three peripheral members 774 are provided to provide patient specific contact with the glenoid rim. Where the peripheral member 774 is configured to be in contact with the glenoid 18, the peripheral member 774 can be configured to contact the sub-chondral surface. The peripheral member 774 can be configured to contact a cartilage surface over the articular surface of the glenoid 18.

FIG. 22 shows that in one embodiment, the distal end of the hub 772 is spaced proximally of the glenoid surface engaging portion 784 of the peripheral member 774 configured to contact the glenoid 18. A step can be provided between the distal face of the glenoid surface engaging portion 784 and the distal face of the hub 772. The step enables the portion of the hub 772 closest to the glenoid to be spaced way from and not contact the glenoid while a portion 778 of the glenoid surface engaging portion 784 is in direct contact with the glenoid adjacent to the step. The hub 772 has a central channel 790 disposed therethrough configured to mate with the pin guide 590 and/or receive a guide pin therethrough into the glenoid 18.

The patient specific shoulder guide 770 can include aside member 792 having a side channel 794 therethrough for placement of a pin for stabilizing the patient specific shoulder guide 770 in rotation.

The patient specific shoulder guide 770 is advantageous in that the amount of surface area of contact is greatly increased due to some or all of the length of the elongate member 780 on the posterior side of the patient specific shoulder guide 770 being in contact with the glenoid 18. The contact can allow the patient specific shoulder guide 770 to be made of a wider range of materials because the contact near the hub 772 reduces flexing of the patient specific shoulder guide 770 when the pin guide 590 is docked with the central channel 790. By reducing or eliminating flexing the trajectory of a guide pin through a pin guide 590 mated along the central longitudinal axis of the central channel 790 is better controlled, e.g., closer to the true trajectory that prescribed based on CT scan imaging or the like taken preoperative.

FIGS. 23-24B show embodiments of a patient specific shoulder guide 800 in which at least a plurality of peripheral members are lowered or are low profile to reduce or minimize the space needed to accommodate the guides. The patient specific shoulder guide 800 allows greater access to anterior and posterior, as well as to inferior and to superior regions of the glenoid 18 when the patient specific shoulder guide 800 is applied to the scapula 14 of a patient.

FIG. 23 shows that more than one of a plurality of peripheral members 808 are made low profile in the patient specific shoulder guide 800. The patient specific shoulder guide 800 includes a posterior portion 802 and an anterior portion 804. The posterior portion 802 includes one peripheral member 808 and the anterior portion 804 includes a plurality of, e.g., three, peripheral members 808. The peripheral members 808 extend radially away from a hub 806.

An outer end of the peripheral members 808 includes or is coupled with a member providing a patient specific contact surface 812. The patient specific contact surface 812 can be configured to mate with specific portions of the glenoid 18 or the scapula 14 based on preoperative characterization by CT scan or the like, as discussed above. The hub 806 defines a central channel 820. The central channel 820 is configured to mate with the pin guide 590 as discussed above in connection with other guides. The patient specific shoulder guide 800 includes a side channel 828 that extends therethrough from a proximal side to a distal portion thereof. The side channel 828 can be formed in a side member 824 of the hub 806. The side channel 828 can be configured to receive an anchor pin or member. The patient specific shoulder guide 800 can be stabilized by the placement of a pin through the side channel 828. In a variation, the side member 824 is elongated to enable placement of a peripheral pin such as the peripheral guide pin 208.

FIGS. 23 and 23B show that each of the peripheral members 808 extend from a common plane which can intersect a proximal side 832 of each member 808. As a result, the entire portion of the patient specific shoulder guide 800 radially outward of the hub 806 is low profile. This can be seen in comparing the height dimension 690 from a patient contact surface to lateral side 832 to the height dimension 834 from a patient contact surface to a lateral side of the hub 806. The height dimension 690 is much less than the height dimension 834 which enables the peripheral members 808 to be generally out of the way of surgical instruments around the periphery of the glenoid. The low profile portion of the patient specific shoulder guide 800 extends into the posterior portion 802 and in the anterior portion 804. This enables the retractor 16 and other surgical instruments on both sides of the patient specific shoulder guide 800 to have greater freedom of movement without impinging on or otherwise interacting with the patient specific shoulder guide 800. FIG. 23B shows that the entire peripheral region has the low profile peripheral height dimension 690. Also, the hub 806 is configured to extend above (e.g., proximally or laterally of) the proximal side 832. The hub 806 thus benefits from a high profile central height dimension 834. By elevating a proximal end of the hub 806, an interface region of the hub 806 can remain sufficiently elongated to provide for stable connection with the pin guide 590 so that good control of the trajectory of the longitudinal axis 596 of the pin guide 590 is maintained as discussed above.

FIGS. 24-24B show a patient specific shoulder guide 850 that is similar to the patient specific shoulder guide 800 in providing low profile peripheral members. The hub 856 of the patient specific shoulder guide 850 is configured not to extend above a lateral side 874 that resides in a plane that includes the proximal sides of glenoid rim members 858 of the guide 850. As discussed more fully below, the hub 856 of the patient specific shoulder guide 850 is configured to project medially of a medial side 876 of the glenoid rim members 858. More particularly, the hub 856 includes a medial end 857 that is significantly medial of the medial side 876 of the glenoid rim members 858. As used herein "medial" refers to being closer to the midline of a patient when the guide 850 is coupled with the glenoid rim than another portion that is less medial or that is more lateral with respect to the midline of a patient. As a result, the proximal-distal length of the hub 856 can be similar in the guide 850 as in hub 806 of the guide 800. Thus, even though the hub 856 does not project laterally of the lateral side 874 the patient specific shoulder guide 850 can achieve similar control over the longitudinal axis 596 of the pin guide 590 when docked with a central channel of the hub 856 as is achieved in the guide 800. The patient specific shoulder guide 850 can also be easily manufactured using additive manufacturing because all of the features of the guide 850 on the proximal side thereof reside in a common proximal plane as is seen in FIG. 24B.

B. Low Profile Glenoid Guides with Reduced Glenoid Rim Contact

FIGS. 24-26B also illustrate further embodiments of patient specific shoulder guides in which the profile thereof can be reduced by reducing the radial extent of or to eliminate one or more of a plurality of peripheral members to enhance access for the retractors 16 or for other surgical instruments that may be deployed in the surgical field.

1. Glenoid Guides with Shortened Peripheral Members

The patient specific shoulder guide 850 has been discussed in some detail above. Further unique features of the patient specific shoulder guide 850 include providing diverse configurations of peripheral members thereof. The patient specific shoulder guide 850 includes one or a plurality of glenoid rim members 858. The glenoid rim members 858 are adapted to contact a rim of a glenoid 18 of a specific patient, in much the same way as other guides described above. FIG. 24 shows each of three glenoid rim members 858 disposed on the peripheral rim of the glenoid 18. The distal surfaces of the outer ends of one or more of, e.g., each of, the glenoid rim members 858 has patient specific contours on a glenoid rim contact surface 862, similar to the guides discussed above. In other embodiments one or more of the glenoid rim members 858 are configured to contact structures around the glenoid 18, e.g., in the scapula 14 outside the rim of the glenoid 18. The patient specific shoulder guide 850 also includes one or more glenoid surface member 866. The glenoid surface member 866 is configured to contact a surface or a structure of the glenoid 18 disposed radially inward of the rim thereof. The glenoid surface member 866 can be configured to contact sub-chondral bone at a glenoid surface contact surface 870. The glenoid surface member 866 can be configured to contact the cartilage in the natural articular surface of the glenoid 18.

The patient specific shoulder guide 850 includes more than three contact surfaces which provides several advantages. Three contact surfaces, e.g., the glenoid rim contact surfaces 862, provide sufficient stability of a guide on a natural surface like the glenoid 18. By adding the fourth contact surface at glenoid surface contact surface 870 the surgeon can confirm that the procedure should continue with the patient specific shoulder guide 850. Furthermore, FIG. 24 shows that the glenoid surface member 866 can be positioned close in a radial direction to the hub 856 than are the contact surfaces of the glenoid rim members 858. The distance from the inner to the outer end of the glenoid surface member 866 can be much less than even the shortest of the glenoid rim members 858. As a result, the glenoid surface member 866 provides adjacent support for the hub 856. The adjacent support transfers distal forces and pressures that are applied when the pin guide 590 is coupled with a central channel 878 with the patient specific shoulder guide 850 to the surface of the glenoid 18. The radial shortness of the glenoid surface member 866 allows this force and pressure transfer with minimal to no flexing in the glenoid surface member 866. Thus control of the longitudinal axis 596 of the pin guide 590 is maintained or enhanced. Further, by moving this contact point radially inward of the glenoid rim, the peripheral member may be removed from interference with other surgical instruments.

As in other guides herein, the patient specific shoulder guide 850 can optionally have aside member 880 disposed adjacent to the central channel 878. The side member 880 can have a side channel 884 disposed therethrough. The side channel 884 can be configured to receive a pin or other structure configured to manage or help to maintain minimal rotation of the patient specific shoulder guide 850 relative to the glenoid 18. FIG. 24B shows that the side member 880 can be low profile such that the entire guide side member 880 has a proximal height that is reduced in addition to the radial extend of the glenoid surface member 866 be reduced compared to the glenoid rim members 858.

The patient specific shoulder guide 850 is also advantageous in that even the hub 856 is made low profile while maintaining the control of the pin guide 590. As a result, the hub 856 does not interfere with the retractor 16 or other instruments that are passed between the posterior portion 852 and the anterior portion 854 or between a superior and an inferior side of patient specific shoulder guide 850 or of the glenoid 18. The lower profile nature of the patient specific shoulder guide 850 can also enable the surgeon to retract the tissue less and to shorten the incision used to access the glenoid 18.

2. Glenoid Guides with Restricted Rim Contact Zones

FIGS. 25A-26B illustrate embodiments of glenoid guides in which reliable placement of the central guide pin 204 can be achieved while leaving large regions of a glenoid exposed without obstruction.

Figure 25B:
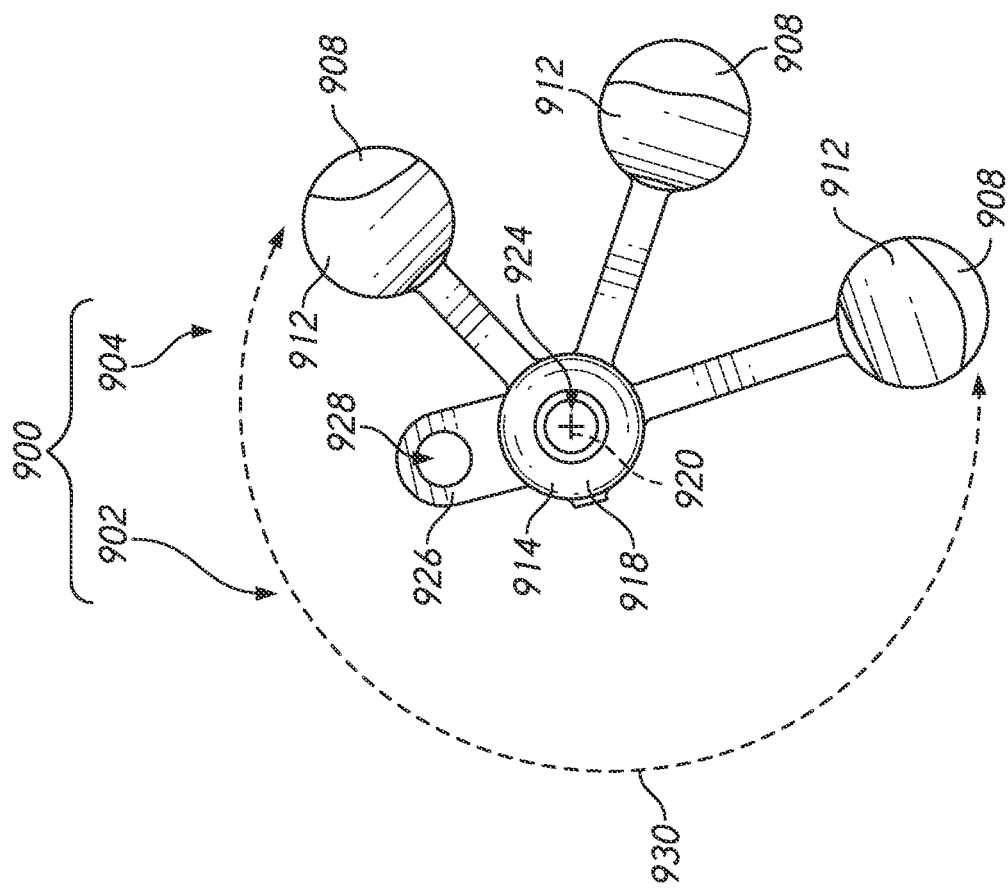
FIG. 25B is a medial or distal side view of the glenoid guide of FIG. 25A.
Figure 25A:
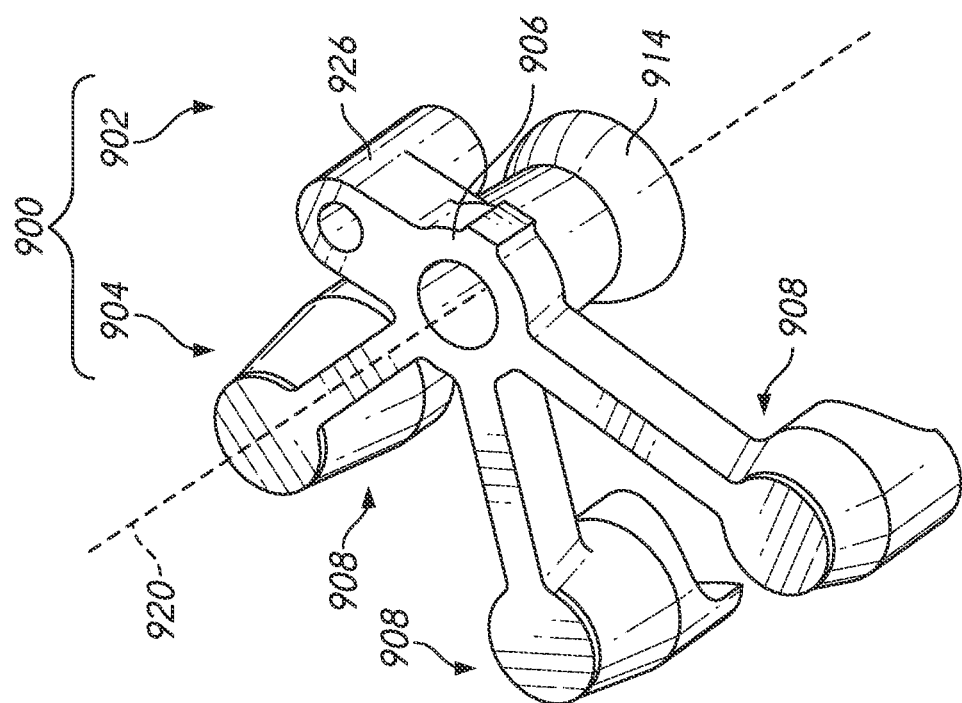
FIG. 25A is a lateral or proximal side perspective view of another embodiment of a low profile glenoid guide providing improved clearance for a tissue retractor.

FIG. 25A shows a patient specific shoulder guide 900 that includes a posterior portion 902 and an anterior portion 904. The patient specific shoulder guide 900 can be similar to other guides described above except as described differently below. For example, the anterior portion 904 can be similar to the anterior regions of other guides described above. The anterior portion 904 can include a plurality of glenoid rim members 908. The glenoid rim members 908 can extend from a hub 906 that is located centrally to the glenoid rim members 908. The glenoid rim members 908 can include elongate members with inner and outer ends, similar to the structures described above. The outer ends of each of the glenoid rim members 908 can be configured with a patient specific contact surface 912 disposed on or coupled therewith. The patient specific contact surface 912 can be made based on pre-operative CT scan imaging or the like as discussed above.

Figure 26B:
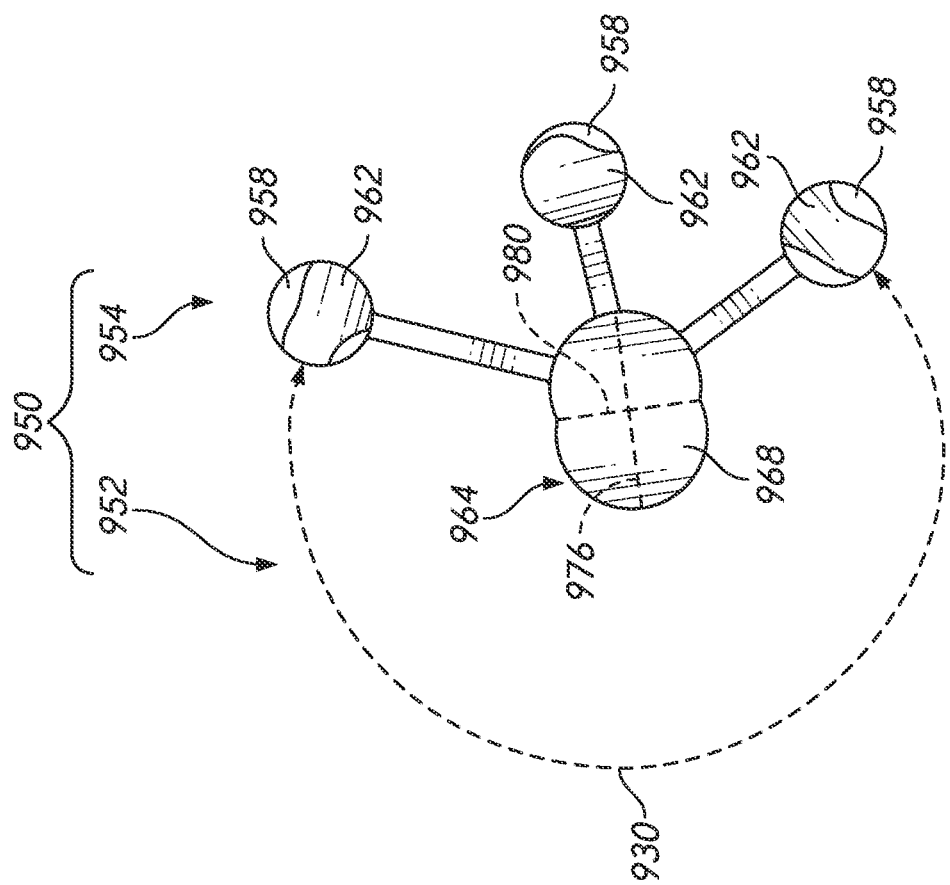
FIG. 26B is a medial or distal side view of the glenoid guide of FIG. 26A.
Figure 26A:
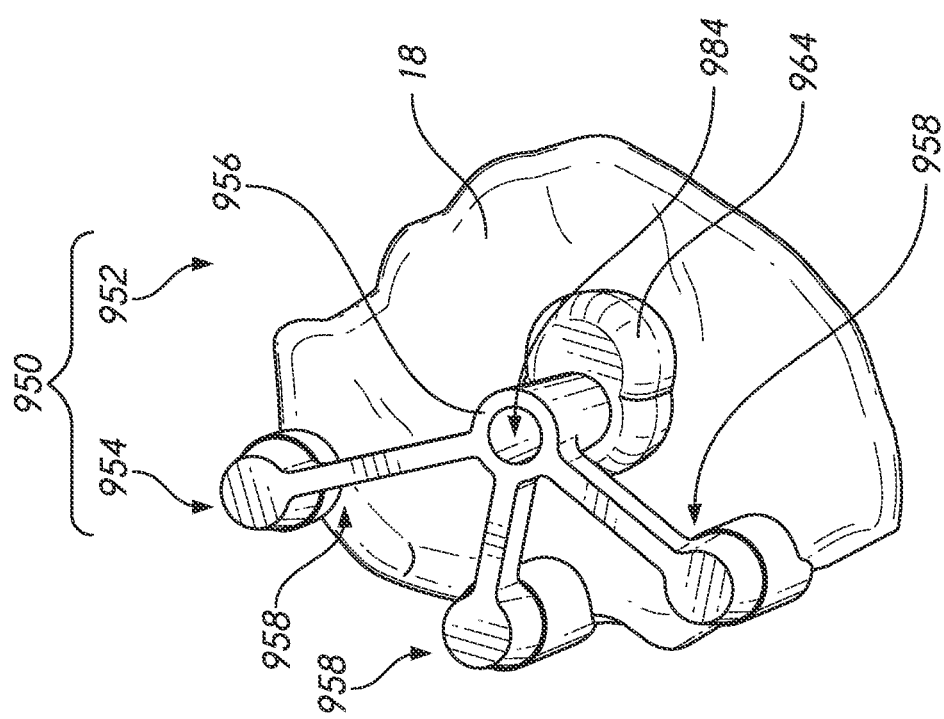
FIG. 26A shows a lateral or proximal side perspective view of another embodiment of a low profile glenoid guide placed on a scapula, the guide providing improved clearance for a tissue retractor.

In some variations, the shoulder guide 900 or other guides disclosed herein can be configured with no more than 3 peripheral legs, such as for example in connection with FIGS. 26A and 26B. In one variation the guide 950, discussed further below has no peripheral legs in a posterior portion of the guide 950. In one variation all of the legs are disposed in the anterior portion of the guide 950. Furthermore, in some variations the guides disclosed herein can be configured at least in part based on surgeon preference, patient needs, or both surgeon preference and patient needs to leave another portion, e.g., an anterior, superior, or inferior portion without any legs present in that or those portions. A portion can be defined between two or more portions, e.g., superior-posterior, inferior-posterior, superior-anterior, inferior-anterior, etc.

The patient specific shoulder guide 900 can also include a central member 914. The central member 914 is coupled with or can be an extension of the hub 906. The central member 914 can surround a longitudinal axis of a central channel 924 that is disposed through the patient specific shoulder guide 900, e.g., through the hub 906 and the central member 914. The central member 914 includes a patient specific contact surface 918. The distal face of the central member 914 can be patient specific. The central member 914 can include an annular contact face that is formed based on a specific patient's anatomy toward the central region of the glenoid 18 of the patient. The distal face of the central member 914 can be generally convex to follow the generally concave surface of sub-chondral bone. The distal face of the central member 914 can be formed to follow cartilage if mating the central member 914 to the cartilage is preferred. In one embodiment the glenoid rim members 908 and the central member 914 are configured to conform to bone, e.g., as negatives of the natural bone anatomy, including osteophytes. In one embodiment one or more of the glenoid rim members 908 and the central member 914 can be configured to conform with cartilage while the other of the glenoid rim members 908 and the central member 914 can be configured to conform to bone, e.g., as negatives of the natural bone anatomy, including osteophytes.

The central member 914 can include a circular contact profile. The patient specific contact surface 918 can extend from an outer periphery of the central channel 924 to an outer periphery of the central member 914. The outer periphery of the central member 914 can be circular. The diameter of the outer periphery can be sized to provide sufficient stability of the patient specific shoulder guide 900 to tipping.

The patient specific shoulder guide 900 can include an side member 926. The side member 926 can have a side channel 928 disposed therethrough. The side channel 928 can be used to place an anti-rotation device such as a pin into the glenoid. The central channel 924 can be used to place the central guide pin 204. In one modified embodiment, the side member 926 is eliminated. The modified embodiment may be configured with a larger diameter outer periphery of the central member 914 to provide greater stability in the absence of a pin which could be placed through the side member 926.

The patient specific shoulder guide 900 is advantageous in leaving a large span 930 of the surgical field un-obstructed. For example, a span 930 of more than 120 degrees can be unobstructed by the presence of a glenoid rim member 908. In some embodiments, a span 930 of more than 130 degrees can be unobstructed by the presence of a glenoid rim member 908. In some embodiments, a span 930 of more than 140 degrees can be unobstructed by the presence of a glenoid rim member 908. In some embodiments, a span 930 of more than 150 degrees can be unobstructed by the presence of a glenoid rim member 908. In some embodiments, a span 930 of more than 160 degrees can be unobstructed by the presence of a glenoid rim member 908. In some embodiments, a span 930 of more than 170 degrees can be unobstructed by the presence of a glenoid rim member 908. In some embodiments, a span 930 of more than 180 degrees can be unobstructed by the presence of a glenoid rim member 908. In some embodiments, a span 930 of more than 190 degrees can be unobstructed by the presence of a glenoid rim member 908. In some embodiments, a span 930 of more than 200 degrees can be unobstructed by the presence of a glenoid rim member 908. In some embodiments, a span 930 of more than 210 degrees can be unobstructed by the presence of a glenoid rim member 908. In some embodiments, a span 930 of more than 220 degrees can be unobstructed by the presence of a glenoid rim member 908. In some embodiments, a span 930 of more than 230 degrees can be unobstructed by the presence of a glenoid rim member 908. In some embodiments, a span 930 of more than 240 degrees can be unobstructed by the presence of a glenoid rim member 908. In some embodiments, a span 930 of more than 250 degrees can be unobstructed by the presence of a glenoid rim member 908. In some embodiments, a span 930 of more than 260 degrees can be unobstructed by the presence of a glenoid rim member 908. In some embodiments, a span 930 of between 180 degrees and 260 degrees can be unobstructed by the presence of a glenoid rim member 908.

In some embodiments, the glenoid rim members 908 can be disposed in a zone of less than 180 degrees of the patient specific shoulder guide 900. In some embodiments, the glenoid rim members 908 can be disposed in a zone of less than 170 degrees of the patient specific shoulder guide 900. In some embodiments, the glenoid rim members 908 can be disposed in a zone of less than 160 degrees of the patient specific shoulder guide 900. In some embodiments, the glenoid rim members 908 can be disposed in a zone of less than 150 degrees of the patient specific shoulder guide 900. In some embodiments, the glenoid rim members 908 can be disposed in a zone of less than 140 degrees of the patient specific shoulder guide 900. In some embodiments, the glenoid rim members 908 can be disposed in a zone of less than 130 degrees of the patient specific shoulder guide 900. In some embodiments, the glenoid rim members 908 can be disposed in a zone of less than 120 degrees of the patient specific shoulder guide 900. In some embodiments, the glenoid rim members 908 can be disposed in a zone of less than 110 degrees of the patient specific shoulder guide 900. In some embodiments, a span of between 45 degrees and 180 degrees can enclosed all of the glenoid rim members 908.

FIGS. 26A and 26Bf illustrate a patient specific shoulder guide 950 that is similar to the patient specific shoulder guide 900 except as described differently below. The patient specific shoulder guide 950 also includes a posterior portion 952 that is free of glenoid rim members 958. The shoulder guide 950 is configured such that it consists essentially of glenoid contact members that are anterior of a posterior portion of the glenoid rim, e.g., are in a central region of the glenoid and/or in the anterior region of the glenoid rim. The patient specific shoulder guide 950 has an anterior portion 954 in which the glenoid rim members 958 are disposed.

Each of the glenoid rim members 958 includes a patient specific contact surface 962 coupled with or disposed at outer ends of an elongate member thereof. The patient specific shoulder guide 950 thus retains an unobstructed the posterior portion 952 allowing the retractor 16 and other instruments free access to the posterior portion of the glenoid 18. The extent of the unobstructed posterior portion 952 can be similar to the extent of the unobstructed posterior portion 902 as discussed above in connection with the patient specific shoulder guide 900. The bounds of a zone of the anterior portion 954 that contains the glenoid rim members 958 can be similar to the bounds of the zone of the anterior portion 904 that contains the glenoid rim members 908.

The patient specific shoulder guide 950 includes a hub 956 through which a central channel 984 extends. A patient specific contact surface 962 can be disposed at or coupled with a distal portion of the hub 956. The patient specific contact surface 962 includes a patient specific contact surface 968 that is formed by reference to the specific patient. The patient specific contact surface 962 also can be configured to reduce flexing in or rotation of the patient specific shoulder guide 950 in use. The patient specific contact surface 962 can be non-round in one embodiment. The patient specific contact surface 962 can be elongated in one embodiment. In some embodiment, the shoulder guide 950 is configured to eliminate or compensate for there being no glenoid rim member 958 in a posterior side of the guide 950. For example, the patient specific contact surface 962 can be elongated and can extend in a posterior direction. In some embodiments, the contact surface 962 is elongated and a rim member 958 is disposed in the posterior portion of the guide 950. In other embodiments the contact surface 962 is sufficiently elongated to eliminate the posterior side rim member 958. The patient specific contact surface 962 can have an anterior-posterior extent 976 and a superior-inferior extent 980 in one embodiment. FIG. 26B shows that the anterior-posterior extent 976 can be greater than the superior-inferior extent 980. In one embodiment, the anterior-posterior extent 976 is more than 20% larger than the superior-inferior extent 980 of the patient specific contact surface 962. In one embodiment, the anterior-posterior extent 976 is more than 30% larger than the superior-inferior extent 980 of the patient specific contact surface 962. In one embodiment, the anterior-posterior extent 976 is more than 40% larger than the superior-inferior extent 980 of the patient specific contact surface 962. In one embodiment, the anterior-posterior extent 976 is more than 50% larger than the superior-inferior extent 980 of the patient specific contact surface 962. In one embodiment, the anterior-posterior extent 976 is more than 70% larger than the superior-inferior extent 980 of the patient specific contact surface 962. In one embodiment, the anterior-posterior extent 976 is more than 80% larger than the superior-inferior extent 980 of the patient specific contact surface 962. In one embodiment the anterior-posterior extent 976 is between 20 and 100% larger than the superior-inferior extent 980 of the patient specific contact surface 962.

The central member 964 can have a contact profile, e.g., outer periphery that is not round, as discussed above. The contact profile can be oblong or elongated. The contact profile can comprise two circular profiles that are partially overlapping such that end portions thereof can be circular and elongated sides thereof can be somewhat concave. The patient specific contact surface 968 can be formed to follow a natural surface of the articular portion of the glenoid 18, e.g., having a generally convex profile to follow the generally concave form of the articular surface.

The greater anterior-posterior extent 976 of the patient specific shoulder guide 950 compensates for the absence of any glenoid rim members 958 in the posterior portion 952. The shoulder guide 950 is configured to eliminate or compensate for there being no support on the posterior portion 952 of the guide 950. For example, the anterior-posterior extent 976 can be elongated more toward the posterior direction. In some embodiments, anterior-posterior extent 976 is sufficient to exclude the presence of rim contact in the posterior side of the rim in use. For example, any force directed toward the medial and posterior directions of the glenoid 18 will not tend to tip the patient specific shoulder guide 950. Rather, such forces will be transferred in a controlled manner to a surface of the glenoid 18, e.g., to the sub-chondral or cartilage surface thereof. By elongating the anterior-posterior extent 976 greater control of the patient specific shoulder guide 950 can be provided without unnecessarily expanding the superior-inferior extent 980. The anterior-posterior extent 976 need not be centered on the central channel 984. Rather, the anterior-posterior extent 976 can extend a greater amount toward the posterior direction than toward the anterior direction. This can further help compensate for the lack of glenoid rim members 958 in the posterior portion 952 of the patient specific shoulder guide 950.

A modified embodiment of the patient specific shoulder guide 950 includes a side member similar to the side member 926 in the patient specific shoulder guide 900. Such a side member can have a side channel disposed therethrough similar to the side channel 928 of the patient specific shoulder guide 900.

The patient specific shoulder guide 950 can have a span 930 with any of the amounts or degrees discussed above in connection with patient specific shoulder guide 900. The span 930 is generally unobstructed of any glenoid rim members 958. A zone can be provided in which the glenoid rim members 958 are disposed, as discussed above in connection with the patient specific shoulder guide 900.

Terminology

Although certain embodiments have been described herein, the implants and methods described herein can interchangeably use any articular component, as the context may dictate.

As used herein, the relative terms "proximal" and "distal" shall be defined from the perspective of the implant. Thus, proximal refers to the direction of the articular component and distal refers to the direction of an anchor component, such as a stem of a humeral anchor or a thread or porous surface or other anchoring structure of a stemless anchor when the implant is assembled.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1" includes "1." Phrases preceded by a term such as "substantially," "generally," and the like include the recited phrase and should be interpreted based on the circumstances (e.g., as much as reasonably possible under the circumstances). For example, "substantially spherical" includes "spherical." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Although certain embodiments and examples have been described herein, it should be emphasized that many variations and modifications may be made to the humeral head assembly shown and described in the present disclosure, the elements of which are to be understood as being differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, it will be understood by those skilled in the art that the scope of the inventions extends beyond the specifically disclosed embodiments to any and all embodiments having equivalent elements, modifications, omissions, combinations or sub-combinations of the specific features and aspects of the embodiments (e.g., of aspects across various embodiments), adaptations and/or alterations, and uses of the inventions as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "coupling a glenoid guide with the glenoid rim" include "instructing coupling of a glenoid guide with a glenoid rim."

What is claimed is:

1. A patient specific glenoid guide, comprising:
   a hub including a first end configured to oppose a central portion of a glenoid surface, a second end opposite the first end, and a hub body that is between the first end and the second end, the hub body having a central channel therethrough; and
   a plurality of peripheral members, each of the plurality of peripheral members including an inner end coupled with the hub, an outer end located radially away from the hub and including a cylindrical body, and a patient specific contact surface at the outer end; wherein
   one of the plurality of peripheral members includes a U-shaped rotation control feature forming channel configured to define an elongated visual indicator on a scapula of a specific patient in a prescribed position relative to a portion of the glenoid of the specific patient to be augmented by an augmented glenoid implant, and
   a point at a bottom of an arc of the U-shaped rotation control feature forming channel is on an axis extending from a center of the hub, along a longitudinal center of the inner end, and through a center of the cylindrical body of the one of the plurality of peripheral members.

2. The patient specific glenoid guide of claim 1, wherein the rotation control feature forming channel is disposed at a position disposed away from the portion of the glenoid of the specific patient to be augmented, the position based on a contour of the glenoid of the specific patient.

3. The patient specific glenoid guide of claim 2, wherein the rotation control feature forming channel is disposed opposite of the portion of the glenoid of the specific patient to be augmented.

4. The patient specific glenoid guide of claim 1, wherein the rotation control feature forming channel is disposed in an anterior portion of the patient specific glenoid guide.

5. The patient specific glenoid guide of claim 1, wherein the central channel is disposed within the patient specific glenoid guide such that when the patient specific contact surfaces of the peripheral members contact the glenoid rim of a specific patient the central channel is off-set from a geometric center of the glenoid of the specific patient.

6. The patient specific glenoid guide of claim 1, wherein the rotation control feature forming channel comprises an enclosed periphery that is enclosed along the length thereof.

7. The patient specific glenoid guide of claim 1, wherein the rotation control feature forming channel includes an open periphery that is surrounded on a radially inward side and is open on a radially outward side of the patient specific glenoid guide.

8. The patient specific glenoid guide of claim 1, further comprising an aperture defined in a periphery of the patient specific glenoid guide, the aperture configured to receive a guide pin therethrough to provide placement of a peripheral guide pin.

9. The patient specific glenoid guide of claim 1, wherein
   each of the plurality of peripheral members has a height between the patient specific contact surface and a side opposite the patient specific contact surface, and
   the height of one of the plurality of peripheral members is less than the height of one other of the plurality of peripheral members.

10. The patient specific glenoid guide of claim 9, wherein the one of the plurality of peripheral members is configured to avoid contact with other instruments in a surgical field.

* * * * *